United States Patent
Tzanis et al.

(10) Patent No.: US 10,835,542 B2
(45) Date of Patent: *Nov. 17, 2020

(54) 9-AMINOMETHYL MINOCYCLINE COMPOUNDS AND USE THEREOF IN TREATING COMMUNITY-ACQUIRED BACTERIAL PNEUMONIA (CABP)

(71) Applicant: Paratek Pharmaceuticals, Inc., Boston, MA (US)

(72) Inventors: Evangelos L. Tzanis, Newtown Square, PA (US); Paul McGovern, Berwyn, PA (US); Amy L. Manley, Phoenixville, PA (US); Lynne Garrity-Ryan, Melrose, MA (US); S. Ken Tanaka, Bellevue, WA (US)

(73) Assignee: Paratek Pharmaceuticals, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/507,410

(22) Filed: Jul. 10, 2019

(65) Prior Publication Data

US 2020/0009162 A1 Jan. 9, 2020

Related U.S. Application Data

(63) Continuation of application No. 15/798,573, filed on Oct. 31, 2017, now Pat. No. 10,383,884.

(60) Provisional application No. 62/514,415, filed on Jun. 2, 2017, provisional application No. 62/500,611, filed on May 3, 2017, provisional application No. 62/480,516, filed on Apr. 2, 2017, provisional application No. 62/422,843, filed on Nov. 16, 2016, provisional application No. 62/416,010, filed on Nov. 1, 2016.

(51) Int. Cl.
| | | |
|---|---|---|
| *A61K 31/65* | (2006.01) | |
| *A61K 9/00* | (2006.01) | |
| *A61P 11/00* | (2006.01) | |
| *A61P 31/04* | (2006.01) | |

(52) U.S. Cl.
CPC ............ *A61K 31/65* (2013.01); *A61K 9/0019* (2013.01); *A61K 9/0053* (2013.01); *A61P 11/00* (2018.01); *A61P 31/04* (2018.01); *Y02A 50/30* (2018.01)

(58) Field of Classification Search
None
See application file for complete search history.

(56) References Cited

U.S. PATENT DOCUMENTS

| | | |
|---|---|---|
| 2,980,584 A | 4/1961 | Hammer |
| 2,990,331 A | 6/1961 | Neumann et al. |
| 3,062,717 A | 11/1962 | Hammer |
| 3,165,531 A | 1/1965 | Blackwood et al. |
| 3,454,697 A | 7/1969 | Joyner et al. |
| 3,557,280 A | 1/1971 | Weber et al. |
| 3,674,859 A | 7/1972 | Beutel et al. |
| 3,957,980 A | 5/1976 | Noseworthy |
| 4,018,889 A | 4/1977 | Armstrong |
| 4,024,272 A | 5/1977 | Rogalski et al. |
| 4,126,680 A | 11/1978 | Armstrong |
| 4,806,372 A | 2/1989 | Strumskis |
| 5,021,407 A | 6/1991 | Levy |
| 5,258,372 A | 11/1993 | Levy |
| 5,589,470 A | 12/1996 | Levy |
| 5,811,412 A | 9/1998 | Levy |
| 6,256,365 B1 | 7/2001 | Lai |
| 6,500,812 B2 | 12/2002 | Nelson et al. |
| 6,617,318 B1 | 9/2003 | Nelson et al. |
| 6,624,168 B2 | 9/2003 | Nelson et al. |
| 6,642,270 B2 | 11/2003 | Nelson et al. |
| 6,683,068 B2 | 1/2004 | Nelson et al. |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 | 1/2005 | Draper et al. |
| 6,846,939 B2 | 1/2005 | Nelson et al. |
| 6,849,615 B2 | 2/2005 | Nelson et al. |
| 7,001,918 B2 | 2/2006 | Huss et al. |
| 7,045,507 B2 | 5/2006 | Draper et al. |
| 7,056,902 B2 | 6/2006 | Nelson et al. |
| 7,067,681 B2 | 6/2006 | Nelson et al. |
| 7,094,806 B2 | 8/2006 | Nelson et al. |
| 7,202,235 B2 | 4/2007 | Levy et al. |
| 7,208,482 B2 | 4/2007 | Garcia-Luzon et al. |
| 7,323,492 B2 | 1/2008 | Huss et al. |

(Continued)

FOREIGN PATENT DOCUMENTS

| | | |
|---|---|---|
| DE | 2346535 A1 | 4/1974 |
| WO | WO-2004/091513 A2 | 10/2004 |

(Continued)

OTHER PUBLICATIONS

Paratek Pharmaceuticals, Form S-I Registration Statement under the Securities Act of 1933, Publicly available on Aug. 5, 2013, pp. 1-208 (Year: 2013).*

Arbeit et al., Safety and Efficacy of PTK 0796: Results of the Phase 2 Study in Complicated Skin and Skin Structure Infections Following IV and Oral Step Down Therapy. Abstract L-1515b, Session 126, ICAAC, ASM Society, 2008.

(Continued)

*Primary Examiner* — Dennis Heyer

(74) *Attorney, Agent, or Firm* — McCarter & English, LLP; Jonathan M. Sparks; Yu Lu

(57) ABSTRACT

The invention disclosed herein provides a method for treating Community-Acquired Bacterial Pneumonia (CABP) using 9-[(2,2-dimethyl-propyl amino)-methyl]-minocycline or a salt thereof, in either oral or IV doses or a combination of both.

43 Claims, 5 Drawing Sheets

(56) References Cited

U.S. PATENT DOCUMENTS

| | | | |
|---|---|---|---|
| 7,326,696 | B2 | 2/2008 | Nelson et al. |
| 7,361,674 | B2 | 4/2008 | Nelson et al. |
| 7,414,041 | B2 | 8/2008 | Levy |
| 7,521,437 | B2 | 4/2009 | Nelson et al. |
| 7,553,828 | B2 | 6/2009 | Nelson et al. |
| 9,265,740 | B2 | 2/2016 | Johnston et al. |
| 9,724,358 | B2 | 8/2017 | Johnston et al. |
| 10,111,890 | B2 | 10/2018 | Tanaka et al. |
| 10,124,014 | B2 | 11/2018 | Johnston et al. |
| 10,238,670 | B2 | 3/2019 | Manley et al. |
| 10,383,884 | B2 * | 8/2019 | Tzanis ............... A61K 9/0019 |
| 2003/0069721 | A1 | 4/2003 | Podlogar |
| 2004/0063674 | A1 | 4/2004 | Levy et al. |
| 2004/0138183 | A1 | 7/2004 | Nelson et al. |
| 2004/0176334 | A1 | 9/2004 | Nelson et al. |
| 2004/0214800 | A1 | 10/2004 | Levy et al. |
| 2004/0214801 | A1 | 10/2004 | Nelson et al. |
| 2004/0242548 | A1 | 12/2004 | Draper et al. |
| 2005/0020545 | A1 | 1/2005 | Draper et al. |
| 2005/0038002 | A1 | 2/2005 | Nelson et al. |
| 2005/0070510 | A1 | 3/2005 | Draper et al. |
| 2005/0143352 | A1 | 6/2005 | Nelson et al. |
| 2005/0250744 | A1 | 11/2005 | Levy et al. |
| 2005/0288262 | A1 | 12/2005 | Bandarage et al. |
| 2006/0003971 | A1 | 1/2006 | Nelson |
| 2006/0084634 | A1 | 4/2006 | Huss et al. |
| 2006/0089336 | A1 | 4/2006 | Nelson et al. |
| 2006/0166944 | A1 | 7/2006 | Berniac et al. |
| 2006/0166945 | A1 | 7/2006 | Abato et al. |
| 2006/0166946 | A1 | 7/2006 | Nelson et al. |
| 2006/0194773 | A1 | 8/2006 | Levy et al. |
| 2006/0281717 | A1 | 12/2006 | Berniac et al. |
| 2006/0287283 | A1 | 12/2006 | Amoo et al. |
| 2007/0072834 | A1 | 3/2007 | Nelson et al. |
| 2007/0093455 | A1 | 4/2007 | Abato et al. |
| 2007/0167415 | A1 | 7/2007 | Levy et al. |
| 2007/0270389 | A1 | 11/2007 | Garcia-Luzon et al. |
| 2008/0015169 | A1 | 1/2008 | Nelson et al. |
| 2008/0070873 | A1 | 3/2008 | Alekshun et al. |
| 2008/0118979 | A1 | 5/2008 | Draper et al. |
| 2008/0167273 | A1 | 7/2008 | Nelson et al. |
| 2008/0287401 | A1 | 11/2008 | Johnston et al. |
| 2008/0300424 | A1 | 12/2008 | Nelson et al. |
| 2008/0306032 | A1 | 12/2008 | Nelson et al. |
| 2008/0312193 | A1 | 12/2008 | Assefa et al. |
| 2009/0054379 | A1 | 2/2009 | Huss et al. |
| 2009/0118269 | A1 | 5/2009 | Berniac et al. |
| 2009/0124583 | A1 | 5/2009 | Nelson et al. |
| 2009/0131696 | A1 | 5/2009 | Levy |
| 2009/0156842 | A1 | 6/2009 | Seyedi et al. |
| 2009/0253660 | A1 | 10/2009 | Johnston |
| 2009/0306022 | A1 | 12/2009 | Nelson et al. |
| 2010/0022483 | A1 | 1/2010 | Berniac et al. |
| 2010/0113399 | A1 | 5/2010 | Cvetovich et al. |
| 2013/0109657 | A1 | 5/2013 | Zhou et al. |
| 2014/0005420 | A1 | 1/2014 | Cvetovich et al. |
| 2014/0255339 | A1 | 9/2014 | Sommadossi et al. |
| 2015/0087711 | A1 | 3/2015 | Johnston et al. |
| 2019/0125767 | A1 | 5/2019 | Tanaka et al. |

FOREIGN PATENT DOCUMENTS

| | | |
|---|---|---|
| WO | WO-2007/133797 A2 | 11/2007 |
| WO | WO-2007/133798 A2 | 11/2007 |
| WO | WO-2008/045507 A2 | 4/2008 |
| WO | WO-2008/079339 A2 | 7/2008 |
| WO | WO-2009/120389 A1 | 10/2009 |
| WO | WO-2009/143509 A1 | 11/2009 |
| WO | WO-2016/154332 A1 | 9/2016 |
| WO | 2017/165729 A1 | 9/2017 |

OTHER PUBLICATIONS

Berge et al., Pharmaceutical salts. J Pharm Sci. Jan. 1977;66(1):1-19.

Bhatia et al., Activity of BAY 73-7388, a Novel Aminomethylcycline, and Other Novel Antibiotic Classes Against Resistant Bacteria In Vitro. Poster P925, ECCMID, ESCMID, 2004.

Bhatia et al., PTK 0796 (BAY 73-6944) and other Novel Tetracycline Derivatives Exhibiting Potent In vitro and In vivo Activities Against Antibiotic Resistant Gram-Positive Bacteria. Abstract 2420, Poster F-755, ICAAC, ASM Society, 2003.

Broetz-Oesterhelt et al., Superior Efficacy of BAY 73-7388, a Novel Aminomethylcycline, Compared with Linezolid and Vancomycin in Murine Sepsis Caused by Susceptible or Multiresistant Staphylococci. Poster P930, ECCMID, ESCMID, 2004.

Cannon et al., Pharmacokinetics of PTK 0796 (BAY 73-6944) in Mouse, Rat and Cynomolgus Monkey. Abstract 2655, Poster F-759, ICAAC, ASM Society, 2003.

Caplus Accession No. 2009:581285, Amadacycline: tetracycline antibiotic, 2 pages, (2018).

Chaturvedi et al., In Vitro Assessment of Plasma Protein Binding and Metabolic Stability of PTK 0796 (BAY 73-6944). Abstract 2675, Poster F-760, ICAAC, ASM Society, 2003.

Craig et al., In Vivo Pharmacodynamics of MK-2764 / PTK 0796 Against Various Gram-positive and Gram-negative Bacteria in the Thighs of Neutropenic and Normal Mice. Abstract 1875, Poster F1-1974, ICAAC, ASM Society, 2006.

De Souza Mendes et al., Pipeline of Known Chemical Classes of Antibiotics. Antibiotics (Basel). Dec. 6, 2013;2(4):500-34.

Dubois et al., In Vitro Activity of MK-2764 / PTK 0796 Against *Legionella* spp. Abstract 1846, Poster F1-1972, ICAAC, ASM Society, 2006.

Endermann et al., BAY 73-7388 is Highly Efficacious in Animal Models of Intraabdominal Infections Caused by a Range of Aerobic and Anaerobic Organisms, Including VRE. Poster P928, ECCMID, ESCMID, 2004.

Endermann et al., BAY 73-7388, a Novel Aminomethylcycline, Is Highly Active In Vivo in a Murine Model of Pneumococcal Pneumonia. Poster P931, ECCMID, ESCMID, 2004.

Flamm et al., Activity of Omadacycline Tested against Enterobacteriaceae Causing Urinary Tract Infections from a Global Surveillance Program. ICAAC, Abstract C-614, 1 page, (2015).

Gorwitz et al., Strategies for Clinical Management of MRSA in the community: Summary of an Experts' Meeting Convened by the Centers for Disease Control and Prevention. Centers for Disease Control and Prevention. Retrieved online at: http://www.cdc.gov/ncidod/dhqp/ar_mrsa_ca.html. 24 pages. Mar. 2006.

International Search Report and Written Opinion for Application No. PCT/US2017/045220, dated Oct. 12, 2017, 17 pages.

International Search Report and Written Opinion for Application No. PCT/US2017/059165, dated Jan. 9, 2018. 13 pages.

Kattan et al., Acute Uncomplicated Urinary Tract Infections. Cleveland Clinic, Center for Continuing Education. 14 pages, Nov. 2013.

Ladel et al., BAY 73-7388 Demonstrates Greater Activity than Linezolid in a Range of Murine Models of Skin and Soft Tissue Infection. Poster P929, ECCMID, ESCMID, 2004.

Levison et al., Pharmacokinetics and pharmacodynamics of antibacterial agents. Infect Dis Clin North Am. Dec. 2009;23(4):791-815, vii.

Macone et al., Potent activity of BAY 73-7388, a Novel Aminomethylcycline, Against Susceptible and Resistant Gram-Positive and Gram-Negative Organisms. Poster P926, ECCMID, 2004.

Mckenney et al., BAY 73-7388, a Novel Aminomethylcycline, Exhibits Potent Efficacy in Pulmonary Murine Models of Infection. Poster P927, ECCMID, ESCMID, 2004.

Mckenney et al., Evaluation of PTK 0796 (BAY 73-6944) in Experimental Models of Infections Caused by Gram-Positive and Gram-Negative Pathogens. Abstract 2627, Poster F-757, ICAAC, ASM Society, 2003.

Mckenney et al., The Efficacy of PTK 0796 (BAY 73-6944) in Murine Models of *Streptococcus pneumoniae* Infections. Abstract 2637, Poster F-758, ICAAC, ASM Society, 2003.

(56) References Cited

OTHER PUBLICATIONS

Noel et al., A randomized, evaluator-blind, phase 2 study comparing the safety and efficacy of omadacycline to those of linezolid for treatment of complicated skin and skin structure infections. Antimicrob Agents Chemother. Nov. 2012;56(11):5650-4.
Paratek Pharmaceuticals, Form S-I Registration Statement under the Securities Act of 1933, Publicly available on Aug. 5, 2013, pp. 1-208.
Pneumonia Severity Index for CAP (PORT) (https://www.mdcalc.com/psi-port-score-pneumonia-severity-index-cap) (retrieved from the internetOct. 16, 2018).
Smith et al., Antistaphylococcal Activity of MK-2764 / PTK 0796 Compared to Other Agents. Abstract 1860, Poster F1-1971, ICAAC, ASM Society, 2006.
Tessier et al., Pharmacokinetic/Pharmacodynamic Profile of MK-2764 / PTK 0796 against *S. pneumoniae* in a Murine Pneumonia Model. Abstract 1888, Poster F1-1973, ICAAC, ASM Society, 2006.
Traczewski et al., PTK 0796 (BAY 73-6944): Effects of Environmental Variation on MICs and Confirmation of Disk Mass. Abstract 2463, Poster F-756, ICAAC, ASM Society, 2003.
Traczewski et al., PTK 0796 (BAY 73-6944): In Vitro Potency and Spectrum of Activity Compared to Ten Other Antimicrobial Compounds. Abstract 2458, Poster F-753, ICAAC, ASM Society, 2003.
Villano et al., Omadacycline: development of a novel aminomethylcycline antibiotic for treating drug-resistant bacterial infections. Future Microbiol. Oct. 2016;11:1421-1434.
Weir et al., The Activity of PTK 0796 (BAY 73-6944) Against Tetracycline Resistance. Abstract 2611, Poster F-752, ICAAC, ASM Society, 2003.
Weir et al., The Mechanism of Action of PTK 0796 (BAY 73-6944). Abstract 2473, Poster F-751, ICAAC, ASM Society, 2003.
Boxmeyer, Paratek Pharmaceuticals Announces FDA Grant of Qualified Infectious Disease Product (QIDP) Designation for Its Lead Product Candidate, Omadacycline. QIDP Status Designated for Both Intravenous and Oral Formulations. PRNewswire, 2 pages, Jan. 3, 2013.
Liapikou et al., New antimicrobial approaches to gram positive respiratory infections. Pulm Pharmacol Ther. 2015;32:137-143.
Tanaka et al., Discovery, pharmacology, and clinical profile of omadacycline, a novel aminomethylcycline antibiotic. Bioorg Med Chem. 2016;24(24):6409-6419.

\* cited by examiner

Clinical Success at PTE by Baseline Pathogen*

| Baseline Pathogen | Omadacycline (N=204) N | Omadacycline (N=204) Clinical Success n (%) | Moxifloxacin (N=182) N1 | Moxifloxacin (N=182) Clinical Success n (%) |
|---|---|---|---|---|
| Atypical Pathogens | 118 | 109 (92.4) | 106 | 97 (91.5) |
| Mycoplasma pneumoniae | 70 | 66 (94.3) | 57 | 50 (87.7) |
| Chlamydophila pneumoniae | 28 | 25 (89.3) | 28 | 25 (89.3) |
| Legionella pneumophila | 37 | 35 (94.6) | 37 | 36 (97.3) |
| Gram-Negative Bacteria (aerobes) | 79 | 67 (84.8) | 68 | 55 (80.9) |
| Haemophilus influenzae | 32 | 26 (81.3) | 16 | 16 (100.0) |
| Haemophilus parainfluenzae | 18 | 15 (83.3) | 17 | 13 (76.5) |
| Klebsiella pneumoniae | 13 | 10 (76.9) | 13 | 11 (84.6) |
| Gram-Positive Bacteria (aerobes) | 61 | 52 (85.2) | 56 | 49 (87.5) |
| Streptococcus pneumoniae | 43 | 37 (86.0) | 34 | 31 (91.2) |
| PSSP | 26 | 23 (88.5) | 22 | 21 (95.5) |
| Macrolide Resistant | 10 | 10 (100.0) | 5 | 5 (100.0) |
| Staphylococcus aureus | 11 | 8 (72.7) | 11 | 9 (81.8) |

*10 or More Isolates

FIG. 4

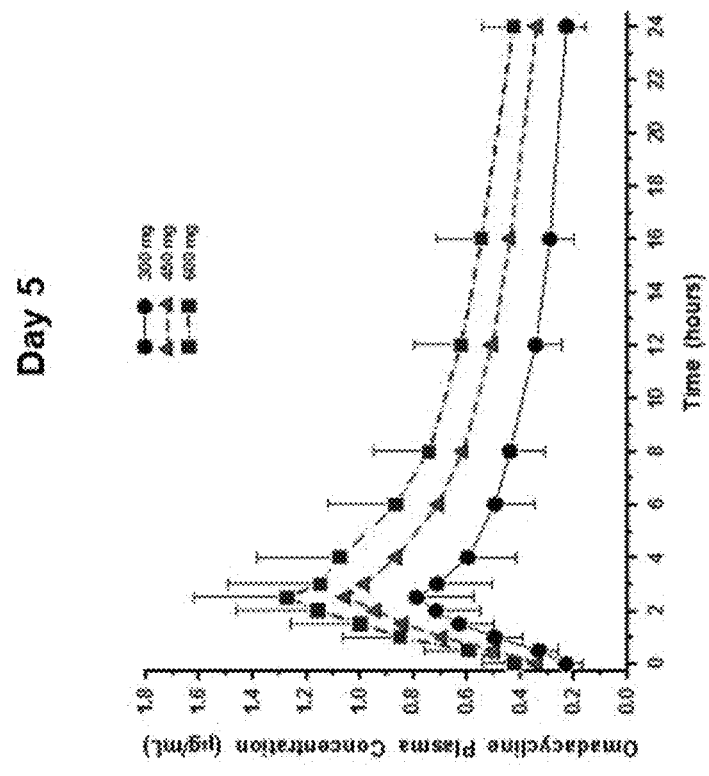
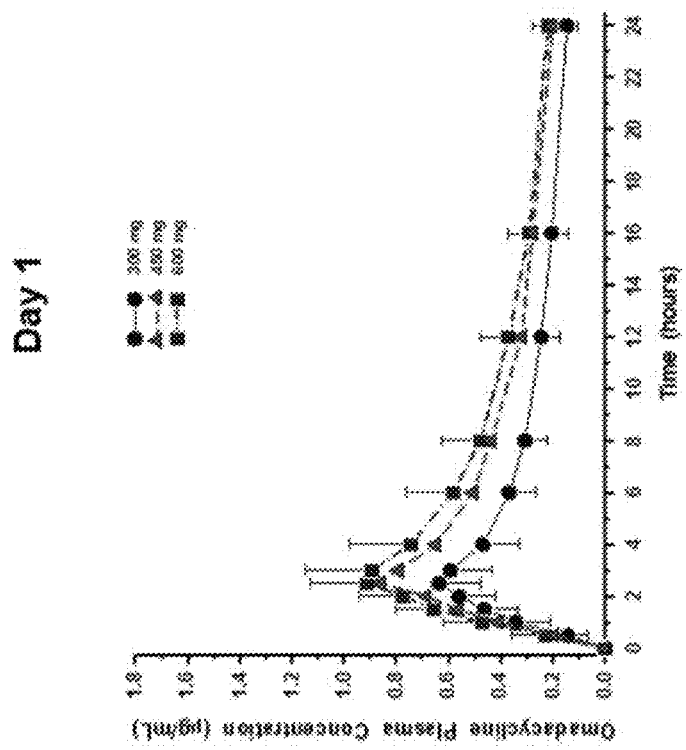
FIG. 5

9-AMINOMETHYL MINOCYCLINE COMPOUNDS AND USE THEREOF IN TREATING COMMUNITY-ACQUIRED BACTERIAL PNEUMONIA (CABP)

REFERENCE TO RELATED APPLICATIONS

This application is a continuation of U.S. patent application Ser. No. 15/798,573, filed on Oct. 31, 2017, which claims the benefit of the filing dates under 35 U.S.C. § 119(e) of U.S. Provisional Application Nos. 62/416,010, filed on Nov. 1, 2016; 62/422,843, filed on Nov. 16, 2016; 62/480,516, filed on Apr. 2, 2017; 62/500,611, filed on May 3, 2017; and 62/514,415, filed on Jun. 2, 2017, the entire contents of each of which are incorporated herein by reference.

BACKGROUND OF THE INVENTION

The development of the tetracycline antibiotics was the direct result of a systematic screening of soil specimens collected from many parts of the world for evidence of microorganisms capable of producing bactericidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of minocycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced minocycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against *Rickettsia*; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., Pneumococci and *Salmonella*). The rise of tetracycline-resistant organisms has resulted in a general decline in use of tetracyclines and tetracycline analogue compositions as antibiotics of choice. In addition, other antibacterial agents have also been over used creating strains of multiple drug resistant bacteria. Therefore, there is a need for effective antibacterial agents for the treatment of bacterial infections in general, particularly antibacterial agents with no or less severe resistance by disease-responsible pathogens.

Community Acquired Bacterial Pneumonia (CABP), also known as Community Acquired Pneumonia (CAP) (which terms can be used interchangeably), is defined as an acute bacterial infection of the pulmonary parenchyma associated with chest pain, cough, sputum production, difficulty breathing, chills, rigors, fever, or hypotension, and is accompanied by the presence of a new lobar or multilobar infiltrate on a chest radiograph. Common typical bacterial pathogens that cause CABP include *Streptococcus pneumoniae, Haemophilus influenzae, Staphylococcus aureus*, and *Moraxella catarrhalis*. Atypical bacterial pathogens such as *Chlamydophila pneumoniae, Mycoplasma pneumoniae*, and *Legionella pneumophila* also cause CABP.

CABP is a leading cause of morbidity and mortality in the United States (US) and throughout the world (Mandell et al., *Clin. Infect. Dis.* 44:S27-S72, 2007). Four to 6 million cases of CABP occur per year in the US, resulting in 10 million physician visits, 600,000 hospitalizations, and tens of thousands of deaths. The total cost of CABP to the annual US health care budget exceeds $10 billion (in 2007-adjusted dollars) (Niederman et al., *Clin. Ther.* 20(4): 820-37, 1998). Furthermore, there is increasing resistance to antibiotics among common pathogens, with a resulting critical need for new antibiotics (Spellberg et al., *Clin. Infect. Dis.* 46(2): 155-164, 2008). Bacterial resistance to the most frequently prescribed, currently available antibiotics has limited their potential to treat infections, which prevents their use as a first-line empiric monotherapy. Methicillin-resistant *Staphylococcus aureus* (MRSA) and multi-drug resistant *Streptococcus pneumoniae* (MDR-SP) in the community have posed treatment challenges because of resistance to penicillins (resistance rate 100% for both), cephalosporins (100% and 11%, respectively, for ceftriaxone), macrolides (83% and 86%, respectively, for azithromycin/erythromycin), and quinolones (73% and 2%, respectively, for levofloxacin), in CABP. In addition, the growing concern about, "collateral damage" associated with use of quinolone and beta-lactam class antibiotics further underscores the need for new antibiotic treatment options for CABP (Paterson, *Clin Infect Dis.* 38 Suppl 4: S341-345, 2004). Failure of therapy due to resistance will continue to contribute to the morbidity and mortality of CABP and treatment failures of mild disease will result in increased hospitalizations and contribute to increased healthcare costs.

SUMMARY OF THE INVENTION

The invention described herein provides 9-aminomethyl minocyclines, such as 9-[(2,2-dimethyl-propyl amino)-methyl]-minocycline (Omadacycline, or "Compound 1"), for use in the treatment of CABP.

The invention is also partly based on the discovery that 9-aminomethyl minocyclines, such as Compound 1, can be provided as IV dosage form for the treatment of CABP, either alone or in combination with oral dosage form (such as an oral step down after initial IV doses). In certain embodiments, the invention provides the use of 9-aminomethyl minocyclines, such as Compound 1, as IV dosage form for the treatment of CABP.

The invention is further based on the discovery that 9-aminomethyl minocyclines, such as Compound 1, has a relatively broad spectrum against a wide variety of pathogens associated with CABP, including intracellular CABP pathogens. The finding that Compound 1 has in vitro activity against common typical and atypical pathogens, and the sustained epithelial lining fluid (ELF) and alveolar cell (AC) including alveolar macrophages (AM) concentrations for 24 hours suggest that Compound 1 has utility as antibacterial agent for the treatment of lower respiratory tract bacterial infections caused by susceptible pathogens, such as intracellular CABP pathogens including *Legionella pneumophila, Mycoplasma pneumoniae, Chlamydophila pneumoniae, Chlamydophila psittaci*, and/or *Coxiella burnetii*.

The invention is further based on the discovery that 9-aminomethyl minocyclines, such as Compound 1, has a relatively broad spectrum against a wide variety of pathogens associated with CABP as further described below.

9-aminomethyl minocyclines, such as Compound 1, are also advantageous for treatment of CABP associated antibiotic-resistant pathogens, such as MRSA and penicillin-resistant *Streptococcus pneumoniae* (PRSP). Due to its efficacy against resistant pathogens, 9-aminomethyl minocyclines, such as Compound 1, can also be used as a front-line therapeutic agent in cases in which known or suspected drug-resistant bacteria may be the causative pathogen. On the other hand, 9-aminomethyl minocyclines, such as Compound 1, can also be used as a therapeutic agent in patients who have previously been treated by other antibiotics, but have had inadequate response or have developed/exhibited unacceptable or undesirable adverse events (AEs), such as gastrointestinal tracts AEs (GI tract AEs) and/or *C. difficile* infection.

Thus one aspect of the invention provides a method of treating Community-Acquired Bacterial Pneumonia (CABP) in a subject in need of treatment thereof, comprising administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) one or more intravenous doses of about 100 mg each, each administered 24 hours following the immediate preceding intravenous dose, followed by, (3) one oral dose of about 300 mg, administered in the morning and 12-24 hrs after the immediate preceding intravenous dose, followed by, (4) one or more oral doses of about 300 mg each, each administered 24 hours following the immediate preceding oral dose, such that the subject is treated.

A related aspect of the invention provides a method of treating Community-Acquired Bacterial Pneumonia (CABP) in a subject in need of treatment thereof, comprising administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) optionally, one or more intravenous doses of about 100 mg each, each administered 24 hours following the immediate preceding intravenous dose, followed by, (3) optionally, one oral dose of about 300 mg, administered in the morning and 12-24 hrs after the immediate preceding intravenous dose, followed by, (4) optionally, one or more oral doses of about 300 mg each, each administered 24 hours following the immediate preceding oral dose, such that the subject is treated.

A related aspect of the invention provides a method of treating Community-Acquired Bacterial Pneumonia (CABP) in a subject in need of treatment thereof, comprising administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) one or more intravenous doses of about 100 mg each, each administered 24 hours following the immediate preceding intravenous dose, followed by, (3) one or more oral doses of about 300 mg each, each administered 24 hours following the immediate preceding dose, such that said subject is treated.

Another related aspect of the invention provides a method of treating Community-Acquired Bacterial Pneumonia (CABP) in a subject in need of treatment thereof, comprising administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) optionally, one or more intravenous doses of about 100 mg each, each administered 24 hours following the immediate preceding intravenous dose, followed by, (3) one or more oral doses of about 300 mg each, each administered 24 hours following the immediate preceding dose, such that the subject is treated.

In certain embodiments, step (2) consists of one intravenous dose of about 100 mg of the subject 9-[(2,2-dimethyl-propyl amino)-methyl]-minocycline or salt thereof.

Yes another related aspect of the invention provides a method of treating Community-Acquired Bacterial Pneumonia (CABP) in a subject in need of treatment thereof, comprising administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) one or more intravenous doses of about 100 mg each, each administered 24 hours following the immediate preceding intravenous dose, such that the subject is treated.

In certain embodiments, the method steps are completed within 5 days, 6 days, 7 days, 8 days, 9 days, 10 days, 11 days, 12 days, 13 days, 14 days, 15 days, 16 days, 17 days, 18 days, 19 days, 20 days, or 21 days.

In certain embodiments, the steps are completed within 7-14 days, such as 7-10 days, 11-14 days, or 10 days.

In certain embodiments, the number of days of IV dosing is 3-10 days, such as 3-6 days, 7-10 days, or 5 days.

In certain embodiments, the method comprises one or more oral doses, and wherein the number of days of IV dosing is 4-7 days, such as 4-5 days, 6-7 days, or 5 days.

In certain embodiments, the number of days of oral dosing is 1-7 days, such as 1-4 days, 5-7 days, or 5 days.

In certain embodiments, the number of days of IV dosing is 5 days, and the number of days of oral dosing is 5 days.

Another related aspect of the invention provides a method of treating Community-Acquired Bacterial Pneumonia (CABP) in a subject in need of treatment thereof, comprising administering to the subject 9-[(2,2-dimethyl-propyl amino)-methyl]-minocycline or a salt thereof according to the following dosing regimen: (1) three oral doses of about 300-450 mg each, administered 12 hours apart, followed by, (2) optionally, one or more oral doses of about 300-600 mg each, each administered 24 hours following the immediate preceding oral dose, such that the subject is treated.

In certain embodiments, each oral dose is about 300 mg.

In certain embodiments, each oral dose is about 450 mg.

In certain embodiments, each oral dose in step (1) is about 300 mg.

In certain embodiments, each oral dose in step (1) is about 450 mg.

In certain embodiments, each oral dose in step (2) is about 300 mg.

In certain embodiments, each oral dose in step (2) is about 450 mg.

In certain embodiments, each oral dose in step (2) is about 600 mg.

In certain embodiments, the first two oral doses of step (1) are each 300 mg, and the last oral dose of step (1) is about 300, 450, or 600 mg.

In certain embodiments, the first two oral doses of step (1) are each 450 mg, and the last oral dose of step (1) is about 300, 450, or 600 mg.

Another related aspect of the invention provides a method of treating Community-Acquired Bacterial Pneumonia (CABP) in a subject in need of treatment thereof, comprising administering to the subject 9-[(2,2-dimethyl-propyl amino)-methyl]-minocycline or a salt thereof, such that the subject is treated, wherein the 9-[(2,2-dimethyl-propyl amino)-methyl]-minocycline is administered as once-daily oral dose of 300 mg, for 5, 6, 7, or 8 consecutive days.

Another related aspect of the invention provides a method of treating Community-Acquired Bacterial Pneumonia (CABP) in a subject in need of treatment thereof, comprising administering to the subject 9-[(2,2-dimethyl-propyl amino)-methyl]-minocycline or a salt thereof according to the following dosing regimen: (1) one or two once-daily oral dose(s) of about 450-600 mg (administered 24 hrs apart for two once-daily oral doses), followed by, (2) one or more oral doses of about 300-600 mg each, each administered 24 hours following the immediate preceding oral dose, such that the subject is treated.

In certain embodiments, the dosing regimen is: (1) one or two once-daily oral dose(s) of about 450 or 600 mg (administered 24 hrs apart for two once-daily oral doses), followed by, (2) one or more oral doses of about 300 mg each, each administered 24 hours following the immediate preceding oral dose.

In certain embodiments, the dosing regimen is: (1) two once-daily oral doses of about 450 mg, administered 24 hrs apart, followed by, (2) one or more oral doses of about 300 mg each, each administered 24 hours following the immediate preceding oral dose.

In certain embodiments, the steps are completed within 7 days, 8 days, 9 days, 10 days, 11 days, 12 days, 13 days, 14 days, 15 days, 16 days, 17 days, 18 days, 19 days, 20 days, or 21 days.

In certain embodiments, the steps are completed within 7-14 days, within 7-10 days, within 11-14 days, or within 10 days.

In certain embodiments, the CABP is caused by *Staphylococcus aureus* including methicillin-resistant *Staphylococcus aureus* (MRSA), *Streptococcus pneumoniae* including penicillin-resistant *Streptococcus pneumoniae* (PRSP), *Haemophilus influenzae, Moraxella catarrhalis, Klebsiella pneumoniae, Legionella pneumophila, Chlamydophila pneumoniae, Mycoplasma pneumoniae, Chlamydophila psittaci, Coxiella burnetii, Escherichia coli*, or a combination thereof.

In certain embodiments, the *Streptococcus pneumoniae* is penicillin-resistant *Streptococcus pneumoniae* (PRSP), macrolide-resistant *Streptococcus pneumoniae*, cephalosporin-resistant *Streptococcus pneumoniae*, or multidrug-resistant *Streptococcus pneumoniae* (MDRSP).

In certain embodiments, the CABP is caused by intracellular pathogens, such as *Legionella pneumophila, Mycoplasma pneumoniae, Chlamydophila pneumoniae, Chlamydophila psittaci, Coxiella burnetii*, or a combination thereof.

In certain embodiments, the CABP is caused by *Haemophilus parainfluenzae*.

In certain embodiments, the subject is a human.

In certain embodiments, each of said oral dose is administered independently as two 150-mg tablets.

In certain embodiments, each of said intravenous dose is administered continuously over about 30 minutes (e.g., at least 30 minutes and not more than 45 minutes).

In certain embodiments, the dosing regimen has a clinical success rate that is (1) greater than that of moxifloxacin, or (2) within 10% (or 12.5%) margin of non-inferiority compared to moxifloxacin, wherein the moxifloxacin is administered as 400 mg intravenous dose once every 24 hours for three or more days, followed by one or more doses of 400 mg oral doses of moxifloxacin once every 24 hours.

In certain embodiments, the subject experiences improvement, at day 3 to day 5 after step (1), in at least two symptoms selected from: chest pain, frequency or severity of cough, amount of productive sputum, and difficulty breathing, wherein said symptoms are evaluated on a four-point scale of absent, mild, moderate, and severe, and wherein improvement is at least a one-point improvement from baseline to the assessment at said day 3 to day 5 (e.g., from severe to moderate, from moderate to absent, or from mild to absent).

In certain embodiments, the subject, at day 3 to day 5 after step (1), experiences improvement in at least two symptoms and no worsening in any of the symptoms selected from: chest pain, frequency or severity of cough, amount of productive sputum, and difficulty breathing, and improvement in at least one vital sign selected from: body temperature, blood pressure, heart rate, and respiratory rate.

In certain embodiments, the subject undergoes fasting overnight, with no food or drink except water for at least 6 hours, just before step (3) dosing, and wherein the subject continues fasting after step (3) dosing, with no food for 2 hours, and no dairy products for 4 hours.

In certain embodiments, the salt is a tosylate salt.

In certain embodiments, the method has a clinical success rate of about 70%-100%.

In certain embodiments, the clinical success rate is about 75-95%, about 80-95%, about 75-90%, about 80-90%, about 75-85%, about 80-85%, about 85-90%, about 90-95%, about 80-82%, or about 81%.

In certain embodiments, the clinical success rate is about 75-85%, observed at about 72-120 hours after the administration of the first intravenous dose.

In certain embodiments, the clinical success rate is about 80-82%, or 80% or 81%.

In certain embodiments, the clinical success rate is observed at about 5-10 days after the last dose of treatment (e.g., equivalent to a time for post treatment evaluation in clinically evaluable population, or CE-PTE; or in ITT population).

In certain embodiments, the clinical success rate is about 80%, 81%, 82%, 83%, 84%, 85%, 86%, 87%, 88%, 89%, 90%, 91%, 92%, 93%, 94%, 95%, 96%, or 97%.

In certain embodiments, the subject has CABP categorized as PORT Risk Class II.

In certain embodiments, the method has a clinical success rate of about 70-100%, about 75-96%, about 75-90%, about 80-83%, about 82%, about 80-96%, about 90-96%, or about 95%.

In certain embodiments, the clinical success rate is about 75-85%, or about 90-100%, observed at about 5-10 days after the last dose of treatment.

In certain embodiments, the clinical success rate is about 82%, or about 95%.

In certain embodiments, the subject has CABP categorized as PORT Risk Class III.

In certain embodiments, the method has a clinical success rate of about 80-100%, about 85-95%, about 90-95%, about 90-91%, or about 93-94%.

In certain embodiments, the clinical success rate is about 85-100%, observed at about 5-10 days after the last dose of treatment.

In certain embodiments, the clinical success rate is about 90-91%, or about 93-94%.

In certain embodiments, subject has CABP categorized as PORT Risk Class IV.

In certain embodiments, the method has a clinical success rate of about 70-100%, about 75-95%, about 80-95%, about 83-85%, or about 90-91%.

In certain embodiments, the clinical success rate is about 80-95%, observed at about 5-10 days after the last dose of treatment.

In certain embodiments, the clinical success rate is about 83-85%, or about 90-91%.

In certain embodiments, the subject has CABP categorized as PORT Risk Class III or IV.

In certain embodiments, the method has a clinical success rate of about 75-100%, about 85-95%, about 85-90%, about 88-89%, about 90-95%, or about 92-93%.

In certain embodiments, the clinical success rate is about 85-95%, observed at about 5-10 days after the last dose of treatment.

In certain embodiments, the clinical success rate is about 88-89%, or about 92-93%.

In certain embodiments, gastrointestinal (GI) adverse events (AEs) associated with treatment of said subject are mild.

In certain embodiments, GI adverse events (AEs) associated with treatment of said subject do not result in discontinuation of therapy with the method.

In certain embodiments, treatment of the subject (1) does not result in increased risk of *C. difficile* (also known as *C. difficile* colitis and Pseudomembranous colitis) infection in the subject, or (2) does not substantially disrupting gut microbiome in the subject.

In certain embodiments, the subject is at risk of, or is predisposed to, developing a *C. difficile* infection.

In certain embodiments, the subject has recently been treated with one or more antibiotics (such as broad spectrum antibiotics), has had surgery of the gastrointestinal tract, has a disease of the colon (such as an inflammatory bowel disease or colorectal cancer), has a kidney disease, has a weakened immune system; is on chemotherapy, has previously had *C. difficile* infection, is 65 years or older, takes proton-pump inhibitors, or is living in an environment that predisposes said subject to developing *C. difficile* infection (such as in a hospital, a nursing home, or an assisted living facility).

It should be understood that any one embodiment can be combined with any other embodiment unless explicitly disclaimed or improper.

BRIEF DESCRIPTION OF THE DRAWING

FIG. 4 shows clinical success rate at PTE for both Compound 1 (Omadacycline) and Moxifloxacin, by baseline pathogen in the Compound 1 treatment arm with 10 or more isolates. N1=Number of subjects with the specific baseline pathogen. n=Number of subjects in the specific category. Percentages are based on the number of subjects with the specific baseline pathogen.

FIG. 5 shows plasma concentration versus time curves of omadacycline after oral administration. Mean (±SD) plasma concentrations of omadacycline versus time are shown by omadacycline dose (300, 450, or 600 mg) for the pharmacokinetic population. Oral omadacycline doses were administered at time 0 on each of 5 consecutive days of dosing in each of 3 periods. Blood samples were collected for PK analysis on Day 1 (left panel) and Day 5 (right panel). Data was pooled by omadacycline dose for all subjects regardless of the period in which they received a particular dose.

DETAILED DESCRIPTION OF THE INVENTION

Figure 1:
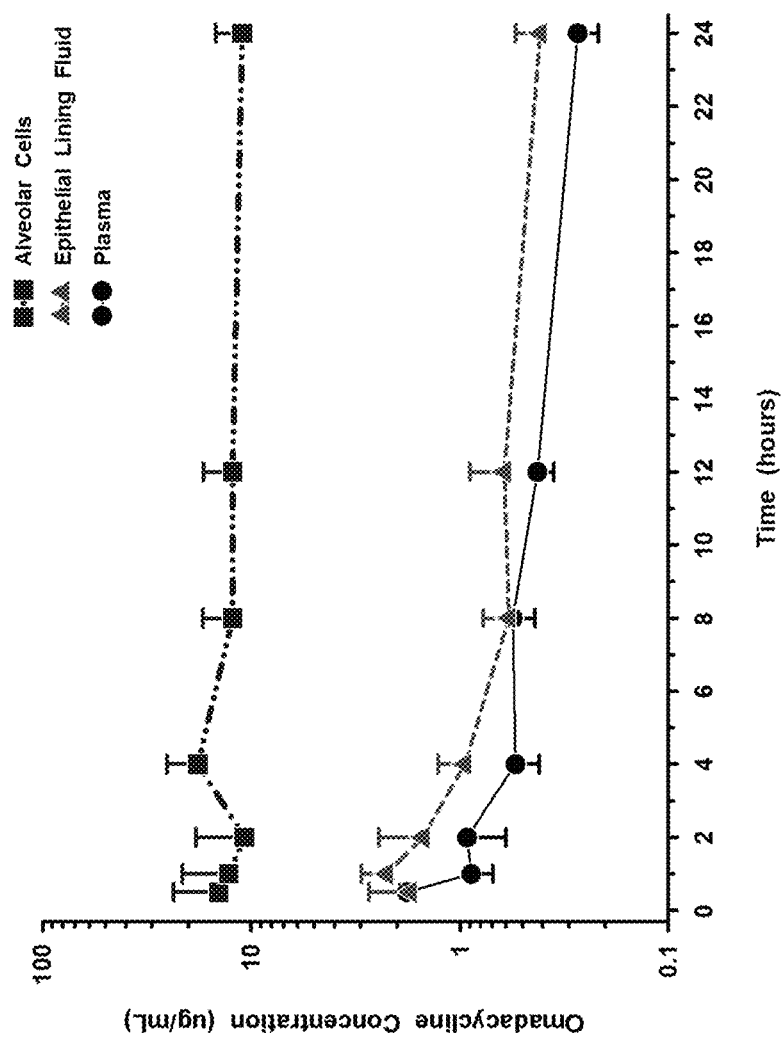
FIG. 1 shows the result of mean Compound 1 (Omadacycline) concentration vs. time profile in AC (Alveolar Cells), plasma, and ELF.

The invention pertains, at least in part, to the discovery that 9-[(2,2-dimethyl-propyl amino)-methyl]-minocycline (Compound 1/Omadacycline) is effective to treat certain bacterial infections, such as CABP, based on a specific dosage and administration regimen.

The invention is further based on the discovery that 9-aminomethyl minocyclines, such as Compound 1, has a relatively broad spectrum against a wide variety of pathogens associated with CABP as further described below.

In addition, 9-aminomethyl minocyclines, such as Compound 1, also has a relatively broad spectrum against intracellular CABP pathogens. The finding that Compound 1 has in vitro activity against common typical and atypical pathogens, and the sustained epithelial lining fluid (ELF) and alveolar cell (AC) including alveolar macrophages (AM) concentrations for 24 hours suggest that Compound 1 has utility as antibacterial agent for the treatment of lower respiratory tract bacterial infections caused by susceptible pathogens, such as intracellular CABP pathogens including *Legionella pneumophila, Mycoplasma pneumoniae, Chlamydophila pneumoniae, Chlamydophila psittaci*, and/or *Coxiella burnetii*.

Thus in one aspect, the invention provides a method of treating CABP in a subject in need of treatment thereof.

In a 1$^{st}$ embodiment, the method comprises administering to the subject 9-[(2,2-dimethyl-propyl amino)-methyl]-minocycline (e.g., as a tosylate salt) according to the following dosing regimen: (1) three intravenous (IV) doses of about 100 mg each, administered 12 hours apart, followed by, (2) one or more IV doses of about 100 mg each, each administered 24 hours following the immediate preceding IV dose, followed by, (3) one oral dose of about 300 mg, administered in the morning and 12-24 hrs after the immediate preceding intravenous dose, followed by, (4) one or more oral doses of about 300 mg each, each administered 24 hours following the immediate preceding oral dose, such that the subject is treated.

In a related, $2^{nd}$ embodiment, the method comprises administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) optionally, one or more intravenous doses of about 100 mg each, each administered 24 hours following the immediate preceding intravenous dose, followed by, (3) optionally, one oral dose of about 300 mg, administered in the morning and 12-24 hrs after the immediate preceding intravenous dose, followed by, (4) optionally, one or more oral doses of about 300 mg each, each administered 24 hours following the immediate preceding oral dose, such that the subject is treated.

In a related, $3^{rd}$ embodiment, the method comprises administering to the subject 9-[(2,2-dimethyl-propyl amino)-methyl]-minocycline or a salt thereof according to the following dosing regimen: (1) three intravenous doses of about 100-125 mg each, administered 12 hours apart, followed by, (2) optionally, one or more intravenous doses of about 100-125 mg each, each administered 24 hours following the immediate preceding intravenous dose, followed by, (3) optionally, one oral dose of about 300-475 mg (i.e., 3 times of the IV dose administered in oral dose), administered in the morning and 12-24 hrs after the immediate preceding intravenous dose, followed by, (4) optionally, one or more oral doses of about 300-475 mg each (i.e., 3 times of the IV dose administered in oral dose), each administered 24 hours following the immediate preceding oral dose, such that the subject is treated. In certain embodiments, the 100-125 mg IV dose is about 100-120 mg, about 100-115 mg, about 100-110 mg, and about 100-105 mg; and the 300-475 mg oral dose is 3 times of the corresponding IV dose (i.e., the 300-475 mg oral dose is about 300-360 mg, about 300-345 mg, about 300-330 mg, and about 300-315 mg, respectively).

In a $4^{th}$ embodiment, the method comprises administering to the subject 9-[(2,2-dimethyl-propyl amino)-methyl]-minocycline (e.g., as a tosylate salt) according to the following dosing regimen: (1) one intravenous (IV) dose of about 200 mg, followed by, (2) optionally, one or more IV doses of about 100 mg each, each administered 24 hours following the immediate preceding IV dose, followed by, (3) optionally, one oral dose of about 300 mg, administered in the morning and 12-24 hrs after the immediate preceding intravenous dose, followed by, (4) one or more oral doses of about 300 mg each, each administered 24 hours following the immediate preceding oral dose, such that the subject is treated.

In a $5^{th}$ embodiment, the method comprises administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) one or more intravenous doses of about 100 mg each, each administered 24 hours following the immediate preceding intravenous dose, followed by, (3) one or more oral doses of about 300 mg each, each administered 24 hours following the immediate preceding dose, such that the subject is treated.

In a related $6^{th}$ embodiment, the method comprises administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) optionally, one or more intravenous doses of about 100 mg each, each administered 24 hours following the immediate preceding intravenous dose, followed by, (3) one or more oral doses of about 300 mg each, each administered 24 hours following the immediate preceding dose, such that the subject is treated.

In a related $7^{th}$ embodiment, the method comprises administering to the subject 9-[(2,2-dimethyl-propyl amino)-methyl]-minocycline or a salt thereof according to the following dosing regimen: (1) three intravenous doses of about 100-125 mg each, administered 12 hours apart, followed by, (2) optionally, one or more intravenous doses of about 100-125 mg each, each administered 24 hours following the immediate preceding intravenous dose, followed by, (3) one or more oral doses of about 300-475 mg (i.e., 3 times of the IV dose administered in oral dose) each, each administered 24 hours following the immediate preceding dose, such that the subject is treated. In certain embodiments, the 100-125 mg IV dose is about 100-120 mg, about 100-115 mg, about 100-110 mg, and about 100-105 mg; and the 300-475 mg oral dose is 3 times of the corresponding IV dose (i.e., the 300-475 mg oral dose is about 300-360 mg, about 300-345 mg, about 300-330 mg, and about 300-315 mg, respectively).

In an $8^{th}$ embodiment, the method comprises administering to the subject 9-[(2,2-dimethyl-propyl amino)-methyl]-minocycline or a salt thereof according to the following dosing regimen: (1) one intravenous dose of about 200 mg, followed by, (2) optionally, one or more intravenous doses of about 100 mg each, each administered 24 hours following the immediate preceding intravenous dose, followed by, (3) optionally, one or more oral doses of about 300 mg each, each administered 24 hours following the immediate preceding dose, such that the subject is treated.

In a $9^{th}$ embodiment, step (2) in the method of any one of the $5^{th}$ to the $8^{th}$ embodiments consists of one intravenous dose of about 100 mg of the subject 9-[(2,2-dimethyl-propyl amino)-methyl]-minocycline or salt thereof.

In a $10^{th}$ embodiment, the method comprises administering to the subject 9-[(2,2-dimethyl-propyl amino)-methyl]-minocycline or a salt thereof according to the following dosing regimen: (1) three intravenous doses of about 100 mg each, administered 12 hours apart, followed by, (2) one or more intravenous doses of about 100 mg each, each administered 24 hours following the immediate preceding intravenous dose, such that said subject is treated.

In a related $11^{th}$ embodiment, the method comprises administering to the subject 9-[(2,2-dimethyl-propyl amino)-methyl]-minocycline or a salt thereof according to the following dosing regimen: (1) three intravenous doses of about 100-125 mg each, administered 12 hours apart, followed by, (2) one or more intravenous doses of about 100-125 mg each, each administered 24 hours following the immediate preceding intravenous dose, such that said subject is treated. In certain embodiments, the 100-125 mg IV dose is about 100-120 mg, about 100-115 mg, about 100-110 mg, and about 100-105 mg.

In a related $12^{th}$ embodiment, the method comprises administering to the subject 9-[(2,2-dimethyl-propyl amino)-methyl]-minocycline or a salt thereof according to the following dosing regimen: (1) one intravenous dose of about 200 mg, followed by, (2) one or more intravenous doses of about 100 mg each, each administered 24 hours following the immediate preceding intravenous dose, such that said subject is treated.

In a $13^{th}$ embodiment, the method steps of any one of the $1^{st}$-$12^{th}$ embodiments are completed within 5 days, 6 days, 7 days, 8 days, 9 days, 10 days, 11 days, 12 days, 13 days, 14 days, 15 days, 16 days, 17 days, 18 days, 19 days, 20 days, or 21 days. In certain related embodiments, the method steps are completed within 7 days, 8 days, 9 days, 10 days, 11 days, 12 days, 13 days, 14 days, 15 days, 16 days, 17 days, 18 days, 19 days, or 20 days. In yet another embodiment, the method steps are completed within 5 days, 6 days, or 21 days. In certain related embodiments, the method steps are completed within 5 or 6 days. In certain related embodiments, the method steps are completed within 7-14 days.

In a $14^{th}$ embodiment, the method steps of any one of the $1^{st}$-$12^{th}$ embodiments are completed within 7-14 days, such as 7-10 days, 11-14 days, or 10 days.

In a $15^{th}$ embodiment, the number of days of IV dosing in the $14^{th}$ embodiment is 3-10 days, such as 3-6 days, 7-10 days, or 5 days.

In a $16^{th}$ embodiment, the method of any one of the $1^{st}$-$15^{th}$ embodiments comprise one or more oral doses, and wherein the number of days of IV dosing is 4-7 days, such as 4-5 days, 6-7 days, or 5 days.

In a $17^{th}$ embodiment, the number of days of oral dosing in the $16^{th}$ embodiment is 1-7 days, such as 1-4 days, 5-7 days, or 5 days.

In an $18^{th}$ embodiment, the number of days of IV dosing in any one of the $1^{st}$-$17^{th}$ embodiments is 5 days, and the number of days of oral dosing is 5 days.

In a $19^{th}$ embodiment, the method comprises administering to the subject 9-[(2,2-dimethyl-propyl amino)-methyl]-minocycline (e.g., as a tosylate salt) according to the following dosing regimen: (1) three oral doses of about 300-450 mg (such as 300 mg or 450 mg) each, administered 12 hours apart, followed by, (2) optionally, one or more oral doses of about 300-600 mg (such as 300 mg, 450 mg, or 600 mg) each, each administered 24 hours following the immediate preceding oral dose, such that the subject is treated.

In a $20^{th}$ embodiment, each oral dose of the $19^{th}$ embodiment is about 300 mg.

In a $21^{st}$ embodiment, each oral dose of the $19^{th}$ embodiment is about 450 mg.

In a $22^{nd}$ embodiment, each oral dose in step (1) of the $19^{th}$ embodiment is about 300 mg.

In a $23^{rd}$ embodiment, each oral dose in step (1) of the $19^{th}$ embodiment is about 450 mg.

In a $24^{th}$ embodiment, each oral dose in step (2) of the $19^{th}$, $22^{nd}$, or $23^{rd}$ embodiment is about 300 mg.

In a $25^{th}$ embodiment, each oral dose in step (2) of the $19^{th}$, $22^{nd}$, or $23^{rd}$ embodiment is about 450 mg.

In a $26^{th}$ embodiment, each oral dose in step (2) of the $19^{th}$, $22^{nd}$, or $23^{rd}$ embodiment is about 600 mg.

In a $27^{th}$ embodiment, the first two oral doses of step (1) of the $19^{th}$ embodiment are each 300 mg, and the last oral dose of step (1) is about 300, 450, or 600 mg.

In a $28^{th}$ embodiment, the first two oral doses of step (1) of the $19^{th}$ embodiment are each 450 mg, and the last oral dose of step (1) is about 300, 450, or 600 mg.

In a $29^{th}$ embodiment, the method comprises administering to the subject 9-[(2,2-dimethyl-propyl amino)-methyl]-minocycline (e.g., as a tosylate salt) according to the following dosing regimen: (1) one or two once-daily oral dose(s) of about 450-600 mg (such as 450 mg, or 600 mg) (administered 24 hrs apart for two once-daily oral doses), followed by, (2) one or more oral doses of about 300-600 mg (such as 300 mg, 450 mg, or 600 mg) each, each administered 24 hours following the immediate preceding oral dose, such that the subject is treated.

In a $30^{th}$ embodiment, the method comprises administering to the subject 9-[(2,2-dimethyl-propyl amino)-methyl]-minocycline (e.g., as a tosylate salt) according to the following dosing regimen: (1) one or two once-daily oral dose(s) of about 300-600 mg (such as 300 mg, 450 mg, or 600 mg) (administered 24 hrs apart for two once-daily oral doses), followed by, (2) one or more oral doses of about 300-600 mg (such as 300 mg, 450 mg, or 600 mg) each, each administered 24 hours following the immediate preceding oral dose, such that the subject is treated.

In a $31^{st}$ embodiment, the method comprises administering to the subject 9-[(2,2-dimethyl-propyl amino)-methyl]-minocycline or a salt thereof, such that the subject is treated, wherein the 9-[(2,2-dimethyl-propyl amino)-methyl]-minocycline is administered as once-daily oral dose of 300 mg, for 5, 6, 7, or 8 consecutive days.

In a $32^{nd}$ embodiment, the dosing regimen of the $29^{th}$ embodiment is: (1) one or two once-daily oral dose(s) of about 450-600 mg, such as 450 mg or 600 mg, (administered 24 hrs apart for two once-daily oral doses), followed by, (2) one or more oral doses of about 300 mg each, each administered 24 hours following the immediate preceding oral dose.

In a $33^{rd}$ embodiment, the dosing regimen of the $29^{th}$ embodiment is: (1) two once-daily oral doses of about 450 mg, administered 24 hrs apart, followed by, (2) one or more oral doses of about 300 mg each, each administered 24 hours following the immediate preceding oral dose.

In a $34^{th}$ embodiment, the dosing regimen of the $29^{th}$ embodiment is: (1) two once-daily oral doses of about 600 mg, administered 24 hrs apart, followed by, (2) one or more oral doses of about 300 mg each, each administered 24 hours following the immediate preceding oral dose.

In a $35^{th}$ embodiment, the steps of any one of the $25^{th}$-$34^{th}$ embodiments are completed within 7 days, 8 days, 9 days, 10 days, 11 days, 12 days, 13 days, 14 days, 15 days, 16 days, 17 days, 18 days, 19 days, 20 days, or 21 days.

In a $36^{th}$ embodiment, the steps of any one of the $25^{th}$-$34^{th}$ embodiments are completed within 7-14 days, within 7-10 days, within 11-14 days, or within 10 days.

In a $37^{th}$ embodiment, the CABP of any one of the $1^{st}$-$36^{th}$ embodiments is caused by *Staphylococcus aureus* including methicillin-resistant *Staphylococcus aureus* (MRSA), *Streptococcus pneumoniae* including penicillin-resistant *Streptococcus pneumoniae* (PRSP), *Haemophilus influenzae*, *Moraxella catarrhalis*, *Klebsiella pneumoniae*, *Legionella pneumophila*, *Chlamydophila pneumoniae*, *Mycoplasma pneumoniae*, *Chlamydophila psittaci*, *Coxiella burnetii*, *Escherichia coli*, or a combination thereof.

In a $38^{th}$ embodiment, the *Streptococcus pneumoniae* of the $37^{th}$ embodiment is penicillin-resistant *Streptococcus pneumoniae* (PRSP), macrolide-resistant *Streptococcus pneumoniae*, cephalosporin-resistant *Streptococcus pneumoniae*, or multidrug-resistant *Streptococcus pneumoniae* (MDRSP).

In a $39^{th}$ embodiment, the CABP of any one of the $1^{st}$-$36^{th}$ embodiments is caused by intracellular pathogens, such as *Legionella pneumophila*, *Mycoplasma pneumoniae*, *Chlamydophila pneumoniae*, *Chlamydophila psittaci*, *Coxiella burnetii*, or a combination thereof.

In a $40^{th}$ embodiment, the CABP of any one of the $1^{st}$-$36^{th}$ embodiments is caused by *Haemophilus parainfluenzae*.

In a $41^{st}$ embodiment, the subject of any of the $1^{st}$-$40^{th}$ embodiments is a human.

In a $42^{nd}$ embodiment, each of the oral dose of any of the $1^{st}$-$41^{st}$ embodiments is administered independently as two 150-mg tablets.

In a 43$^{rd}$ embodiment, each of the intravenous dose of any of the 1$^{st}$-42$^{nd}$ embodiments is administered continuously over about 30 minutes (e.g., at least 30 minutes and not more than 45 minutes).

In a 44$^{th}$ embodiment, the dosing regimen of any of the 1$^{st}$-43$^{rd}$ embodiments has a clinical success rate that is within 10% (or 12.5%) margin of non-inferiority compared to moxifloxacin administered as 400 mg intravenous dose once every 24 hours for three or more days, followed by one or more doses of 400 mg oral doses of moxifloxacin once every 24 hours.

In a 45$^{th}$ embodiment, the subject of any of the 1$^{st}$-44$^{th}$ embodiments: (1) has at least 3 of the symptoms selected from: cough, production of purulent sputum, dyspnea (shortness of breath), and pleuritic chest pain; (2) has at least two abnormal vital signs selected from: fever or hypothermia (temperature >38.0° C. [100.4° F.] or <36.0° C. [95.5° F.]), hypotension with systolic blood pressure (SBP) <90 mm Hg, tachycardia (heart rate >90 beats per minute (bpm)), and tachypnea (respiratory rate (RR) >20 breaths/minute); (3) has at least one clinical sign or laboratory finding associated with CABP: hypoxemia (partial pressure of arterial oxygen [PaO$_2$]<60 mm Hg by arterial blood gas [ABG] or oxygen saturation <90% by pulse oximetry), clinical evidence (e.g., by physical examination findings) of pulmonary consolidation (e.g., dullness on percussion, bronchial breath sounds, or egophony), and an elevated total white blood cell (WBC) count (>12,000 cells/mm$^3$) or leucopenia (WBC <4,000 cells/mm$^3$) or elevated immature neutrophils (>15% band forms, regardless of total peripheral WBC count); (4) has radiographically-confirmed pneumonia (i.e., new or progressive pulmonary infiltrate(s) in a lobar or a multilobar distribution on chest X-ray (CXR) or chest computed tomography (CT) scan consistent with acute bacterial pneumonia within 24 or 48 hours prior to step (1)); and (5) has disease categorized as being PORT Risk Class II, III, or IV, or has appropriate sputum specimen characterized by fewer than 10 squamous epithelial cells and more than 25 polymorphonuclear cells per low power field.

In a 46$^{th}$ embodiment, the subject of any of the 1$^{st}$-44$^{th}$ embodiments experience improvement, at day 3 to day 5 after step (1), in at least two symptoms selected from: chest pain, frequency or severity of cough, amount of productive sputum, and difficulty breathing, wherein the symptoms are evaluated on a four-point scale of absent, mild, moderate, and severe, and wherein improvement is at least a one-point improvement from baseline to the assessment at the day 3 to day 5 (e.g., from severe to moderate, from moderate to absent, or from mild to absent).

In a 47$^{th}$ embodiment, the subject of any of the 1$^{st}$-46$^{th}$ embodiments, at day 3 to day 5 after step (1), experience improvement in at least two symptoms and no worsening in any of the symptoms selected from: chest pain, frequency or severity of cough, amount of productive sputum, and difficulty breathing, and improvement in at least one vital sign selected from: body temperature, blood pressure, heart rate, and respiratory rate.

Compound 1 was found to have a significant food effect, in that food consumption has a significant impact on the oral bioavailability of orally administered 300 mg dose of Compound 1. See Example 3. A PK study in healthy volunteers showed that, compared with a fasted dose, bioavailability was reduced by 15% to 17% for a nondairy meal 4 hours before dosing, 40% to 42% for a nondairy meal 2 hours before dosing, and 59% to 63% for a dairy meal 2 hours before dosing. Thus, the effect of food was more pronounced when a high-fat meal was consumed closer to dosing and when dairy was included in the meal. Based on this result, oral Compound 1 should be administered at least 6 hours following a meal in order to achieve maximum bioavailability for the oral dose designed to achieve therapeutic efficacy.

Thus in a 48$^{th}$ embodiment, the subject of any one of the first-47$^{th}$ embodiments undergoes fasting overnight, with no food or drink except water for at least 6 hours, just before step (3) dosing, and wherein the subject continues fasting after step (3) dosing, with no food for 2 hours, and no dairy products for 4 hours.

In a 49$^{th}$ embodiment, the salt of any one of the 1$^{st}$-48$^{th}$ embodiments is a tosylate salt.

In a 50$^{th}$ embodiment, the method of any one of the 1$^{st}$-49$^{th}$ embodiments has a clinical success rate of about 70%-100%.

In a 51$^{st}$ embodiment, the clinical success rate of the 50$^{th}$ embodiment is about 75-95%, about 80-95%, about 75-90%, about 80-90%, about 75-85%, about 80-85%, about 85-90%, about 90-95%, about 80-82%, or about 81%.

In a 52$^{nd}$ embodiment, the clinical success rate of the 51$^{st}$ embodiment is about 75-85%, observed at about 72-120 hours after the administration of the first intravenous dose.

In a 53$^{rd}$ embodiment, the clinical success rate of the 52$^{nd}$ embodiment is about 80-82%, or 80% or 81%.

In a 54$^{th}$ embodiment, the clinical success rate of the 51$^{st}$ embodiment is observed at about 5-10 days after the last dose of treatment (e.g., equivalent to a time for post treatment evaluation in clinically evaluable population, or CE-PTE; or in ITT population).

In a 55$^{th}$ embodiment, the clinical success rate of the 54$^{th}$ embodiment is about 80%, 81%, 82%, 83%, 84%, 85%, 86%, 87%, 88%, 89%, 90%, 91%, 92%, 93%, 94%, 95%, 96%, or 97%.

In a 56$^{th}$ embodiment, the subject of any one of the 1$^{st}$-55$^{th}$ embodiments has CABP categorized as PORT Risk Class II.

In a 57$^{th}$ embodiment, the method of the 56$^{th}$ embodiment has a clinical success rate of about 70-100%, about 75-96%, about 75-90%, about 80-83%, about 82%, about 80-96%, about 90-96%, or about 95%.

In a 58$^{th}$ embodiment, the clinical success rate of the 57$^{th}$ embodiment is about 75-85%, or about 90-100%, observed at about 5-10 days after the last dose of treatment.

In a 59$^{th}$ embodiment, the clinical success rate of the 58$^{th}$ embodiment is about 82%, or about 95%.

In a 60$^{th}$ embodiment, the subject of and one of the 1$^{st}$-55$^{th}$ embodiments has CABP categorized as PORT Risk Class III.

In a 61$^{st}$ embodiment, the method of any one of the 1$^{st}$-60$^{th}$ embodiments has a clinical success rate of about 80-100%, about 85-95%, about 90-95%, about 90-91%, or about 93-94%.

In a 62$^{nd}$ embodiment, the clinical success rate of the 61$^{st}$ embodiment is about 85-100%, observed at about 5-10 days after the last dose of treatment.

In a 63$^{rd}$ embodiment, the clinical success rate of the 62$^{nd}$ embodiment is about 90-91%, or about 93-94%.

In a 64$^{th}$ embodiment, the subject of any one of the 1$^{st}$-55$^{th}$ embodiments has CABP categorized as PORT Risk Class IV.

In a 65$^{th}$ embodiment, the method of the 64$^{th}$ embodiment has a clinical success rate of about 70-100%, about 75-95%, about 80-95%, about 83-85%, or about 90-91%.

In a 66$^{th}$ embodiment, the clinical success rate of the 65$^{th}$ embodiment is about 80-95%, observed at about 5-10 days after the last dose of treatment.

In a 67th embodiment, the clinical success rate of the 66th embodiment is about 83-85%, or about 90-91%.

In a 68th embodiment, the subject of any one of the 1st-55th embodiments has CABP categorized as PORT Risk Class III or IV.

In a 69th embodiment, the method of the 68th embodiment has a clinical success rate of about 75-100%, about 85-95%, about 85-90%, about 88-89%, about 90-95%, or about 92-93%.

In a 70th embodiment, the clinical success rate of the 69th embodiment is about 85-95%, observed at about 5-10 days after the last dose of treatment.

In a 71st embodiment, the clinical success rate of the 70th embodiment is about 88-89%, or about 92-93%.

In a 72nd embodiment, gastrointestinal (GI) adverse events (AEs) associated with treatment of the subject in method of any one of the 1st-71st embodiments are mild.

In a 73rd embodiment, GI adverse events (AEs) associated with treatment of the subject in method of any one of the 1st-71st embodiments do not result in discontinuation of therapy with the method.

In a 74th embodiment, treatment of the subject in the method of any one of the 1st-73rd embodiments (1) does not result in increased risk of *C. difficile* (also known as *C. difficile* colitis and Pseudomembranous colitis) infection in the subject, or (2) does not substantially disrupting gut microbiome in the subject.

In a 75th embodiment, the subject of the 74th embodiment is at risk of, or is predisposed to, developing a *C. difficile* infection.

In a 76th embodiment, the subject of the 75th embodiment has recently been treated with one or more antibiotics (such as broad spectrum antibiotics), has had surgery of the gastrointestinal tract, has a disease of the colon (such as an inflammatory bowel disease or colorectal cancer), has a kidney disease, has a weakened immune system; is on chemotherapy, has previously had *C. difficile* infection, is 65 years or older, takes proton-pump inhibitors, or is living in an environment that predisposes the subject to developing *C. difficile* infection (such as in a hospital, a nursing home, or an assisted living facility).

In a 77th embodiment, in any of the preceding methods, GI adverse events (AEs) associated with treatment of the subject do not result in discontinuation of therapy with the method, and treatment of the subject (1) does not result in increased risk of *C. difficile* (e.g., *C. difficile* colitis and Pseudomembranous colitis) infection in the subject or (2) does not substantially disrupting gut microbiome in the subject.

As used herein, the term "subject" may include animals (e.g., non-human mammal) capable of suffering from a bacterial infection. Examples of subjects include animals such as farm animals (e.g., cows, pigs, horses, goats, rabbits, sheep, etc.), lab animals (mice, rats, etc.), pets (e.g., dogs, cats, ferrets, etc.), and primates (e.g., humans and non-human primates such as monkeys, gorillas, chimpanzees, etc.).

In any of the above embodiments, the subject may be a human, a non-human primate, or a non-human mammal.

The term "treating" or "treatment" refers to the amelioration, eradication, or diminishment of one or more symptoms of the disorder, e.g., a bacterial infection, to be treated. In certain embodiments, the disorder term includes the eradication of bacteria associated with the infection to be treated.

The term "prophylaxis" means to prevent or reduce the risk of bacterial infection.

The term "resistance" or "resistant" refers to the antibiotic/organism standards as defined by the Clinical and Laboratories Standards Institute (CLSI) and/or the Food and Drug Administration (FDA).

In certain embodiments, the infection may be resistant to other antibiotics, such as penicillin or tetracycline.

The term "effective amount" includes the amount of the tetracycline compound (e.g., Compound 1) needed to treat a bacterial infection (e.g., CABP). For example, an effective amount describes an efficacious level sufficient to achieve the desired therapeutic effect through the killing of bacteria and/or inhibition of bacterial growth. Preferably, the bacterial infection is treated when the pathogen (e.g., bacteria) is eradicated. The bacterial infection is also treated when at least one symptom of infection is reduced, alleviated, or eliminated.

The term "evaluable clinical success" refers to a clinical trial participant who: (1) did not meet any criteria for evaluable clinical failure; (2) did not receive potentially effective non-study antibiotics for any other reason; and (3) the blinded evaluator indicated at the test of cure evaluation that the infection had sufficiently resolved such that antibiotics were not needed.

The term "evaluable clinical failure" refers to a clinical trial participant who met any one of the following criteria: the blinded evaluator discontinued study drug and indicated that the infection had responded inadequately such that alternative antibiotic(s) were needed; the blinded evaluator discontinued study drug because of an adverse event that was assessed as probably or possibly drug-related; the primary site of infection was surgically removed; or the subject had no evaluation after the end of intravenous or oral treatment.

The term "clinical success rate" refers to the number of evaluable clinical successes divided by the total number of population in the trial.

The term "microbiologically evaluable clinical success rate" refers to those who met the definition of evaluable clinical success and had an infecting pathogen at baseline.

In one embodiment, the effective amount of the tetracycline compound, e.g. 9-[(2,2-dimethyl-propyl amino)-methyl]-minocycline, when administered orally is from about 150 to about 600 mg, about 150 to about 450 mg, from about 150 to about 300 mg, or about 300 mg.

In certain embodiments, each oral dose is administered as multiples of 150 mg doses (e.g., 150 mg, 2×150 mg, 3×150 mg, or 4×150 mg). For example, a 300 mg oral dose may consists of two 150 mg tablets/pills/capsules/gels, etc.

In another embodiment, the effective amount of the tetracycline compound, e.g., 9-[(2,2-dimethyl-propyl amino)-methyl]-minocycline, when administered intravenously (IV) is from about 50 to about 200 mg, from about 50 to about 150 mg, from about 50 to about 100 mg, or about 100 mg, or about 200 mg.

The compound, either in IV formulation or in oral formulation, may be administered as a salt (e.g., tosylate salt or hydrochloride salt) or as a free base. For example, any salt or a polymorph of a salt, such as a tosylate salt of Compound 1, as described in U.S. Pat. No. 8,383,610 (incorporated herein by reference), may be used in the instant invention. In addition, any formulation, such as oral formulation in tablet form, as described in U.S. Pat. No. 9,314,475 (incorporated herein by reference), may be used in the instant invention.

It is to be understood that wherever values and ranges are provided herein, e.g., in ages of subject populations, dosages, and blood levels, all values and ranges encompassed by these values and ranges, including recited upper and/or lower limits of the ranges, are meant to be encompassed within the scope of the present invention. Moreover, all values in these values and ranges may also be the upper or lower limits of a range.

In another embodiment, the tetracycline compound (e.g., Compound 1) may be administered once or twice per day, either intravenously or orally. In certain embodiments, twice per day administration has two equal doses.

In certain embodiments, the 9-[(2,2-dimethyl-propyl amino)-methyl]-minocycline has a microbiologically evaluable clinical success rate of greater than about 60%. In certain embodiments, the compound of the invention has a clinical success rate of greater than about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 93.7%, 94%, 95%, 96%, 97%, 97.5%, 98%, 99% or more, either in the intent to treat (ITT) patient population or in the clinically evaluable (CE) patient population.

As used herein, an "Intent-to-Treat (or ITT)" population refers to all enrolled clinical trial subjects. In certain embodiments, the ITT population is further limited to all enrolled clinical trial subjects who have received at least one dose of the study drug (e.g., Compound 1). A "Clinically Evaluable (or CE)" population refers to all ITT subjects who had a qualifying infection as defined by the relevant clinical protocol, e.g., those with CABP. "Clinical success" refers to the continued improvement or complete resolution of baseline symptoms in the ITT or CE populations, assessed by the clinical investigator, at a set period (e.g., 10 to 17 days) after the last dose of the study drug.

In one example, a subject is treated intravenously followed by an oral step down. In certain embodiments, the subject is treated directly by oral dose without any preceding IV dose.

In certain embodiments, the present invention provides a method of treating a subject for an infection (e.g., CABP), comprising administering to the subject an effective amount of Compound 1 or a salt thereof wherein the subject is initially treated about 1, 2, 3, 4, or 5 days intravenously, followed by about 2, 3, 4, 5, 6, 7, 8, 9, 10, 11, 12, 13, 14, or 15 days of oral treatment, such that the subject is treated. In certain embodiments, the first day of IV treatment consists of a higher loading dose (e.g., 2× dose, or 2×100 mg doses). In certain embodiments, each IV dose from day 2 and beyond is administered about 24 hrs from the immediate preceding IV dose. In certain embodiments, the total treatment period is about 3, 4, 5, 6, 7, 8, 9, 10, 11, 12, 13, 14, or 15 days. In certain embodiments, one (e.g., the $2^{nd}$ IV loading dose) or both of the IV loading doses is replaced by a 300 mg or 450 mg oral dose.

In another embodiment, the present invention provides a method of treating a subject for an infection (e.g., CABP), comprising administering to said subject an effective amount of Compound 1 or a salt thereof wherein the subject initially treated intravenously has elevated compound 1 blood levels followed by reduced Compound 1 blood levels with oral treatment, such that the subject is treated. In certain embodiments, the initially elevated compound 1 blood level is achieved by a higher (e.g., 2×) loading dose(s), such as 2 IV loading doses of about 100 mg each.

Pharmaceutical Compositions of the Invention

The invention also utilizes or pertains to pharmaceutical compositions comprising a therapeutically effective amount of a tetracycline compound (e.g., a 9-aminomethyl tetracycline compound, e.g., 9-[(2,2-dimethyl-propyl amino)-methyl]-minocycline) or a salt thereof and, optionally, a pharmaceutically acceptable carrier.

In a further embodiment, the invention pertains to a pharmaceutical composition comprising from about 100 to about 700 mg (e.g., about 300, 450, or 600 mg) of 9-[(2,2-dimethyl-propyl amino)-methyl]-minocycline or a salt thereof and a pharmaceutically acceptable carrier. In a further embodiment, the pharmaceutically acceptable carrier is acceptable for oral administration. In another further embodiment, the tetracycline compound is a free base or a tosylate salt.

In yet another further embodiment, the composition comprises from about 110 to about 490 mg, from about 120 to about 480 mg, from about 130 to about 470 mg, from about 140 to about 460 mg, from about 150 to about 450 mg, from about 160 to about 440 mg, from about 170 mg to about 430 mg, from about 180 mg to about 420 mg, from about 190 mg to about 410 mg, from about 200 mg to about 400 mg, from about 210 mg to about 390 mg, from about 220 mg to about 380 mg, from about 230 mg to about 370 mg, from about 240 mg to about 360 mg, from about 250 mg to about 350 mg, from about 260 mg to about 340 mg, from about 270 mg to about 330 mg, from about 280 mg to about 320 mg, from about 290 mg to about 310 mg, or about 300 mg of 9-[(2,2-dimethyl-propyl amino)-methyl]-minocycline. Optionally, the pharmaceutically acceptable carrier is suitable for oral administration.

In another embodiment, the invention also pertains to a pharmaceutical composition comprising from about 50 to about 250 mg (e.g., about 100 mg) of 9-[(2,2-dimethyl-propylamino)-methyl]-minocycline or a salt thereof (e.g., a hydrochloride salt) and a pharmaceutically acceptable carrier suitable for intravenous administration.

In yet another further embodiment, the composition comprises from about 100 to about 300 mg, from about 125 to about 275 mg, from about 150 mg to about 250 mg, from about 100 mg to about 200 mg, about 100 mg, or about 200 mg of IV or oral 9-[(2,2-dimethyl-propyl amino)-methyl]-minocycline.

The language "pharmaceutically acceptable carrier" includes substances capable of being co-administered with the tetracycline compound of the invention, e.g., 9-[(2,2-dimethyl-propyl amino)-methyl]-minocycline, and which allow the tetracycline compound to perform its intended function, e.g., treat or prevent a bacterial infection. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention (e.g., Compound 1) that are basic in nature are capable of forming a wide variety of salts with various inorganic and organic acids. The acids that may be used to prepare pharmaceutically acceptable acid addition salts of the minocycline compounds of the invention that are basic in nature are those that form nontoxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a minocycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. Preferably, the tetracycline compound of the invention is administered as a tosylate (e.g., p-toluenesulfonate) salt or as a freebase orally or as a hydrochloride salt intravenously.

The tetracycline compounds of the invention (e.g., Compound 1) and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutic compositions known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective tetracycline compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

EXEMPLIFICATION OF THE INVENTION

Example 1 An Open-Label, Parallel Group, Multiple IV Dose Study to Assess Intra-Pulmonary Steady-State Concentrations of Compound 1 and Tigecycline in Healthy Adult Subjects To be effective in lower respiratory tract infections (RTI), an antibiotic must attain adequate concentrations in respiratory tissue to affect respiratory pathogens. Both extracellular and intracellular pathogens may cause infection, and therefore extracellular and intracellular concentrations of antibiotics must be adequate to cover all of the pathogens. The concentration of antibiotic in bronchial mucosa provides a reliable guide to bronchial penetration of the drug and may be a better predictor of clinical efficacy than serum levels for treatment of bronchitis and bronchopneumonia.

Epithelial lining fluid (ELF) and alveolar cells (AC), including mostly alveolar macrophages (AM), have been advocated as important infection sites for common extracellular and intracellular pathogens, respectively. Direct measurement of the concentration of antimicrobial agents in the ELF allows for a more informed approach to appropriate dosing of the agent for RTI, and to evaluate the pharmacokinetic (PK) and exposure-response targets of the drug for respiratory tract infections. Bronchoalveolar lavage (BAL) to collect respiratory tract fluid and tissue has become a standard method of ascertaining both extracellular and intracellular antibiotic concentrations after systemic administration of the antibiotic. Extracellular concentrations are calculated from fluid reflecting ELF, and intracellular concentrations are measured in ACs, including macrophages.

This study was designed to determine intra-pulmonary PK of Compound 1 in healthy subjects; currently there is no information on the concentration of Compound 1 in pulmonary compartments in humans.

Compound 1 has been shown to have in vitro activity against the most common typical and atypical causes of community-acquired bacterial pneumonia (CABP) and is being developed for the treatment of CABP. It is very active in vitro against most Gram-positive pathogens. It also exhibits activity against atypical pathogens (e.g., *Legionella* species (spp.), *Chlamydophila* spp.), and some anaerobic and Gram-negative pathogens. The drug is active against strains expressing both mechanisms of tetracycline resistance, as well as strains that are resistant to currently available antibiotics, including methicillin, vancomycin, erythromycin, and ciprofloxacin. The in vitro activity of Compound 1 was not affected by serum or lung surfactant, an important characteristic that is consistent with potential utility in infections involving the lower respiratory tract. Further, it has been shown to be effective in mouse models of lower respiratory tract infections caused by *Streptococcus pneumoniae* and *Haemophilus influenzae*. In mice, Compound 1 concentrations in lung tissue exceed plasma concentrations by 3.7 to 4.4 fold. In vitro results against intracellular bacteria and tissue culture experiments indicate that Compound 1 concentrates within mammalian cells.

Tigecycline has a similar PK profile to Compound 1, and with its documented concentration levels achieved in human ELF, the inclusion of tigecycline is intended to provide assay sensitivity in the study.

Compound 1 has been developed for both iv and oral administration and has been well characterized in 16 Phase 1 studies including 536 subjects exposed to Compound 1. In addition, Compound 1 was evaluated in a Phase 2 study of 219 subjects with complicated skin and skin structure infection (cSSSI) and a sponsor-terminated Phase 3 study that enrolled 143 subjects with cSSSI. Compound 1 was well-tolerated and demonstrated efficacy similar to an established comparator (linezolid).

The purpose of the study was to determine the concentration of Compound 1 in pulmonary compartments (ELF and in pulmonary ACs, including AMs) and define time course of pulmonary distribution in comparison with the plasma pharmacokinetic (PK) profile. Compound 1 was administered intravenously to healthy subjects for 4 days (5 doses) to steady-state systemic concentrations. Subjects were grouped to have BAL at set times after the last dose of drug. Concomitant blood samples were taken to compare tissue with serum antibiotic concentrations.

The data obtained in this study, namely the in vitro activity against common typical and atypical pathogens and the sustained ELF and AC (mostly AM) concentrations for 24 hours suggest that Compound 1 has the potential to be a useful antibacterial agent for the treatment of lower respiratory tract bacterial infections caused by susceptible pathogens.

Tigecycline has a similar PK profile to Compound 1, and with its ability to achieve concentrations in ELF, the inclusion of tigecycline provided assay sensitivity in the study.

Thus the primary objective of this study was to determine concentrations of Compound 1 in ELF and AC (mostly AM) and define the time course of pulmonary distribution with concurrent plasma PK sampling of Compound 1 in healthy adult subjects.

The secondary objective was to evaluate the PK of Compound 1 in pulmonary and plasma compartments in healthy adult subjects.

The exploratory objective was to determine the PK of Compound 1 in pulmonary and plasma compartments compared to tigecycline PK in pulmonary and plasma compartments in healthy adult subjects.

This study was designed as a single-center, multiple-dose, open-label study to determine concentrations of Compound 1 and tigecycline in pulmonary compartments (ELF and AC) in healthy adult subjects after administration of Compound 1 and tigecycline to steady state levels of dosing. Enrollment of approximately 62 subjects was planned to ensure approximately 42 subjects receive Compound 1 and to have a bronchioalveolar lavage (BAL) performed and approximately 20 subjects received tigecycline and had a BAL performed. Additional subjects were to be enrolled to replace subjects who discontinued or were screen failures.

Approximately 42 subjects received 5 doses of Compound 1 100 mg intravenously (30 minute infusions at t=0, 12, 24, 48, and 72 hours); Compound 1 subjects were assigned equally to 1 of 7 BAL sampling time points (approximately 6 subjects per BAL time point group) for collection of ELF and AC samples.

Upon completion of the study, 42 enrolled subjects received Compound 1 (69% male, median age 36 y, median BMI 27 kg/m$^2$). Six subjects had BAL at each of the 7 time points. One subject had a BAL sampling error and was not included in BAL analyses.

Compound 1 concentrations in ELF and AC were measured at only 1 observation time for each subject, and data from all subjects were pooled for a PK analysis of the mean intrapulmonary concentrations. The concentration of Compound 1 in BAL fluid was normalized by the dilution factor in respect to urea levels detected in plasma and BAL.

One standard bronchoscopy was performed for each subject. Within 1 BAL timepoint group, all subjects were assessed at the same timepoint, either at 0.5, 1, 2, 4, 8, 12, and 24 hours after the last dose administration on Day 4. A blood sample was taken at the time of bronschoscopy for plasma urea measurement. Additionally, blood samples were collected for plasma PK assessment at 0, 0.5 (end of infusion), 1, 1.5, 2, 3, 4, 6, 8, 12, and 24 hours post-dose for all subjects on Day 4.

Blood samples were taken and BAL performed in Compound 1-treated subjects according to the schedule below:

|  | Day 1 | Day 2 | Day 3 | Day 4 |
| --- | --- | --- | --- | --- |
| Compound 1 100 mg iv | Dose 1 t = 0 h | Dose 2 t = 12 h | Dose 3 t = 24 h | Dose 4 t = 48 h | Dose 5 t = 72 h |
| Blood sample for plasma PK (all subjects) | Pre-dose (baseline) | N/A | N/A | N/A | Predose, 0.5 (end of infusion), 1, 1.5, 2, 3, 4, 6, 8, 12, and 24 h Taken right before BAL (±3 min), from the arm contralateral to the infusion site |
| BAL sample (approximately 6 subjects for each time point) | N/A | N/A | N/A | N/A | Subjects assigned to either 0.5 (end of infusion), 1, 2, 4, 8, 12, or 24 h |
| Blood sample for plasma urea measurement (same time point as BAL; 1 sample per subject) | N/A | N/A | N/A | N/A | 0.5 (end of infusion) 1, 2, 4, 8, 12, or 24 h, taken right before BAL (±3 min) |

BAL = bronchoalveolar lavage; h = hour; N/A = not applicable; PK = pharmacokinetic; t = time.

For the patients receiving Compound 1, Mean (±SD) plasma pharmacokinetic parameters after the fifth Compound 1 dose included maximum concentration of 2.26±0.76 μg/mL, volume of distribution of 165±58 L, clearance of 8.03±1.43 L/h, and elimination half-life of 14.7±4.2 h. Mean (±SD) Compound 1 concentrations (μg/mL) at time of bronchoscopy and BAL were:

| Sampling Time | Plasma | ELF | AM |
| --- | --- | --- | --- |
| 0.5 h | 1.80 ± 0.13 | 1.73 ± 1.01 | 14.26 ± 9.30 |
| 1 h | 0.89 ± 0.19 | 2.25 ± 0.72 | 12.80 ± 8.48 |
| 2 h | 0.93 ± 0.33 | 1.51 ± 0.94 | 10.77 ± 7.59 |
| 4 h | 0.59 ± 0.15 | 0.95 ± 0.33 | 17.99 ± 7.17 |
| 8 h | 0.56 ± 0.12 | 0.58 ± 0.19 | 12.27 ± 4.70 |
| 12 h | 0.42 ± 0.07 | 0.61 ± 0.29 | 12.29 ± 4.61 |
| 24 h | 0.27 ± 0.05 | 0.41 ± 0.13 | 10.36 ± 4.04 |

Penetration ratios based on $AUC_{0-24}$ values of mean and median ELF and plasma concentrations were 1.47 and 1.42, whereas ratios of AC (Alveolar Cell, mostly AM) to plasma concentrations were 25.8 and 24.8.

Approximately 20 subjects received 1 dose of 100 mg tigecycline intravenously (30 minute infusion at t=0) followed by 6 doses of 50 mg tigecycline intravenously (30 minute infusions at t=12, 24, 36, 48, 60, and 72 hours). Tigecycline subjects were assigned equally to 1 of 4 BAL sampling timepoints (approximately 5 subjects per BAL timepoint group) for collection of ELF and AC samples. Tigecycline concentrations in ELF and AC were measured at only 1 observation time for each subject, and data from all subjects were pooled for a PK analysis of the mean intrapulmonary concentrations. The concentration of tigecycline in BAL fluid was normalized by the dilution factor in respect to urea levels detected in plasma and BAL.

Blood samples were taken and BAL performed in tigecycline-treated subjects according to the schedule below:

|  | Day 1 | Day 2 | Day 3 | Day 4 | | | |
| --- | --- | --- | --- | --- | --- | --- | --- |
| Tigecycline iv | Dose 1 100 mg t = 0 h | Dose 2 50 mg t = 12 h | Dose 3 50 mg t = 24 h | Dose 4 50 mg t = 36 h | Dose 5 50 mg t = 48 h | Dose 6 50 mg t = 60 h | Dose 7 50 mg t = 72 h |
| Blood sample for plasma PK (all subjects) | Pre-dose (base line) | N/A | N/A | N/A | N/A | N/A | Predose, 0.5 (end of infusion), 1, 1.5, 2, 3, 4, 6, 8, and 12 h Taken right before BAL (±3 min), from the arm contralateral to the infusion site |
| BAL sample (approximately 5 subjects for each timepoint) | N/A | N/A | N/A | N/A | N/A | N/A | Subjects assigned to either 2, 4, 6, or 12 h |
| Blood sample for plasma urea measurement (same timepoint as BAL; 1 sample per subject) | N/A | N/A | N/A | N/A | N/A | N/A | 2, 4, 6, or 12 h, taken right before BAL (±3 min) |

BAL = bronchoalveolar lavage;
h = hour;
N/A = not applicable;
PK = pharmacokinetic;
t = time.

Safety assessments included physical examinations, electrocardiograms (ECG), vital signs, standard clinical laboratory evaluations (blood chemistry, hematology), pregnancy testing, and adverse event (AE) and serious adverse event (SAE) monitoring.

Treatment-emergent adverse events (TEAEs) were reported in 29%. The most common TEAE was headache (12%). There were no severe or serious TEAEs, and no discontinuations due to TEAEs in Compound 1 treated subjects. There were no clinically significant changes in vital signs, laboratory or ECG parameters.

The duration of treatment was designed to ensure that both treatment arms were at steady state at the time of BAL.

During the bronchoscopy 4 aliquots of 50 mL each of sterile saline solution were instilled into the right lobe of the lungs, immediately aspirated, and placed on ice. The first bronchioalveolar lavage aliquot instilled (BALX) fraction was prepared and analyzed separately from subsequent instillations. The aspirate from the second through the fourth instillation, once pooled, represented the BAL fraction. An aliquot of BAL was removed and used to determine the cell count and differential cell composition including pulmonary macrophages. The remaining supernatant was centrifuged and the supernatant and cell pellet were immediately frozen pending analysis. An aliquot of the BAL supernatant was frozen separately for urea assay. The amount of test article detected in the cell pellet was normalized by the corresponding fraction of macrophages. Fraction BALX was analyzed in a similar manner, except the cell pellet was not assessed or assayed. A blood sample to determine urea concentration was obtained at the time of the second instillation (±3 minutes). The concentration of test article detected in the BALX and BAL fluid was normalized by the dilution factor with respect to urea levels detected in the BALX and BAL fractions respectively.

Subjects participated in the study for approximately 34 days. Following screening, eligible subjects were randomly assigned to Compound 1 or tigecycline treatment and assigned to a BAL lavage sample timepoint. Subjects had Baseline evaluations on Day −1 and then received test article treatment for 4 days followed by BAL at their assigned timepoint. A Study Completion visit was conducted on the day following the final test article dose. There was a Final Follow-up assessment 7 to 14 days following the subject's last dose of test article which may be completed by telephone contact or other interactive technology unless an examination was needed to evaluate AEs or abnormalities noted at the Study Completion visit.

Safety assessments included physical examinations, electrocardiograms (ECG), vital signs, standard clinical laboratory evaluations (blood chemistry, hematology), pregnancy testing, and AE and SAE monitoring.

Dosing Regimen:

The current intended therapeutic dose of Compound 1 for the treatment of CABP is 100 mg iv every 12 hours (q12 h) for 2 doses followed by every 24 hours (q24 h), with the option to switch to 300 mg orally q24 h.

The approved therapeutic dose of tigecycline (TYGACIL®) for the treatment of CABP is 100 mg iv for 1 dose followed by 50 mg iv q12 h.

Patient Inclusion/Exclusion Criteria

Enrolled patients were male or female subjects age 18 to 55 years of age, in good health as determined by past medical history, physical examination, vital signs, ECG, and laboratory tests (no clinically significant abnormalities in the opinion of the investigator). Vital signs (oral body temperature, systolic and diastolic blood pressure (BP), and pulse rate) were assessed in a sitting position after the subject had rested for at least 3 minutes. Sitting vital signs should be within the following ranges: oral body temperature, 35.0° C. to 37.5° C. (95.0° F. to 99.5° F.); systolic BP, 90 to 140 mm Hg; diastolic BP, 50 to 90 mm Hg; pulse rate, 40 to 90 bpm; Blood pressure and pulse were assessed again after 3 minutes in a standing position at the Screening visit. There were no more than a 20 mm Hg drop in systolic or 10 mm Hg drop in diastolic BP and increase in heart rate (>20 bpm) associated with clinical manifestation of postural hypotension. Out-of-range vital signs may be repeated once at the discretion of the investigator, if necessary.

Subjects weighed at least 50 kg, and had a body mass index (BMI) within the range of ≥18.0 to ≤30.0 kg/m². Females had a negative serum pregnancy test at the Screening and Baseline visits and agreed to comply with using an acceptable form of birth control from Screening through the final follow-up assessment. Males agreed to use an acceptable method of birth control with female partner(s) and did not donate sperm from Screening through the Final Follow-up assessment.

Patients were excluded from the study if one or more of the following was present:
- Use of other investigational drugs within 5 half-lives or 30 days prior to Screening, whichever is longer.
- Had a history of hypersensitivity or allergic reaction (e.g., anaphylaxis, urticaria, other significant reaction) to any tetracycline (e.g., minocycline, doxycycline, or tigecycline).
- Had a history of clinically significant ECG abnormalities, or any of the following ECG abnormalities at the Screening or Baseline visit: PR >220 msec, QRS complex >120 msec, Long QT syndrome, QTc Fridericia's Correction Formula (QTcF) >450 msec (males), and QTcF >470 msec (females)
- Pregnant or nursing (breastfeeding) women.
- History of malignancy of any organ system (other than localized basal cell carcinoma of the skin), treated or untreated, within the past 5 years, regardless of whether there is evidence of local recurrence or metastases.
- Use of tobacco products in the 3 months prior to Screening.
- A positive urine cotinine test at Screening or Baseline.
- Use of any prescription drugs or herbal supplements within 4 weeks prior to the Baseline visit, and/or over-the-counter (OTC) medications including dietary and fitness/body-building supplements (vitamins included) within 2 weeks prior to the Baseline visit.
- Donation or loss of 400 mL or more of blood or plasma within 8 weeks prior to the Baseline visit, or longer if required by local regulation.
- Hemoglobin levels <12.5 g/dL for males, <11.5 g/dL for females at Screening/Baseline visit.
- Significant illness within 2 weeks prior to Baseline visit.
- History of autonomic dysfunction (e.g., recurrent episodes of fainting, palpitations, etc) within 3 years prior to Screening.
- History of acute or chronic bronchospastic disease (including asthma and chronic obstructive pulmonary disease (COPD), treated or not treated) within 3 years prior to Screening.
- Any surgical or medical condition which, in the opinion of the investigator, might significantly alter the absorption, distribution, metabolism, or excretion of drugs, or which may jeopardize the subject in case of participation in the study.

History of, or active, inflammatory bowel disease, ulcers, GI or rectal bleeding, or pancreatitis.

Liver disease or liver injury as indicated by abnormal LFTs such as aspartate aminotransferase (AST), ALT, gamma-glutamyl transpeptidase (GGT), CK, alkaline phosphatase (ALP), or serum bilirubin. The investigator should be guided by the following criteria: Serum bilirubin may not exceed 1.2 times the upper limit of normal (ULN); Any other single parameter listed above may not exceed 1.5 times ULN; any elevation of more than 1 parameter excludes a subject from participation in the study. Testing may be repeated once more as soon as possible to rule out lab error. Recheck results must not meet the criteria above in order for subject to qualify.

History or presence of impaired renal function as indicated by clinically significant abnormal creatinine or blood urea nitrogen (BUN) and/or urea values, or abnormal urinary constituents (e.g., albuminuria).

Evidence of urinary obstruction or difficulty in voiding at Screening.

Was known to be human immunodeficiency virus (HIV)-positive.

Had known chronic hepatitis B or chronic hepatitis C infection.

Positive alcohol test or positive drug screen at the Screening or Baseline visit.

Had previously been treated with Compound 1 or previously enrolled in this study.

Any concomitant condition that, in the opinion of the investigator, is likely to interfere with the determination of AEs or completion of the study procedures.

Procedures

There were 3 protocol-defined phases of the study: Screening, Treatment and Follow-up. The study had the following protocol-defined evaluations:

Screening visit

Baseline visit

Visits on Days 1, 2, and 3 (test article dosing) Visit on Day 4 (test article dosing and BAL)

Study Completion visit on Day 5

Final Follow-up assessment: Study Day 11-18 (7-14 days after the last dose of test article)

Subjects who discontinued study treatment prematurely had the Study Completion procedures performed prior to clinic discharge and a Final Follow-up assessment.

Screening was used to establish subject eligibility and Baseline characteristics for each subject. The following information was collected: review of inclusion/exclusion criteria; relevant medical/surgical history and current medical conditions (predisposing factors that may affect lung function (e.g., prior lung infection, mild to moderate COPD, asthma, history of smoking, chronic cough, etc); demographics; physical examination; urine alcohol test, drug screen, cotinine test; vital signs; 12-lead ECG; laboratory tests (hematology, chemistry, coagulation, pregnancy test (women only)); and AEs since the signing of the ICF Concomitant medications (past 4 weeks).

The treatment period was 5 days in duration. Subjects who met inclusion criteria and did not meet exclusion criteria received their first dose of test article. The following assessments were done: Vital signs; AEs; Concomitant treatments; and Test article administration and accountability.

During the Intravenous Treatment Phase (Test Article), infusions of Compound 1 were administered continuously over approximately 30 minutes (at least 30 minutes and not more than 45 minutes) according to the schedule in Table 1-3 below. Infusions of tigecycline were administered continuously over approximately 30 minutes (at least 30 minutes and not more than 45 minutes) according the schedule in Table 1-4. All infusion start and stop times and compliance (delivery of ≥90% of the dose) were recorded in source documents and on the eCRF.

TABLE 1-1

Treatment Regimen for IV Compound 1

| Time[a] | Dose[b] |
|---|---|
| t = 0 h | Compound 1 100 mg in 100 mL NS |
| t = 12 h | Compound 1 100 mg in 100 mL NS |
| t = 24 h | Compound 1 100 mg in 100 mL NS |
| t = 48 h | Compound 1 100 mg in 100 mL NS |
| t = 72 h | Compound 1 100 mg in 100 mL NS | t = time;
NS = normal saline (0.9% sodium chloride) for injection
[a]The start time of the start of the first infusion was designated time 0 (t = 0 h). Subsequent infusions were administered within ±1 hour of the target infusion times listed.
[b]All 100 mL infusions of Compound 1 were administered continuously over 30 min (at least 30 min and not more than 45 min).

TABLE 1-2

Treatment Regimen for IV Tigecycline

| Time[a] | Dose[b] |
|---|---|
| t = 0 h | tigecycline 100 mg in 100 mL NS |
| t = 12 h | tigecycline 50 mg in 100 mL NS |
| t = 24 h | tigecycline 50 mg in 100 mL NS |

TABLE 1-1

Treatment Regimen for IV Compound 1

| Time[a] | Dose[b] |
|---|---|
| t = 36 h | tigecycline 50 mg in 100 mL NS |
| t = 48 h | tigecycline 50 mg in 100 mL NS |
| t = 60 h | tigecycline 50 mg in 100 mL NS |
| t = 72 h | tigecycline 50 mg in 100 mL NS | t = time;
NS = normal saline (0.9% sodium chloride) for injection.
[a]The start time of the start of the first infusion was designated time 0 (t = 0 h). Subsequent infusions were administered within ±1 hour of the target infusion times listed.
[b]All 100 mL infusions of tigecycline were administered continuously over 30 min (at least 30 min and not more than 45 min).

During the Follow-up Phase, subjects were evaluated at 2 visits after the completion of treatment: at the Study Completion visit on Day 5 and at a Final Follow-up assessment on Study Days 11 to 18 (7 to 14 days after subject's last dose of test article). The Final Follow-up Assessment was conducted by telephone contact unless an examination was needed to evaluate AEs or abnormalities noted at Study Completion.

For IV injection, Compound 1 was supplied as 100 mg (plus 4% overfill) sterile, lyophilized powder for reconstitution packaged in a clear, glass vial with a rubber stopper and aluminum overseal. Excipients included tosylate acid counter ion, sucrose, hydrochloric acid and sodium hydroxide to adjust the pH. Each vial was reconstituted into a clear solution by adding 5 mL Sterile Water for Injection. The vial was swirled gently to ensure complete dissolution prior to use. Excessive shaking was avoided to prevent foaming. Reconstituted vials were used immediately to prepare the infusion solution. The infusion solution was prepared by withdrawing 5 mL of reconstituted solution from the vial and slowly injecting into a 100 mL normal saline (NS) for injection (0.9% sodium chloride) infusion bag. The prepared infusion solution was used within 8 h or stored at up to 24 h at 2° C. to 8° C. (35.6° F. to 46.4° F.). The 100 mL infusion solution was administered at room temperature continuously over 30 minutes (at least 30 minutes and not more than 45 minutes).

Reconstituted Compound 1 was injected as 100 mg iv q12 h for first 2 doses followed by 100 mg iv q24 h (starting 24 h after first dose) for 2-3 doses. Total treatment consisted of 5 doses, and a duration of 5 days.

The comparator test article Tigecycline was injected as 100 mg iv first dose followed by 50 mg iv q12 h for 6 doses. Total treatment consisted of 7 doses, for a duration of 5 days.

Safety

Any subject who received at least 1 dose of test article was included in the evaluation for safety. Safety was assessed by the following measures: Physical exams; AEs and SAEs; Vital signs; Laboratory assessments (Blood samples for hematology, chemistry, and coagulation (prothrombin time only)); ECG; and Pregnancy assessments.

Data Analysis

All analyses of data for this study complied with International Conference on Harmonisation of Technical Requirements for Registration of Pharmaceuticals for Human Use (ICH-E9) and the sponsor's guidance documents and standards. Statistical analyses were performed using Statistical Analysis Software (SAS).

a) Analysis Populations

Subject populations have been defined for the various analyses of PKs and safety, as follows:

The PK population consisted of all subjects who received test article and had at least 1 evaluable PK parameter.

The Safety population consisted of all subjects who received at least 1 dose of test article.

b) Subject Demographics and Baseline Characteristics

Descriptive statistics, by treatment arm, was provided for the following: Subject disposition (completed test article, discontinued test article by reason for discontinuation, completed study, discontinued study by reason for discontinuation); Protocol deviations; Medical histories and continuing medical conditions.

Baseline demographic and medical variables were analyzed using a 2-sided Fisher's exact test (for categorical variables) or a 2-sided Wilcoxon Rank Sum test (for ordinal and continuous variables).

c) Safety Outcome Measures

Safety variables included the incidence rate of AEs, change in vital signs, ECG parameters, and laboratory test results obtained during the course of the study. Subjects were analyzed according to the treatment actually received.

d) PK

All completed subjects with evaluable plasma PK parameter data were included in the PK data analysis. The following Compound 1 and tigecycline plasma PK parameters were determined:

Area under the curve (AUC) from time 0 to 24 hours after dosing ($AUC_{0-24}$) for Compound 1, and AUC from time 0 to 12 hours after dosing ($AUC_{0-12}$) for tigecycline, Maximum plasma concentration ($C_{max}$), Time to maximum plasma concentration ($T_{max}$) and Terminal elimination half-life ($T_{1/2}$) associated with the terminal slope of the semilogarithmic concentration-time curve.

All the biofluid concentrations were expressed in ng/mL. All concentrations below the limit of quantification (BLQ) or missing data were labeled as such in the concentration data listings. Concentrations BLQ were treated as zero in summary statistics for concentration data only. They were not considered for calculation of PK Parameters (with the exception of the predose samples). PK parameters were determined using non-compartmental method(s) using WinNonlin Pro.

The primary objective of the study was to assess the concentration of Compound 1 in lung ELF and AC (mostly AM). The concentration of Compound 1 and tigecycline in lung ELF and AC were calculated as area under the (concentration/time) curve in epithelial lung fluid ($AUC_{ELF}$)/area under the (concentration/time) curve in plasma ($AUC_{plasma}$) and area under the (concentration/time) curve in alveolar cells ($AUC_{AC}$)/$AUC_{plasma}$, respectively. These were obtained from the above plasma PK parameter calculations ($AUC_{0-24}$ and $AUC_{0-12}$). The tigecycline concentration information was serve as an internal validation for assay sensitivity purposes.

To determine the $AUC_{ELF}$ parameters for Compound 1 and tigecycline, their concentration data were used by deriving from the corresponding BAL concentrations. The concentration of Compound 1 or tigecycline in the lung ELF ($C_{ELF}$) was calculated as: $C_{ELF}=C_{BAL}*(V_{BAL}/V_{ELF})$, where $C_{BAL}$ is the concentration in the BAL fluid, $V_{BAL}$ is the volume of the aspirated BAL fluid, and $V_{ELF}$ is the volume of lung ELF.

The volume of the lung ELF within the BAL fluid was estimated by ($urea_{BAL}/urea_{plasma}$), where $urea_{BAL}$ and $urea_{plasma}$ represented the concentrations of urea in the BAL fluid and plasma, respectively.

Compound 1 and tigecycline concentration data from ELF, AC, and AM were presented in a listing. $AUC_{ELF}$ and $AUC_{AC}$ were determined from pooled pulmonary concentration data and were summarized by treatment group. For the Compound 1 cohort there were at least 6 ELF and AC concentrations for each of the 7 timepoints over the 24 hour dosing interval. For the tigecycline cohort there were 5 ELF and AC concentrations for each of the 4 timepoints over the 12 hour dosing interval.

The calculated concentration of Compound 1 and tigecycline in lung ELF and AC as the ratios of $AUC_{ELF}/AUC_{plasma}$ and $AUC_{AC}/AUC_{plasma}$, were summarized by treatment group. BALX was assessed separately and in an identical fashion. The impact of "BALX" on the PK understanding of Compound 1 and tigecycline was assessed.

PK Samples for Compound 1 or Tigecycline Concentration

The permitted windows for PK sample collection were as follows:

| PK blood collection-scheduled time relative to test article dose | Window |
|---|---|
| Predose | within 10 min before test article administration |
| 0.5 to 1 h | ±2 min |
| 1.5 h to 6 h | ±5 min |
| 8 h to 24 h | ±15 min |
| Sample collected at the bronchoscopy scheduled time | ±3 min of the second BAL instillation |

| Window | |
|---|---|
| Bronchoscopy - BAL and AC collection | |
| Scheduled time | ±15 min |
| Blood sample for plasma urea testing | |
| Sample collected at the bronchoscopy scheduled time | ±3 min of the second BAL instillation |

For PK blood collection and processing, all blood samples were taken by either direct venipuncture or an indwelling cannula inserted in a forearm vein (on the arm contralateral to the infusion site) at the timepoints specified in the Study Flowchart. The PK blood sample collected at the bronchoscopy scheduled time was obtained at the time of the second BAL instillation (±3 minutes) from the arm contralateral to the infusion site.

Blood samples were collected into labeled 4 mL tubes containing sodium heparin. Immediately after the sample was collected, the tube was gently inverted 5 to 8 times to thoroughly mix the anticoagulant and then placed upright in a cryoblock or test tube rack surrounded by ice until centrifugation. Samples were centrifuged at 1500×g (gravity) for 10 minutes at approximately 4° C. within 30 minutes of collection. The resultant plasma was divided into 2 equal aliquots, placed in individual cryovials, and immediately frozen at −70° C. or colder within 1 hour of collection. The tubes were kept frozen at −70° C. or colder pending shipment to the bioanalytical laboratory.

For BAL and AC sample collection and handling, one standard bronchoscopy was performed in each subject following the last administration of test article at the timepoints specified in the Study Flowchart. Subjects were continuously monitored during bronchoscopy. Blood pressure, heart rate, and respiratory rate were recorded just prior to (within 30 minutes) the bronchoscopy procedure scheduled time, 30 minutes after, and 60 minutes after of the bronchoscopy procedure scheduled time. Topical lidocaine, 4% solution for the oropharynx, and 2% solution for the nasopharynx, were applied to the upper airways to prepare subjects for bronchoscopy. If needed, a 1% lidocaine solution was used in the lower airways. A fiberoptic bronchoscope was inserted into the middle lobe of the right lung. Four-50 mL aliquots of sterile 0.9% saline solution were instilled into the right lobe and immediately aspirated, and placed on ice. The first 50 mL instilled (fraction BALX) was collected (2 aliquots of 4 mL), immediately placed on ice, the volume recorded, stored, prepared, and analyzed separately from subsequent instillations. The aspirate from the second through the fourth instillation was collected immediately, placed on ice, and the volume recorded. The collective aspirates (second through fourth), once pooled, represented the BAL fraction.

An aliquot of BAL was removed and used to determine the cell count and differential cell composition. The fraction of pulmonary macrophages was determined during cell count and differentiation. An aliquot of the BALX and BAL supernatants were reserved for a urea assay. The remaining supernatant was centrifuged immediately at 400×g for 5 minutes in a refrigerated centrifuge. Supernatant, fractionated into 5 mL aliquots, and the cell pellet were immediately frozen at −70° C. or colder pending analysis. Fraction BALX was analyzed in a similar manner, with the exception that the cell pellet was not assessed or assayed.

For urea assay in BAL fluid and plasma, a blood sample to determine urea concentration was obtained at the time of the second BAL instillation (±3 minutes). Urea blood samples were taken by either direct venipuncture or an indwelling cannula inserted in a forearm vein (on the arm contralateral to the infusion site). Plasma was prepared from the urea blood sample in the same manner as plasma samples for PK analysis.

Plasma samples, BAL supernatant samples and BALX supernatant samples were analyzed for urea concentration by the bioanalytical laboratory.

After all of the PK samples from a single subject had been collected and frozen at −70° C. or colder, the primary samples from each timepoint were batched together with corresponding primary samples from other subjects and be carefully packaged and shipped frozen at −70° C. or colder to the bioanalytical laboratory designated by the sponsor. Samples were shipped with sufficient dry ice to remain frozen during overnight transit. For each subject and timepoint, the remaining stored aliquots were retained on-site at −70° C. or colder until released or requested by the sponsor.

The bioanalytical laboratory assayed the samples for Compound 1 or tigecycline using a specific, sensitive, and validated liquid chromatography/tandem mass spectrometry (LC/MS/MS) method approved by the sponsor.

To determine ELF volume and concentrations of Compound 1 or Tigecycline in ELF, urea measured in the BALX and BAL supernatant and in plasma was used to calculate the volume of ELF using the conventional urea dilution method. The volume of ELF was determined by the following equation:

$$V_{ELF} = V_{BAL} * (\text{urea}_{BAL}/\text{urea}_{plasma}),$$

where $V_{ELF}$=volume of ELF in the BAL sample, $V_{BAL}$=volume of aspirated BAL fluid, $\text{ureas}_{BAL}$=concentration of urea in BAL supernatant, and $\text{urea}_{plasma}$=concentration of urea in plasma.

The concentration of Compound 1 or tigecycline in ELF ($C_{ELF}$) was calculated as:

$$C_{ELF} = C_{BAL} * (V_{BAL}/V_{ELF}),$$

where $C_{ELF}$=concentration of Compound 1 or tigecycline in ELF, $C_{BAL}$=measured concentration of Compound 1 or tigecycline in BAL supernatant, $V_{ELF}$=volume of ELF in the BAL sample, and $V_{BAL}$=volume of aspirated BAL fluid.

To determine AC volume and concentration of Compound 1 or Tigecycline in AC and AM, the volume of AC collected in the BAL cell pellet suspension was determined from the BAL fluid cell count. The volume of cells was calculated by multiplication of cell counts in ELF with the known volume of ACs. The volume of cells was determined by multiplying the cell count with the mean macrophage cell volume of 2.42 µL/10$^6$ cell.

The measured concentration of Compound 1 or tigecycline in AC ($C_{AC}$) was determined by the following equation:

$$C_{AC} = (C_{pellet\ suspension}/V_{AC}),$$

where $C_{pellet\ suspension}$ is the Compound 1 or tigecycline concentration in 1 mL cell suspension and $V_{AC}$ is the volume of AC in 1 mL cell suspension.

The measured concentration of Compound 1 or tigecycline in AMs ($C_{AM}$) was derived from $C_{AC}$ by adjusting for the percentage of macrophages and monocytes in the AC as determined by a differential cell count of the BAL fluid.

FIG. 1 shows the result of mean Compound 1 concentration vs. time profile in AC, plasma, and ELF. It is apparent that the mean Compound 1 concentration in AC (mostly AM) is at least an order of magnitude higher (about 25 fold)

than that in plasma, while the mean Compound 1 concentration in ELF is at least about 40% higher than that in plasma. See tables.

| Sampling Time | ELF to Plasma (Mean, SD) | AM to Plasma (Mean, SD) |
|---|---|---|
| 0.5-hour[a] | 0.95 ± 0.56 | 8.12 ± 5.95 |
| 1-hour[a] | 2.72 ± 1.26 | 13.85 ± 7.38 |
| 2-hour[b] | 1.50 ± 0.61 | 12.29 ± 6.57 |
| 4-hour[a] | 1.79 ± 0.49 | 34.72 ± 15.14 |
| 8-hour[a] | 1.07 ± 0.45 | 23.12 ± 11.17 |
| 12-hour[a] | 1.44 ± 0.57 | 28.97 ± 8.78 |
| 24-hour[a] | 1.65 ± 0.86 | 40.33 ± 10.29 |

[a] 6 reported plasma, ELF, and AM concentrations at this sampling time
[b] 5 samples plasma, ELF, and AM concentrations at this sampling time Compound 1 Demonstrated Higher Epithelial Lining Fluid (ELF) and Alveolar Cellular (AC) Concentrations Ratio

|  | Plasma (μg * h/mL) | ELF (μg * h/mL) | Ratio ELF:Plasma | AC (μg * h/mL) | Ratio AC:Plasma |
|---|---|---|---|---|---|
| $AUC_{mean}$ | 11.73 | 17.23 | 1.47 | 302.5 | 25.8 |
| $AUC_{median}$ | 11.80 | 16.74 | 1.42 | 292.3 | 24.8 |

$AUC_{mean}$ = Area-under-the-curve based on mean concentration at each BAL sampling time
$AUC_{median}$ = Area-under-the-curve based on median concentration at each BAL sampling time This data provides important information on the time course and magnitude of extracellular and intracellular concentrations of Compound 1 in the lung. Intravenous administration of Compound 1 at 100 mg as a 30-minute infusion produced concentrations that were higher in epithelial lining fluid (ELF) and alveolar cellular (AC, including AM) than simultaneous plasma concentrations throughout the 24-hour period after five doses. The in vitro activity against common typical and atypical pathogens and the sustained ELF and AC/AM concentrations for 24 hours suggest that Compound 1 can be a useful antibacterial agent for the treatment of lower respiratory tract bacterial infections caused by susceptible pathogens.

Safety Monitoring

An AE is any untoward, undesired, or unplanned event in the form of signs, symptoms, disease, or laboratory or physiologic observations occurring in a person given a test article or in a clinical study. The event does not need to be causally related to the test article or clinical study. An AE includes, but is not limited to, the following: any clinically significant worsening of a preexisting condition; an AE occurring from overdose of a test article, whether accidental or intentional (overdose is a dose greater than that specified in the protocol); an AE occurring from abuse (e.g., use for nonclinical reasons) of a test article; and an AE that has been associated with the discontinuation of the use of a test article.

A SAE is an AE that: results in death; is life-threatening; requires hospitalization or prolongation of an existing hospitalization; results in a persistent or significant disability or incapacity; results in a congenital anomaly or birth defect; or additionally, important medical events that may not result in death, be life-threatening, or require hospitalization may be considered SAEs when, based on appropriate medical judgment, they may jeopardize the subject and may require medical or surgical intervention to prevent 1 of the outcomes listed in this definition. Examples of such events include allergic bronchospasm requiring intensive treatment in an emergency room or at home, blood dyscrasias or convulsions that do not result in hospitalization, or development of drug dependency or drug abuse.

If there was any doubt about whether the information constitutes an SAE, the information was treated as an SAE.

A protocol-related AE is an AE occurring during a clinical study that is not related to the test article, but is considered by the investigator or the Medical Monitor (or designee) to be related to the research conditions, i.e., related to the fact that a subject is participating in the study. For example, a protocol-related AE may be an untoward event related to a medical procedure required by the protocol.

Example 2 Effect of Food on the Bioavailability of Omadacycline in Healthy Volunteers Compound 1 (9-[(2,2-dimethyl-propyl amino)-methyl]-minocycline) is a first-in-class aminomethylcycline antibiotic that is characterized by improved in vitro antimicrobial activity (Honeyman et al, *Antimicrob Agents Chemother.* 59:7044-7053, 2015).

Phase 3 studies have concluded with Compound 1 as oral and intravenous (IV) monotherapy in patients with acute bacterial skin and skin structure infection (ABSSSI). During the development process, oral Compound 1 formulations have evolved from free-base in a capsule through a series of tablet and salt formulations in order to optimize oral bioavailability while improving tolerability. The current phase 3 tablet formulation is the tosylate salt of Compound 1, which has been shown to have an absolute bioavailability of 34.5% when administered under fasting conditions. The primary objective of this study was to evaluate the relative bioavailability of a single oral 300 mg dose of Compound 1 (administered as the phase 3 tablet formulation) at various times after the consumption of food in healthy adult subjects.

The result of this study showed that food consumption has an effect on the oral bioavailability of a single 300 mg Compound 1 dose.

Briefly, the study was a phase 1, randomized, open-label 4-period, crossover study. Before dosing on Day 1 of Period 1, subjects were randomized to one of four treatment sequences (see Table 2-1). On Day 1 of each period, subjects received a single oral dose of 300 mg Compound 1 (2×150 mg tablets) at various times after the consumption of food. There was a washout period of at least 5 days between each dosing period. A final study completion visit occurred 6 to 10 days after the last dose of Compound 1.

TABLE 2-1

Treatment Sequences

| Sequence | Period 1 | Period 2 | Period 3 | Period 4 |
|---|---|---|---|---|
| ADBC | A | D | B | C |
| BACD | B | A | C | D |
| CBDA | C | B | D | A |
| DCAB | D | C | A | B |

A: subjects fasted overnight (no food or drink except for water for at least 6 hours before dosing); a standard high-fat (nondairy) meal was served 3 hours after dosing
B: a standard high-fat (nondairy) meal completed at 4 hours before dosing
C: a standard high-fat (nondairy) meal completed at 2 hours before dosing
D: a standard high-fat meal including dairy completed at 2 hours before dosing The high-fat (approximately 50% of total caloric content of the meal) and high-calorie (approximately 800 to 1000 calories) meal followed Food and Drug Administration guidance recommendations, and provided approximately 150, 250, and 500 to 600 calories from protein, carbohydrate, and fat, respectively (FDA Guidance, 2002). These meals were to be consumed within 20 minutes. Dose administration for Treatments B, C, and D was based off of the end time of the meal. During all 4 treatment periods, subjects received no food or drink except water for at least 3 hours after dosing and no dairy products, antacids or multivitamins for 4 hours after dosing.

A total of 32 subjects were enrolled and dosed in at least one treatment period. Overall mean age was 32.3 years, with a range of 21 to 50 years; 47% were male (Table 2-2). One subject was discontinued from the study because of a positive alcohol screen at baseline of period 3 and did not receive Treatments A and D. One subject requested withdrawal and did not receive Treatments B and C. PK data were available for 31 subjects for each treatment condition.

TABLE 2-2

Baseline Demographics

| | Subjects (n = 32) |
|---|---|
| Age, years[a] | 32.2 (8.0) |
| Age range, years | 21-50 |
| Male, n (%) | 15 (46.9) |
| Race, n (%) | |
| white | 24 (75) |
| black/African American | 8 (25) |
| Hispanic/Latino | 12 (37.5) |
| Height, cm[a] | 168.0 (9.5) |
| Weight, kg[a] | 71.5 (13.4) |
| BMI (body Mass Index), kg/m² [a] | 25.2 (3.2) |

[a]Mean (Standard Deviation)

Blood samples for pharmacokinetic (PK) assessments of Compound 1 were collected before dosing (predose) and at 0.5, 1, 1.5, 2, 2.5, 3, 4, 6, 8, 12, 16, and 24 hours after dosing in each period. PK parameters included: Area under the plasma concentration-time curve (AUC) from time 0 to 24 hours after dosing ($AUC_{0-24}$); AUC from time 0 to the last quantifiable concentration ($AUC_0$-t); AUC time 0 extrapolated to infinity ($AUC_{0-inf}$); Maximum (peak) observed plasma concentration ($C_{max}$); Time to reach $C_{max}$ ($T_{max}$); Terminal elimination half-life ($T_{1/2}$); Terminal phase rate constant ($\lambda z$).

Safety and tolerability was assessed by: Adverse events (AEs); vital sign measurements at multiple time-points within 24 hours post-dose in each treatment period; and clinical laboratory tests 24 hours post-dose in each treatment period.

For statistical analysis, individual PK parameters for Compound 1 were summarized with descriptive statistics. Geometric means were determined for AUC and $C_{max}$. PK parameters were evaluated using noncompartmental analysis using Phoenix® WinNonlin® (Pharsight Corp, St. Louis, Mo.), Version 6.2.1. Confidence intervals (CI) for test treatments (fed states: Treatments B, C, and D) compared with the reference treatment (fasted state: Treatment A) were constructed for $AUC_{0-24}$, $AUC_{0-t}$, $AUC_{0-inf}$ and $C_{max}$. Absence of the effect of food was concluded if the 90% CI for the test-to-reference ratios (B/A, C/A, or D/A) of geometric means were contained within the criterion interval of 80% to 125% for $AUC_{0-24}$, $AUC_{0-t}$, $AUC_{0-inf}$ and $C_{max}$. For $T_{max}$, the Wilcoxon signed rank test was performed. $p \leq 0.05$ was considered statistically significant.

A linear mixed-effect model with treatment condition, sequence, and period as fixed effects and subject nested within sequence as a random effect was fitted to the natural log-transformed PK parameters for estimation of effects and 90% confidence intervals (CIs) for the fed states compared with the fasted state.

TABLE 2-3

Plasma PK Parameters for Compound 1 after a Single 300 mg Oral Dose

| | Mean (Coefficient of Variation) | | | |
|---|---|---|---|---|
| Parameter | Treatment A<br>N = 31 | Treatment B<br>N = 31 | Treatment C<br>N = 31 | Treatment D<br>N = 31 |
| $AUC_{0-24}$, mcg * h/mL | 7.2 (28.1) | 6.1 (26.3) | 4.2 (23.4) | 2.8 (44.3) |
| $AUC_{0-t}$, mcg * h/mL | 7.2 (28.1) | 6.1 (26.3) | 4.2 (23.4) | 2.8 (44.3) |
| $AUC_{0-inf}$, mcg * h/mL | 10.2 (27.0)[b] | 8.8 (29.2) | 6.0 (25.4) | 4.0 (44.1) |
| $C_{max}$, mcg/mL | 0.6 (25.3) | 0.6 (25.0) | 0.4 (22.4) | 0.3 (42.6) |
| $T_{max}$, h[a] | 2.5 (1.5, 4.1) | 2.9 (1.0, 6.9) | 2.9 (1.0, 6.0) | 2.9 (1.0, 6.0) |
| $T_{1/2}$, h | 13.8 (10.3)[b] | 13.6 (12.7) | 13.6 (12.2) | 13.5 (14.7) |

PK analysis showed that, for the 31 subjects included in the PK analysis, fasted $AUC_{0-inf}$, $AUC_{0-t}$, and $AUC_{0-24}$ were 10.2, 7.2, and 7.2 mcg*h/mL, respectively, and $C_{max}$ was 0.6 mcg/mL. Across all treatment periods, mean $T_{1/2}$ ranged from 13.5 to 13.8 hours, and median $T_{max}$ ranged from 2.5 to 2.9 hours. No treatment-related adverse events or clinically relevant changes in laboratory values, or vital signs occurred. See Table 2-3.

A significant reduction in systemic exposure to omadacycline was observed for all three treatments (Treatments B, C, and D) vs. Treatment A (FIG. 1 and Table 2-4).

TABLE 2-4

Effect of Food on Plasma PK Parameters of Compound 1 (N = 31)

| Parameter | Treatment | Geometric LS Mean | Treatment Comparison | Ratio of Geometric LS Mean (%) | 90% CI of Ratio (%) |
|---|---|---|---|---|---|
| $AUC_{0-24}$, mcg * h/L | A | 7.4 | | | |
| | B | 6.2 | B/A | 83.4 | 74.9, 92.7 |
| | C | 4.3 | C/A | 57.7 | 51.9, 64.2 |
| | D | 2.8 | D/A | 37.3 | 33.6, 41.5 |
| $AUC_{0-t}$, mcg * h/L | A | 7.4 | | | |
| | B | 6.2 | B/A | 83.3 | 74.9, 92.7 |
| | C | 4.3 | C/A | 57.7 | 51.9, 64.1 |
| | D | 2.8 | D/A | 37.9 | 33.5, 41.4 |
| $AUC_{0-inf}$, mcg * h/L | A* | 10.6 | | | |
| | B | 9.0 | B/A | 84.7 | 75.8, 94.6 |
| | C | 6.2 | C/A | 58.4 | 52.3, 65.3 |
| | D | 4.0 | D/A | 37.9 | 34.0, 42.3 |
| $C_{max}$, mcg/L | A | 0.66 | | | |
| | B | 0.56 | B/A | 84.5 | 75.9, 94.1 |
| | C | 0.39 | C/A | 60.1 | 54.0, 66.9 |
| | D | 0.27 | D/A | 40.7 | 36.5, 45.2 |

*N = 30, a terminal mono-exponential phase could not be identified for one subject.
CI, confidence interval;
LS, least squares The effect of food was more pronounced when a high-fat meal was consumed closer to dosing and when dairy was included in the meal. Compared with a fasted dose, Compound 1 exposure ($C_{max}$ and AUC) was Reduced by 15% to 17% for a nondairy meal 4 hours before dosing; reduced by 40% to 42% for a nondairy meal 2 hours before dosing; and reduced by 59% to 63% for a dairy meal 2 hours before dosing. The between-subject variability in systemic exposure to omadacycline was similar for Treatments A, B and C (CV 22.4-29.2%) for $C_{max}$ and AUC. By contrast, for Treatment D the CV was 42.6-44.4% for these parameters.

Concerning safety and tolerability, two subjects experienced treatment emergent AEs (one reported nausea, one reported somnolence); both events were of mild intensity and considered unrelated to study drug. No subject discontinued the study for an AE, and no subject experienced a serious AE (SAE). A slight increase from baseline in heart rate (median 8 to 10 bpm at 4 to 6 hours post dose) was observed for Treatment A (i.e., the group with highest omadacycline exposure). In all other treatment groups, the median change from baseline in heart rate was ≤3 bpm at all measured time points. No notable changes in blood pressure were observed. There were no clinically significant changes in clinical laboratory tests.

The results showed that a single oral dose of Compound 1 was well tolerated. Administration of a 300 mg dose within 2 to 4 hours of food reduced the bioavailability compared with the fasted state. Thus preferably, once daily oral Compound 1 should be administered at least 6 hours following a meal.

Example 3 A Phase 3 Randomized, Double-Blind, Multi-Center Study to Compare the Safety and Efficacy of Compound 1 IV/PO to Moxifloxacin IV/PO for Treating Adult Subjects with Community-Acquired Bacterial Pneumonia (CABP)

This study evaluates the safety and efficacy of intravenous (iv) and oral (po) Compound 1 as compared to iv and po moxifloxacin in the treatment of adults with CABP.

More specifically, the primary objective of this study is to demonstrate that Compound 1 100 mg iv every 12 hours (q12 h) for 2 doses, followed by 100 mg iv/300 mg po once every 24 hours (q24 h) is non-inferior to moxifloxacin 400 mg iv/po q24 h in the treatment of adults with CABP. The secondary objectives are: to evaluate the safety of Compound 1 in the treatment of adult subjects with CABP in the Safety population; to evaluate the Clinical Response according to the identified causative pathogen; and to evaluate the pharmacokinetics (PK) of Compound 1 in adult subjects with CABP.

According to the study design, a randomized (1:1), active comparator-controlled, double-blind, Phase 3 study was conducted to compare Compound 1 and moxifloxacin in the treatment of adults with CABP (Pneumonia Outcomes Research Team [PORT] Risk Class II, III, or IV). PORT Risk Class Calculation was adapted from Fine et al., *N. Engl. J. Med.* 336:243-250, 1997 (incorporated by reference). About 750 patients were enrolled. Both iv and po phases of the study were double-blind. Enrollment of subjects with disease characterized as PORT Risk Class II were limited to no more than 15% of randomized subjects. Enrollment of subjects who have received a single dose of an allowed short-acting antibiotic within the 72 hours prior to the first dose of test article were limited to no more than 25% of randomized subjects. Enrolled subjects participated in the study for approximately 30 days.

The study consists of 3 phases: Screening, Double-Blind Treatment, and Follow-up. Screening evaluations, with the exception of the blood culture sample collection and radiographic confirmation of pneumonia, were completed within the 24 hours prior to randomization. The blood culture sample collection and radiographic confirmation of pneumonia were completed within the 24 hours prior to the first dose of test article. Following Screening, eligible subjects who meet inclusion criteria, and do not meet exclusion criteria were randomly assigned to a treatment group to receive 7 to 14 days of treatment with either Compound 1 or moxifloxacin. The randomized subjects received their first dose of test article within 4 hours after randomization.

The comparator drug for this study is selected to be moxifloxacin (400 mg iv q24 h with the option to transition to 400 mg po q24 h), given the wide acceptance of fluoroquinolone monotherapy as a safe, first-line option for treating subjects with CABP. Moxifloxacin provides a broad spectrum of activity against respiratory pathogens that are causative agents of CABP, including typical (e.g., *Streptococcus pneumoniae*) and atypical (e.g., *Legionella, Chlamydophila,* and *Mycoplasma* spp.) pathogens, with a similar spectrum of activity to that of Compound 1. Like Compound 1, moxifloxacin has both iv and po formulation options and was administered once daily.

A post therapy evaluation visit occurred approximately 5 to 10 days after the last dose of test article and a follow-up telephone contact occurred approximately 30 to 37 days after the first dose of test article. Details of the study are further described below.

As used herein, "post therapy evaluation," "post treatment evaluation," and "PTE," are used interchangeably herein throughout the application without distinction in meaning.

Dosing Regimen:

Compound 1 was administered as 100 mg iv q12 h for 2 doses, followed by 100 mg iv q24 h (starting 24 h after first dose), with the option to switch to 300 mg po q24 h after a minimum of 3 days (4 doses) of iv treatment.

The comparator drug Moxifloxacin was administered as 400 mg iv q24 h (with a single placebo infusion to match the Compound 1 dosing regimen 12 hours after the first dose on Day 1), with the option to switch to 400 mg po q24 h after a minimum of 3 days (4 doses) of iv treatment.

Patient Inclusion/Exclusion Criteria

Patients were male or female 18-years or older. Patients had fulfilled ALL of the following criteria: had at least 3 of the following symptoms: cough, production of purulent sputum, dyspnea (shortness of breath), and pleuritic chest pain; had at least two of the following abnormal vital signs: fever or hypothermia documented by the investigator (temperature >38.0° C. [100.4° F.] or <36.0° C. [95.5° F.]), hypotension with systolic blood pressure (SBP) <90 mm Hg, heart rate >90 beats per minute (bpm), and respiratory rate (RR) >20 breaths/minute; had at least 1 clinical sign or laboratory finding associated with CABP: hypoxemia (partial pressure of arterial oxygen [$PaO_2$]<60 mm Hg by arterial blood gas [ABG] or oxygen saturation <90% by pulse oximetry), physical examination findings of pulmonary consolidation (e.g., dullness on percussion, bronchial breath sounds, or egophony), and an elevated total white blood cell (WBC) count (>12,000 cells/mm$^3$) or leucopenia (WBC <4,000 cells/mm) or elevated immature neutrophils (>15% band forms, regardless of total peripheral WBC count); had radiographically-confirmed pneumonia, i.e., new or progressive pulmonary infiltrate(s) on chest X-ray (CXR) or chest computed tomography (CT) scan consistent with acute bacterial pneumonia within 24 or 48 hours prior to the first dose of test article; and had disease categorized as being PORT Risk Class II, III, or IV at Screening, and were expected to require a minimum of at least 3 days of iv therapy for the initial treatment of CABP.

Females patients had a negative urine pregnancy test at Screening and agreed to comply with using an acceptable method of birth control as per local requirements from Screening through post therapy evaluation (PTE). Males agreed to use an acceptable method of birth control with female partner(s) and did not donate sperm from Screening through PTE.

Patients with any of the following conditions were not allowed in the trial: had received one or more dose(s) of a potentially effective systemic antibacterial treatment within the 72 hours prior to the first dose of test article (a subject was considered to have received a potentially effective systemic antibacterial treatment if the pathogen identified as causing infection was shown to be susceptible to the antibacterial given or, in the circumstance where a pathogen was not identified, if the antibacterial agent was approved for treatment of pneumonia or was known to have activity against any of the leading causes of CABP (e.g., *Streptococcus pneumoniae, Haemophilus influenzae, Moraxella catarrhalis, Staphylococcus aureus, Legionella pneumophila*). One exception was that subjects may be eligible despite prior antibacterial therapy if they had been treated with a single dose of a short-acting antibacterial (i.e., an antibacterial whose standard dosing regimen was more frequent than once per day); was known or suspected to have CABP caused by a pathogen that may be resistant to either test article (e.g., *Klebsiella pneumoniae, Pseudomonas aeruginosa, Pneumocystis jiroveci*, obligate anaerobes, mycobacteria, fungal pathogens); suspected or confirmed empyema (a parapneumonic pleural effusion was not an exclusion criteria) or lung abscess; subjects with known or suspected hospital-acquired pneumonia (HAP) or healthcare-associated pneumonia (HCAP). HAP was defined as pneumonia with onset of clinical signs and symptoms ≥48 hours after hospitalization in an acute in-subject health care facility. HCAP was defined as pneumonia acquired in a long-term care or subacute/intermediate healthcare facility (e.g., nursing home) or in a subject admitted with pneumonia following a recent hospitalization (discharged within 90 days of current admission and previously hospitalized for ≥48 hours); had known or was clinically suspected to have 1 or more of the following prior to randomization: alanine aminotransferase (ALT) or aspartate aminotransferase (AST) ≥2× Upper Limit of Normal (ULN), total bilirubin >1.5×ULN, or evidence of end-stage liver disease (e.g., ascites, hepatic encephalopathy); had a known history of having experienced unstable cardiac disease (e.g., unstable angina, myocardial infarction, acute congestive heart failure, unstable cardiac arrhythmia, etc.) within the 3 months prior to Screening; had a QT interval corrected for heart rate using Fridericia's formula (QTcF) >450 msec (males) or >470 msec (females), were known to have long QT syndrome, used drugs of potential proarrhythmic or QT prolonging effect, and/or presented with tachyarrhythmia; required any form of dialysis (e.g., hemodialysis, peritoneal dialysis); history or evidence of severe renal disease or had a calculated creatinine clearance (CrCl) of <30 mL/minute, using the Cockcroft-Gault equation; evidence of significant immunological disease determined by any of the following: current or anticipated neutropenia defined as <500 neutrophils/mm$^3$, known infection with Human Immunodeficiency Virus (HIV) and a cluster of differentiation 4 (CD4) count that was unknown or documented to be <200 cells/mm$^3$ within the last year, or an Acquired Immune Deficiency Syndrome (AIDS)-defining illness; the receipt of cancer chemotherapy, radiotherapy, or potent, non-corticosteroid immunosuppressant drugs (e.g., cyclosporine, azathioprine, tacrolimus, immune-modulating monoclonal antibody therapy, etc.) within the past 3 months, or the receipt of corticosteroids equivalent to or greater than 40 mg of prednisone per day or for more than 14 days in the prior 30 days; required acute pharmacologic intervention to stabilize blood pressure (BP) and/or adequate tissue perfusion, OR had evidence of septic shock defined by ALL of the following: fever or hypothermia documented by the investigator (temperature >38.0° C. [100.4° F.] or <36.0° C. [95.5° F.]), heart rate >90 beats/minute, RR >20 breaths/minute, WBC >12,000 cells/mm$^3$ or <4,000 cells/mm$^3$ or >10% immature (band) forms, regardless of the total peripheral WBC count, hypotension with SBP <90 mm Hg despite an iv fluid challenge of 20-30 cc/kg over a 30 minute period, and perfusion abnormalities that may included, but were not limited to, lactic acidosis (blood lactate concentration ≥4 mmol/L), oliguria, or acute alteration in mental status; known or suspected primary or metastatic neoplastic lung disease, aspiration pneumonia, active tuberculosis, cystic fibrosis, bronchiectasis, bronchial obstruction (e.g., post-obstructive pneumonia), chronic neurological disorder preventing clearance of pulmonary secretions, or severe chronic obstructive pulmonary disease (COPD); pregnant or nursing (breastfeeding) women; had a history of hypersensitivity or allergic reaction (e.g., anaphylaxis, urticaria, other significant reaction) to any tetracycline (e.g., minocycline, doxycycline or tigecycline) or to any fluoroquinolone antibiotic; had a history of pseudotumor cerebri, or prior (within 2 weeks prior to Screening) or planned concomitant use of isotretinoin; had a history of systemic lupus erythematosus or lupus-like syndrome; had current evidence of pancreatitis; had a history of a central nervous system disorder that may predispose to seizures or lower the seizure threshold; use of other investigational drugs within 5 half-lives or 30 days prior to Screening, whichever was longer; had previously been treated with Compound 1 or previously enrolled in this study; any planned medical intervention that might interfere with the ability to comply with the study requirements; and had a life expectancy of less than or equal to 3 months or any concomitant condition that, in the opinion of the investigator, was likely to interfere with evaluation of the response of the infection under study, determination of adverse events (AEs), or completion of the expected course of treatment.

In addition, no systemic prior or concomitant antibacterial therapy was allowed, other than a single dose of a short-acting antibacterial, within the 72 hours prior to the first dose of test article. All other medications not prohibited by the protocol and considered necessary for the subject's welfare may be administered and/or continued under the supervision of the investigator.

Dosing Regimens

The double-blind treatment period was up to 14 days in duration. Subjects who met inclusion criteria and did not meet exclusion criteria were randomly assigned to a treatment group, and received their first dose of test article within 4 hours after randomization.

The following assessments were done: vital signs, physical examinations (worsening of observations since the Screening examination was recorded as AEs), AEs and SAEs, concomitant treatments, CABP symptom severity scale, microbiological assessments, 12-lead ECG (performed just prior [within 30 minutes] and 30-90 minutes after the start of the first infusion of the first and third doses of test article, at the Day 7 visit, at the EOT visit, and as otherwise clinically indicated), blood for Central Laboratory assessments: hematology, chemistry, pregnancy (for women only), test article administration and accountability, assessment for po switch or need to continue therapy, and investigator's assessment of clinical response.

Subjects were randomized (1:1) to 1 of the following 2 treatment arms:

a. Investigational therapy: Compound 1 (supplied with tosylate acid counter ion, sucrose, hydrochloric acid and sodium hydroxide to adjust the pH), 100 mg iv q12 h (first 2 doses), followed by 100 mg iv q24 h (starting 24 hours after first dose), with the option to switch to 300 mg (two 150 mg Compound 1 tablets and 1 over-encapsulated placebo tablet matching moxifloxacin) po q24 h after at least 3 days (4 doses) of iv treatment.

b. Reference therapy: moxifloxacin, 400 mg iv q24 h (with a single placebo infusion to match the Compound 1 dosing regimen 12 hours after the first dose on Day 1) with the option to switch to 400 mg (one 400 mg moxifloxacin over-encapsulated tablet and 2 placebo tablets matching Compound 1 tablets) po q24 h after at least 3 days (4 doses) of iv treatment.

The iv treatment phase (minimum of 3 days, 4 doses) followed a double-dummy design with placebo infusions matched to active Compound 1 and moxifloxacin infusions as shown in Table 3-1 below. Infusions of Compound 1 and matched placebo were administered continuously over approximately 30 minutes. During the first 24 hours of iv treatment, subjects on the moxifloxacin treatment arm received a placebo infusion to match the t=12 h infusion in the Compound 1 arm as shown in the table.

Infusions of moxifloxacin and matched placebo were administered continuously over approximately 60 minutes. All infusion start and stop times were recorded.

TABLE 3-1

Treatment Regimens for IV Test Article

| Infusion Regimen$^a$ | Compound 1 Arm$^{b,c}$ | Moxifloxacin Arm$^{b,c}$ |
| --- | --- | --- |
| t = 0 h$^d$ | Compound 1 100 mg in 100 mL NS | 100 mL NS placebo |
|  | 250 mL NS placebo | moxifloxacin 400 mg in 250 mL 0.8% saline |
| t = 12 h | Compound 1 100 mg in 100 mL NS | 100 mL NS placebo |
| t = 24 h$^d$ | Compound 1 100 mg in 100 mL NS | 100 mL NS placebo |
|  | 250 mL NS placebo | moxifloxacin 400 mg in 250 mL 0.8% saline |
| t = 48 h$^d$ | Compound 1 100 mg in 100 mL NS | 100 mL NS placebo |
|  | 250 mL NS placebo | moxifloxacin 400 mg in 250 mL 0.8% saline |

TABLE 3-1-continued

Treatment Regimens for IV Test Article

| Infusion Regimen[a] | Compound 1 Arm[b,c] | Moxifloxacin Arm[b,c] |
|---|---|---|
| t = 72 h[e], then q24h[d] | Compound 1 100 mg in 100 mL NS<br>250 mL NS placebo | 100 mL NS placebo<br>moxifloxacin 400 mg in 250 mL 0.8% saline | t = time;
NS = Normal saline (0.9% sodium chloride) for injection;
q12h = every 12 hours;
q24h = every 24 hours.
[a]The start time of the first infusion was designated time 0 (t = 0 h), followed by 2 q12h doses (t = 12 h, t = 24 h), and then all subsequent doses were q24h for a minimum of 3 days, 4 doses of iv treatment (through t = 48 h).
[b]All 100 mL infusions of Compound 1 or 100 mL NS placebo were administered continuously over 30 minutes (at least 30 minutes and not more than 45 minutes).
[c]All 250 mL infusions of moxifloxacin or 250 mL NS placebo were administered continuously over approximately 60 minutes.
[d]At these time points a 100 mL infusion was administered first, followed by a 250 mL infusion.
[e]Beginning with the fifth dose (t = 72 h), based on the investigator decision the therapy could be iv or was switched to po therapy. Note, the first po dose should be administered in the morning, 12-24 hours after the last iv dose, therefore the first po dose might have occurred as early as t = 60 h.

A representative (but none limiting) illustration of the above treatment regimen for Compound 1 is provided below:

|  | Day 1 |  | Day 2 | Day 3 | Day 4 and Beyond |
|---|---|---|---|---|---|
|  | 0 hr | 12 hr | 24 hr | 48 hr | 72 hr- |
| Compound 1 | 100 mg IV | 100 mg IV | 100 mg IV | 100 mg IV | After Day 3, either 100 mg IV or 300 mg oral q24h |

Total duration of treatment (IV+oral (if present)) is typically 7-14 days.

While the subject was receiving iv therapy, the investigator assessed the subject daily and chose ONE of the following based on the overall clinical assessment of the subject:

(1) continue iv test article;
(2) switch to po test article (after a minimum of 3 days [4 doses] of iv therapy) Note, the first po dose was administered in the morning, 12-24 h after the last iv dose, therefore the first po dose may occur as early as t=60 h;
(3) discontinue test article—this decision prompted the EOT evaluation.

Each daily decision was recorded.

At all times during the study the decision to continue iv, switch to po, or discontinue test article was made based on the clinical judgment of the investigator. The investigator may have used the culture and susceptibility results from the local microbiology laboratory to help guide therapy; however, decisions to continue or discontinue test article was based on clinical response rather than susceptibility results (as Compound 1 susceptibility testing was not available at the local site). If the CABP was caused by a microorganism that was not susceptible to moxifloxacin in vitro, the decision to continue or discontinue study treatment was based on the subject's clinical course and the investigator's clinical judgment. The rationale for this decision was recorded.

The decision to switch to po treatment was made by the investigator. For a subject to be considered clinically stable and meet criteria for transition to a po regimen, they must have had the following findings noted and recorded:

a. Temperature ≤37.8° C. (100° F.)
b. Heart rate ≤100 beats/minute
c. RR ≤24 breaths/minute
d. SBP ≥95 mm Hg
e. Oxygen saturation ≥90% as measured by pulse oximetry or $PaO_2$≥60 mm Hg by ABG
f. No worsening of CABP symptoms (cough, sputum production, pleuritic chest pain, dyspnea) compared to Screening
g. Normal mental status ("absence of confusion" or pre-illness Baseline for subjects who did not have normal mental status before onset of pneumonia)
h. Ability to maintain po intake.

Switch to po was not permitted until after the subject had completed at least the first 3 days of iv treatment (after 4 iv doses).

The date and time the investigator confirmed the criteria for the subject's eligibility for po treatment were met and made the decision to switch to po treatment was recorded. For subjects that had been switched to po test article and discharged from the hospital prior to study Day 6, visits were conducted on study Days 4 and 5, while a study Day 6 visit was optional.

Treatment regimens for po dosing were shown in Table 3-2. When switching from iv to po test article the recommended interval between doses was maintained. The first po dose, for both Compound 1 and moxifloxacin treatment arms, was given in the morning 12 to 24 hours after the last iv dose. The po treatment phase also employed a double-blind, double-dummy design using Compound 1 placebo comparator tablets of matching size and shape to active Compound 1 tablets and matching over-encapsulated placebo and active moxifloxacin tablets.

The tablets had excipients including lactose monohydrate, microcrystalline cellulose, sodium stearyl fumarate, crospovidone, colloidal silicon dioxide, sodium bisulfite, polyvinyl alcohol, titanium dioxide, talc, soya lecithin, xanthan gum, FD&C Yellow #6 and FD&C #2. The Compound 1 tablets were taken with water in a fasting state (no food, antacids or multivitamins containing multivalent cations (e.g., aluminum, magnesium, calcium, bismuth, iron, or zinc) or drink except water for at least 6 hours). After dosing, no food was to be consumed for 2 hours; no dairy products, antacids or multivitamins containing multivalent cations (e.g., aluminum, magnesium, calcium, bismuth, iron, or zinc) for 4 hours.

TABLE 3-2

Treatment Regimens for Oral Test Article

| a) Time of Dosing | b) Compound 1 Arm | c) Moxifloxacin Arm | d) Dosing Condition[a,b] |
|---|---|---|---|
| Morning | Two 150 mg tablets and 1 over-encapsulated placebo tablet resembling moxifloxacin | One 400 mg over-encapsulated tablet and 2 placebo tablets resembling Compound 1 tablets | Fasting overnight (no food or drink except water for at least 6 hours) before dosing; after dosing, no food for 2 hours, no dairy products for 4 hours |

[a]All doses of po test article were taken with water.
[b]All subjects were instructed to avoid taking antacids and multivitamins containing multivalent cations (e.g., aluminum, magnesium, calcium, bismuth, iron, or zinc) while taking po test article.

While the subject was receiving po therapy, the investigator assessed the subject on study Day 7, 10 and 14 and choose 1 of the following actions:
a. continue po test article;
b. discontinue test article—this decision prompted the EOT evaluation.

The investigator may have used the culture and susceptibility results from the local microbiology laboratory to help guide therapy; however, decisions to continue or discontinue test article was based on clinical response rather than susceptibility results (as Compound 1 susceptibility testing was not available at the local site). If the CABP was caused by a microorganism that was not susceptible to moxifloxacin in vitro, the decision to continue or discontinue study treatment was based on the subject's clinical course and the investigator's clinical judgment.

No dose adjustments and interruptions of test article were permitted.

Subjects were evaluated at 2 visits after the completion of treatment: at the PTE 5 to 10 days after the last treatment day, and at a Final Follow-up assessment 30 to 37 days after the first dose of treatment.

The following table summarizes the study drug exposure in the safety population.

| Characteristics | Compound 1 (N = 382) | Moxifloxacin (N = 388) | All Subjects (N = 770) |
|---|---|---|---|
| Duration of exposure on therapy (days) | | | |
| n | 382 | 388 | 770 |
| Mean (SD) | 9.6 (2.88) | 9.6 (2.94) | 9.6 (2.91) |
| Medium | 10.0 | 10.0 | 10.0 |
| Min, Max | 1, 14 | 1, 17 | 1, 17 |
| Duration of exposure on therapy (days), n (%) | 382 | 388 | 770 |
| 0 | 0 | 0 | 0 |
| 1-3 | 17 (4.5) | 17 (4.4) | 34 (4.4) |
| 4-6 | 10 (2.6) | 17 (4.4) | 27 (3.5) |
| 7-10 | 238 (62.3) | 218 (56.2) | 456 (59.2) |
| 11-14 | 117 (30.6) | 134 (34.5) | 251 (32.6) |
| >14 | 0 | 2 (0.5) | 2 (0.3) |
| Number of days of IV therapy | | | |
| n | 382 | 388 | 770 |
| Mean (SD) | 5.7 (2.51) | 5.7 (2.54) | 5.7 (2.52) |
| Medium | 5.0 | 5.0 | 5.0 |
| Min, Max | 1, 14 | 1, 14 | 1, 14 |
| Number of days of IV therapy, n (%) | 382 | 388 | 770 |
| 0 | 0 | 0 | 0 |
| 1-2 | 15 (3.9) | 13 (3.4) | 28 (3.6) |
| 3-6 | 222 (58.1) | 232 (59.8) | 454 (59.0) |
| 7-10 | 134 (35.1) | 130 (33.5) | 264 (34.3) |
| 11-14 | 11 (2.9) | 13 (3.4) | 24 (3.1) |
| >14 | 0 | 0 | 0 |
| Number of days of IV therapy prior to oral switch | | | |
| n | 295 | 294 | 589 |
| Mean (SD) | 5.0 (2.02) | 5.0 (2.08) | 5.0 (2.04) |
| Medium | 4.7 | 4.7 | 4.7 |
| Min, Max | 2, 13 | 2, 11 | 2, 13 |
| Subjects switching to oral therapy, n (%) | 295 (77.2) | 294 (75.8) | 589 (76.5) |
| Day of oral switch, n (%) | 295 | 294 | 589 |
| 1-3 | 1 (0.3) | 1 (0.3) | 2 (0.3) |
| 4-5 | 130 (44.1) | 132 (44.9) | 262 (44.5) |
| 6-7 | 80 (27.1) | 81 (27.6) | 161 (27.3) |
| ≥8 | 84 (28.5) | 80 (27.2) | 164 (27.8) |
| Number of days of oral therapy | | | |
| n | 295 | 294 | 589 |
| Mean (SD) | 5.1 (1.93) | 5.2 (2.04) | 5.2 (1.98) |

| Characteristics | Compound 1 (N = 382) | Moxifloxacin (N = 388) | All Subjects (N = 770) |
|---|---|---|---|
| Medium | 5.0 | 5.0 | 5.0 |
| Min, Max | 1, 11 | 1, 14 | 1, 14 |
| Number of days of oral therapy, n (%) | 295 | 294 | 589 |
| 0 | 0 | 0 | 0 |
| 1-4 | 132 (44.7) | 132 (44.9) | 264 (44.8) |
| 5-7 | 152 (51.5) | 147 (50.0) | 299 (50.8) |
| 8-11 | 11 (3.7) | 14 (4.8) | 25 (4.2) |
| >11 | 0 | 1 (0.3) | 1 (0.2) |

Note:
Both active test article and placebo are included.
Percentages for IV summaries are based on subjects receiving at least one IV dose. Percentages for oral summaries are based on subjects receiving at least one oral dose. Percentages for subjects who switched from IV to oral are based on the number who switched (e.g., 295 for Compound 1).
Note:
Duration of study drug exposure in days = Date of last IV or oral dose − Date of first IV dose + 1. Number of days of IV therapy (IV dosing) prior to oral switch = Date of last IV dose − Date of first IV dose + 1.

Criteria for switching from IV to oral treatment include: Temperature ≤37.8° C. (100° F.); Heart rate ≤100 beats/minute; Respiratory Rate <=24 breaths/minute; Systolic Blood Pressure ≥95 mmHg; Oxygen saturation ≥90% by pulse oximetry or $PaO_2 \geq 60$ mmHg by ABG; No worsening of CABP symptoms compared to screening; Normal Mental Status; and Ability to maintain PO intake. For patients administered Compound 1, 100% of the 295 patients who switched from IV dose to oral dose satisfied each of the above criteria.

Safety Evaluation

Any subject who received test article were included in the evaluation for safety.

Safety evaluations of the enrolled subjects included physical exams, vital signs (blood pressure, pulse rate, body temperature), AEs and SAEs, laboratory assessments (hematology, serum chemistry, urinalysis), 12-lead electrocardiogram (ECG) evaluations, and pregnancy assessments.

After Screening, a physical examination was conducted on the study days and at the EOT and PTE visits. Any new clinically significant finding occurs (i.e., not noted at Screening) after the Screening exam was captured as an AE.

Vital signs including body temperature, BP, pulse/heart rate, and RR were recorded prior to each dose while the subject was on iv treatment.

Blood samples for hematology, chemistry and coagulation (prothrombin time only) were drawn at Screening, Day 4, Day 7, Day 10, EOT, and PTE.

Safety studies included a standard 12-lead ECG at the following times: screening, just prior (within 30 minutes) to the start of the first infusion of the first dose of test article (t=0 h), 30-90 minutes after the start of the first infusion of the first dose of test article, just prior (within 30 minutes) to the start of the first infusion of the third dose of test article (t=24 h), 30-90 minutes after the start of the first infusion of the third dose of test article, at the Day 7 visit, at the EOT visit, and in any case in which a subject developed an AE of non-pleuritic cardiac chest pain, palpitations, tachyarrhythmia or as otherwise clinically indicated.

Safety studies also included pregnancy and assessments of fertility. All women had a urine pregnancy test at the site at the Screening visit. No one was enrolled if a positive urine pregnancy test result was obtained. A serum sample for β-hCG testing was also collected at the Screening visit and sent to the Central Laboratory for confirmation of the urine pregnancy results. Serum samples for β-hCG testing at the Central Laboratory were also collected at EOT and PTE. Test article administration was discontinued if a positive β-hCG result was reported by the Central Laboratory after a woman was enrolled.

Safety studies also included two sets of blood cultures collected within the 24 hours prior to the first dose of test article. Each set of blood cultures were collected by direct venipuncture from independent body sites 15-30 minutes apart. If bacteria were isolated from baseline blood cultures, repeat blood cultures were collected on the day that the positive blood culture is detected. If subsequent blood cultures were also positive, the blood cultures were repeated as necessary until negative blood cultures were obtained.

Efficacy Evaluation

In order to satisfy different health authority requirements, the primary variables were tested with 2 response endpoints:

Successful Early Clinical Response or ECR (72-120 hours after first dose) was determined programmatically and defined as survival with improvement in at least 2 of 4 subject symptoms (cough, sputum production, pleuritic chest pain, dyspnea), as assessed by the investigator, without deterioration in any of these 4 symptoms (FDA primary efficacy point). One such evaluation was done in the ITT population.

Successful Investigator's Assessment of Clinical Response at the PTE visit, defined as survival after completion of a test article regimen, with resolution of signs and symptoms of the infection to the extent that further antibacterial therapy was not necessary (EMA primary efficacy point). One of such evaluation was done in both the ITT and CE populations, limited to PORT Risk Class III/IV subjects. In addition, 97.5% CI was used in addition to the 95% CI level for 10% non-inferiority assessment.

The Early Clinical Response endpoint was tested in the intent-to-treat (ITT) analysis population. The Investigator's Assessment of Clinical Response at PTE endpoint was tested in the ITT and clinically evaluable (CE) populations (co-primary endpoints).

Secondary efficacy variables included:

Response category for Early Clinical Response

Clinical Response category for Investigator's Assessment of Clinical Response at EOT and PTE Clinical Response category according to the identified causative pathogen The following is a list of key assessments that was performed:

Assessment of signs and symptoms of CABP by the investigator

Microbiological assessment of the infection

Assessment of clinical response

Each of the key assessments is described in further detail below.

a) Assessment of CABP Symptom Severity

The assessment of CABP symptoms observed by the investigator was conducted at every scheduled evaluation with the exception of the Final Follow-up assessment. The investigator specifically assessed the severity level of the subject's symptoms of cough, sputum production, pleuritic chest pain and dyspnea on a 4 point scale (absent, mild, moderate, or severe) based upon the Community Acquired Bacterial Pneumonia Subject Symptom Severity Guidance Framework for Investigator Assessment (see below) and entered the symptom severity scores into the eCRF. For subjects that had been switched to po test article and discharged from the hospital prior to study Day 6, visits were conducted on study Days 4 and 5, while a study Day 6 visit was optional.

CABP Subject Symptom Severity Guidance Framework for Investigator Assessment

| Absent | Mild | Moderate | Severe |
|---|---|---|---|
| COUGH? | | | |
| No cough or resolution (to pre-CABP Baseline) | Cough present but it does not interfere with subject's usual daily activities | Cough present, frequent and it does interfere with some of the subject's usual daily activities | Cough is present throughout the day and night; it limits most of the subjects' usual daily activities and sleep patterns |
| PLEURITIC CHEST PAIN? | | | |
| No chest pain or resolution of chest pain related to CABP | Chest pain present occasionally with deep breathing but it does not interfere with subject's usual daily activities | Chest pain is present with normal breaths and it does interfere with the subject's usual daily activities | Chest pain is present at rest and/or with shallow breathing; it limits most of the subject's usual daily activities |
| SHORTNESS OF BREATH? | | | |
| No shortness of breath or resolution (to pre-CABP Baseline) | Shortness of breath with strenuous activities only but it does not interfere with subject's usual daily activities | Shortness of breath with usual activities and it does interfere with the subject's usual daily activities | Shortness of breath with minimal exertion or at rest; it limits most of the subject's usual daily activities |
| PHLEGM/SPUTUM PRODUCTION? | | | |
| No coughing up of phlegm/sputum or resolution (to pre-CABP Baseline) | Subject coughs up a small amount of phlegm/sputum | Subject coughs up a moderate amount of phlegm/sputum | Subject coughs up a large amount of phlegm/sputum | b) Microbiological Assessments

Microbiological assessments included respiratory culture and Gram stain, urine test for *Legionella pneumophila* and *Streptococcus pneumoniae* antigen screening, and serology test for *Legionella pneumophila*, *Mycoplasma pneumoniae* and *Chlamydophila pneumoniae* titers.

For respiratory culture and Gram stain, at the Screening visit collection of an adequate quality expectorated or induced sputum or other respiratory specimen reflecting fluid from the lower respiratory tract (e.g., respiratory fluid obtained by bronchioalveolar lavage or bronchoscopy; pleural fluid obtained by thoracentesis; or expectorated or induced sputum meeting adequacy criteria) was attempted from all subjects and submitted to the local microbiology laboratory for Gram stain and culture. The date, time and type of specimen submitted were recorded. An adequate quality sputum specimen was defined as having the following 2 findings as reported by the local laboratory:

1. <10 Squamous epithelial cells/low power field (lpf) (i.e., 100×)
2. >25 Polymorphonuclear cells/lpf (i.e., 100×)

Adequate quality sputum specimens and other Screening respiratory specimens for culture were obtained prior to first dose of test article. At the EOT and/or PTE visit, respiratory specimen cultures and Gram stains were obtained only for subjects who were Clinical Failures and required alternative antibacterial treatment for CABP.

Laboratory reports on Gram stains included a semi-quantitative description of the number of polymorphonuclear leukocytes per low power field (i.e., 100×) and a description of bacteria seen. For Gram stains of respiratory specimens a semi-quantitative description of the number of squamous epithelial cells per low power field (i.e., 100×) was included.

Culture results included identification of all pathogens to the level of genus and species. Susceptibility testing for moxifloxacin (or other fluoroquinolones) was performed using a standard method.

All isolates identified from expectorated or induced sputum specimens meeting the 2 criteria that define the specimen as being of adequate quality and/or that were isolated from respiratory specimens or blood and were potential pathogens were submitted to the Central Laboratory for verification of genus and species and for standardized minimum inhibitory concentration (MIC) testing performed for Compound 1, moxifloxacin and a panel of currently approved antibiotics.

Regarding urine tests for *Legionella pneumophila* and *Streptococcus pneumoniae* antigen screening, urine was collected at the Screening visit to test for the presence of *Legionella pneumophila* and *Streptococcus pneumoniae* antigens.

Regarding serology test for *Legionella pneumophila*, *Mycoplasma pneumoniae* and *Chlamydophila pneumoniae* titers, blood samples were collected to conduct serology for *Legionella pneumophila*, *Mycoplasma pneumoniae* and

*Chlamydophila pneumoniae* by the Central Laboratory at the Screening visit, and at the PTE visit.

c) Assessment of Clinical Outcome

Assessment of clinical outcome occurred at Early Clinical Response assessment (programmatically), EOT, and PTE as described below.

1. Evaluation of the Infection Under Study at the Early Clinical Response Assessment The formal determination of the response to therapy at the Early Clinical Response assessment (72 to 120 hours after administration of the first dose of test article) was done programmatically using the investigator's assessment of the subject's symptoms associated with CABP entered into the eCRF. The investigator was not responsible for categorizing subjects as Clinical Success, Failure, or Indeterminate at the Early Clinical Response assessment. The severity of the subject CABP symptoms of cough, sputum production, pleuritic chest pain and dyspnea was evaluated on a 4-point scale (absent, mild, moderate, or severe) based upon the Community Acquired Bacterial Pneumonia Subject Symptom Severity Guidance Framework for Investigator Assessment. A CABP subject symptom severity assessment was completed at every scheduled evaluation with the exception of the Final Follow-up assessment. For subjects that had been switched to po test article and discharged from the hospital prior to study Day 6, visits was conducted on study Days 4 and 5, while a study Day 6 visit was optional.

Clinical Success: at the Early Clinical Response assessment was defined as survival with improvement of at least 1 level (i.e., severe to moderate, moderate to mild, mild to absent) compared to Screening in 2 CABP symptoms (cough, sputum production, pleuritic chest pain and dyspnea) with no worsening by at least 1 level in the other inclusion CABP symptoms. In order for the subject to be considered a Clinical Success, the subject may not meet any criteria for Clinical Failure or Indeterminate Early Clinical Response.

Clinical Failure: defined as meeting any of the following criteria:

There was no improvement by at least 1 level (i.e., severe to moderate, moderate to mild, mild to absent) compared to Screening in 2 CABP symptoms.

Any of the 4 CABP symptoms was worse (by at least 1 level) compared to Screening.

The subject required alternative (rescue) antibacterial treatment for CABP prior to the Early Clinical Response assessment related to either (a) progression or development of new symptoms attributable to CABP or (b) development of infectious complications of CABP (e.g., empyema, lung abscess).

The subject was receiving antibacterial therapy that may be effective for the infection under study for a different infection from the 1 under study.

Discontinued study therapy due to an AE and received alternative antibacterial treatment for CABP prior to the Early Clinical Response assessment.

Death prior to the Early Clinical Response assessment.

Indeterminate: the clinical response to test article can not be adequately inferred due to:

Subject was not seen for the evaluation because they withdrew consent, were lost to follow-up, other reason (specify).

Other specified reason.

2. Clinical Evaluation of the Infection Under Study at EOT

EOT assessments were performed on the calendar day of, or within 2 days following the last dose of any test article. If a subject withdrew prematurely or terminated participation in the study prior to completion of the planned antibiotic therapy, the EOT visit was conducted.

The investigator determined whether or not the subject met the criteria of 1 of the following clinical outcomes:

Clinical Success: the subject was alive and the infection was sufficiently resolved such that further antibacterial therapy was not needed. These subjects may have some residual findings related to infection (i.e., cough) requiring ancillary (i.e., non-antibiotic) treatment (e.g., expectorant). In order for the subject to be considered a Clinical Success at EOT, the subject may not meet any criteria for Clinical Failure or Indeterminate at EOT.

Clinical Failure: the subject required alternative antibacterial treatment for CABP prior to EOT related to either (a) progression or development of new symptoms of CABP or (b) development of infectious complications of CABP (e.g., empyema, lung abscess) or (c) subject developed an AE that required discontinuation of study therapy. Other reasons for Clinical Failure are:

Subject was receiving antibacterial therapy that may be effective for the infection under study for a different infection from the 1 under study.

Death prior to EOT visit.

Indeterminate: the clinical response to test article could not be adequately inferred due to:

Subjects were not seen for EOT evaluation because they withdrew consent, were lost to follow-up, other reason (specify).

Other specified reason.

3. Clinical Evaluation of the Infection Under Study at PTE

The PTE assessment was performed 5 to 10 days after the subject's last day of therapy. The investigator determined whether or not the subject met the criteria of 1 of the following clinical outcomes:

Clinical Success: survival after completion of a test article regimen without receiving any systemic antibacterial therapy other than test article, resolution of signs and symptoms of the infection present at Screening with no new symptoms or complications attributable to CABP and no need for further antibacterial therapy.

Clinical Failure: the subject required alternative antibacterial treatment for CABP prior to PTE related to either (a) progression or development of new symptoms of CABP or (b) development of infectious complications of CABP (e.g., empyema, lung abscess).

The subject was receiving antibiotics that may be effective for the infection under study for a different infection from the 1 under study.

Death prior to PTE.

Indeterminate: the clinical response to test article could not be adequately inferred due to:

Subjects were not seen for PTE evaluation because they withdrew consent, were lost to follow-up, other (specify).

Other specified reason.

d) Pharmacokinetic Plasma Samples for Compound 1 Concentration

PK data was analyzed using a population PK model. PK samples were collected using a sparse sampling method for the population PK model. The number of samples and collection schedule varied for individual subjects. Up to 4 samples were collected per subject between study Days 1 to 7. Blood was collected either by fresh venipuncture or via a cannula used SOLEY for that purpose (PK samples were NOT drawn through the same iv access used for administration of test article). The dates and times for all doses of test article and PK sample collections were recorded. For intravenously administered doses of test article, the start and stop times for each infusion were recorded. The sample tube were centrifuged at 1500×g for 10 minutes and the separated plasma transferred in 2 equal aliquots into pre-labeled tubes;

and the tubes frozen at −70° C. within 60 minutes of collection. The time the sample was frozen was recorded to the nearest minute. All of the PK samples from a single subject were collected and frozen at −70° C. and shipped frozen at −70° C. to the Central Laboratory. The samples were assayed at Analytical Laboratory for Compound 1 using a specific, sensitive and validated Liquid Chromatography/Tandem Mass Spectrometry (LC/MS/MS) method.

e) Safety Monitoring—Adverse Events

An AE was defined as any untoward, undesired, or unplanned event in the form of signs, symptoms, disease, or laboratory or physiologic observations occurring in a person given a test article or in a clinical study. The event does not need to be causally related to the test article or clinical study. An AE included, but was not limited to, the following:

Any clinically significant worsening of a preexisting condition.

An AE occurring from overdose of a test article, whether accidental or intentional. Overdose is a dose greater than that specified in the protocol.

An AE occurring from abuse (e.g., use for nonclinical reasons) of a test article.

An AE that had been associated with the discontinuation of the use of a test article.

A SAE is an AE that:

Resulted in death.

Was life-threatening (see below).

Required hospitalization or prolongation of an existing hospitalization (see below).

Resulted in a persistent or significant disability or incapacity (see below).

Resulted in cancer.

Resulted in a congenital anomaly or birth defect.

Additionally, important medical events that may not result in death, be life-threatening, or require hospitalization may be considered SAEs when, based on appropriate medical judgment, they may jeopardize the subject and may require medical or surgical intervention to prevent 1 of the outcomes listed in this definition. Examples of such events included allergic bronchospasm requiring intensive treatment in an emergency room or at home, blood dyscrasias or convulsions that did not result in hospitalization, or development of drug dependency or drug abuse.

A protocol-related AE was defined as an AE occurring during a clinical study that was not related to the test article, but was considered by the investigator or the Medical Monitor (or designee) to be related to the research conditions, i.e., related to the fact that a subject was participating in the study. For example, a protocol-related AE may be an untoward event related to a medical procedure required by the protocol.

Certain information, although not considered an SAE, must be recorded, reported, and followed up as indicated for an SAE. This included: pregnancy exposure to a test article, lactation exposure to a test article with or without an AE, overdose of a test article as specified in this protocol with or without an AE, and inadvertent or accidental exposure to a test article with or without an AE.

Data Analysis

All analyses of data for this study complied with International Conference on Harmonisation of Technical Requirements for Registration of Pharmaceuticals for Human Use (ICH-E9) and the sponsor's guidance documents and standards. Statistical analyses were performed using Statistical Analysis Software (SAS).

a) Analysis Populations

A number of subject populations had been defined for the various analyses of efficacy and safety, as follows:

The ITT population consisted of all randomized subjects.

The microbiological intent-to-treat (microITT) population consisted of subjects in the ITT population who had at least 1 causative pathogen identified at Screening from culture of a respiratory specimen (e.g., respiratory fluid obtained by bronchioalveolar lavage or bronchoscopy; pleural fluid obtained by thoracentesis; or expectorated or induced sputum meeting adequacy criteria), culture of blood, or from a culture-independent method (e.g., positive urinary antigen test for *Streptococcus pneumoniae* or *Legionella pneumophila*, or positive serology for *Legionella pneumophila*, *Mycoplasma pneumoniae* or *Chlamydophila pneumoniae*).

Expanded microITT population was defined using the same criteria as for the microITT population, except that an adequate Gram stain was defined as >10 PMNs/LPF and <10 SECs/LPF for determination of whether an isolate from a sputum culture is a pathogen or not. Here, PMN=Polymorphonuclear; SEC=Squamous Epithelial Cells; LPF=Low Power Field.

The CE population consisted of all ITT subjects who received test article, had a qualifying CABP, an assessment of outcome, and met all other evaluability criteria detailed in the SAP.

The CE-EOT/PTE population consisted of all randomized safety subjects who received any amount of active test article, had completed the investigator's assessment of clinical response at the EOT/PTE visit, with no indeterminate clinical response and met specific criteria related to the required assessments. Here, CE=Clinically Evaluable; EOT=End of treatment; PTE=Post Therapy Evaluation.

The microbiologically evaluable (ME) population included subjects in the CE population who have at least 1 causative pathogen at Screening.

The ME-EOT/PTE consisted of all subjects in both microITT and the CE-EOT/PTE populations.

The Safety population consists of all randomized subjects who receive test article.

The various study populations enrolled in the study, as defined above, are listed below.

| Population | Compound 1 n (%) | Moxifloxacin n (%) | All Subjects n (%) |
| --- | --- | --- | --- |
| ITT | 386 | 388 | 774 |
| Safety | 382 (99.0) | 388 (100.0) | 770 (99.5) |
| microITT | 204 (52.8) | 182 (46.9) | 386 (49.9) |
| Expanded microITT | 218 (56.5) | 198 (51.0) | 416 (53.7) |
| CE-EOT | 357 (92.5) | 357 (92.0) | 714 (92.2) |
| CE-PTE | 340 (88.1) | 345 (88.9) | 685 (88.5) |
| ME-EOT | 193 (50.0) | 172 (44.3) | 365 (47.2) |
| ME-PTE | 188 (48.7) | 169 (43.6) | 357 (46.1) | b) Subject Demographics and Baseline Characteristics

Descriptive statistics, by treatment arm, was provided for the following: Subject disposition (completed test article, discontinued test article by reason for discontinuation, completed study, and discontinued study by reason for discontinuation); Protocol deviations; CABP background information (subject demographics: age (years), gender, race, height (cm), weight (kg), Body Mass Index (BMI) ($kg/m^2$)); PORT Risk Class; and Medical histories and continuing medical conditions.

Baseline demographic and medical variables were analyzed using a 2-sided Fisher's exact test (for categorical variables) or a 2-sided Wilcoxon Rank Sum test (for ordinal and continuous variables).

Selected results of these analysis were compiled in the tables below.

Subject Disposition—ITT Population

| Parameter/Category | Compound 1 (N = 386) n (%) | Moxifloxacin (N = 388) n (%) | All Subjects (N = 774) n (%) | p-value |
|---|---|---|---|---|
| Randomized | 386 (100.0) | 388 (100.0) | 774 (100.0) | |
| Completed Study Treatment[1] | 352 (91.2) | 346 (89.2) | 698 (90.2) | |
| Prematurely Discontinued from Study Treatment | 34 (8.8) | 42 (10.8) | 76 (9.8) | 0.3981 |
| Reason For Premature Discontinuation from Study Treatment | | | | |
| Adverse Event | 17 (4.4) | 28 (7.2) | 45 (5.8) | |
| Lost to Follow-up | 0 | 1 (0.3) | 1 (0.1) | |
| Withdrawal by Subject | 4 (1.0) | 3 (0.8) | 7 (0.9) | |
| Physician Decision | 3 (0.8) | 9 (2.3) | 12 (1.6) | |
| Death | 4 (1.0) | 1 (0.3) | 5 (0.6) | |
| Other | 6 (1.6) | 0 | 6 (0.8) | |
| Completed Study[2] | 356 (92.2) | 362 (93.3) | 718 (92.8) | |
| Prematurely Discontinued from Study | 30 (7.8) | 26 (6.7) | 56 (7.2) | 0.5819 |
| Reason For Premature Discontinuation from Study | | | | |
| Adverse Event | 7 (1.8) | 9 (2.3) | 16 (2.1) | |
| Lost to Follow-up | 0 | 3 (0.8) | 3 (0.4) | |
| Withdrawal by Subject | 7 (1.8) | 8 (2.1) | 15 (1.9) | |
| Physician Decision | 0 | 1 (0.3) | 1 (0.1) | |
| Death | 6 (1.6) | 3 (0.8) | 9 (1.2) | |
| Other | 10 (2.6) | 2 (0.5) | 12 (1.6) | |

[1]Summary of subjects that completed the study treatment.
[2]Summary of subjects that completed the study (i.e., received at least one dose of test article and completed EOT, PTE and Follow-up).

Percentages are based on the ITT population. P-values for differences between treatment groups are from Fisher's exact test. Number of subjects prematurely discontinuing study treatment due to an adverse event may not match counts in adverse events tables as some reasons for discontinuations are coded as death rather than adverse event. Subjects randomized but not treated (total n=4) are counted in the Other category. Total number of deaths are 12 (8 omadacycline and 4 moxifloxacin). EOT=End of Treatment; PTE=Post Treatment Evaluation.

Subject Disposition—CE-PTE Population

| Parameter/Category | Compound 1 (N = 340) n (%) | Moxifloxacin (N = 345) n (%) | All Subjects (N = 685) n (%) | p-value |
|---|---|---|---|---|
| Randomized | 340 (100.0) | 345 (100.0) | 685 (100.0) | |
| Completed Study Treatment[1] | 322 (94.7) | 317 (91.9) | 639 (93.3) | |
| Prematurely Discontinued from Study Treatment | 18 (5.3) | 28 (8.1) | 46 (6.7) | 0.1694 |
| Reason For Premature Discontinuation from Study Treatment | | | | |
| Adverse Event | 12 (3.5) | 19 (5.5) | 31 (4.5) | |
| Lost to Follow-up | 0 | 0 | 0 | |
| Withdrawal by Subject | 0 | 0 | 0 | |
| Physician Decision | 3 (0.9) | 8 (2.3) | 11 (1.6) | |
| Death | 3 (0.9) | 1 (0.3) | 4 (0.6) | |
| Other | 0 | 0 | 0 | |
| Completed Study[2] | 330 (97.1) | 339 (98.3) | 669 (97.7) | |
| Prematurely Discontinued from Study | 10 (2.9) | 6 (1.7) | 16 (2.3) | 0.3234 |
| Reason For Premature Discontinuation from Study | | | | |
| Adverse Event | 4 (1.2) | 2 (0.6) | 6 (0.9) | |
| Lost to Follow-up | 0 | 0 | 0 | |
| Withdrawal by Subject | 1 (0.3) | 0 | 1 (0.1) | |

-continued

| Parameter/Category | Compound 1 (N = 340) n (%) | Moxifloxacin (N = 345) n (%) | All Subjects (N = 685) n (%) | p-value |
|---|---|---|---|---|
| Physician Decision | 0 | 1 (0.3) | 1 (0.1) | |
| Death | 5 (1.5) | 3 (0.9) | 8 (1.2) | |
| Other | 0 | 0 | 0 | |

[1]Summary of subjects that completed the study treatment.
[2]Summary of subjects that completed the study (i.e., received at least one dose of test article and completed EOT, PTE and Follow-up).

Percentages in the table above are based on the CE-PTE population. p-values for differences between treatment groups were from Fisher's exact test. The number of subjects prematurely discontinuing study treatment due to an adverse event may not match counts in adverse events tables as some reasons for discontinuations were coded as death rather than adverse event.

Demographic and Baseline Characteristics—Safety Population

| Characteristics | Compound 1 (N = 382) | Moxifloxacin (N = 388) | All Subjects (N = 770) | p-value |
|---|---|---|---|---|
| Gender, n (%) | | | | |
| n | 382 | 388 | 770 | |
| Female | 177 (46.3) | 169 (43.6) | 346 (44.9) | |
| Male | 205 (53.7) | 219 (56.4) | 424 (55.1) | 0.4689 |
| Race, n (%) | | | | |
| n | 382 | 388 | 770 | |
| White | 353 (92.4) | 355 (91.5) | 708 (91.9) | |
| Black or African American | 11 (2.9) | 7 (1.8) | 18 (2.3) | |
| Asian | 17 (4.5) | 18 (4.6) | 35 (4.5) | |
| American Indian or Alaska Native | 0 | 2 (0.5) | 2 (0.3) | |
| Native Hawaiian or Other Pacific Islander | 0 | 0 | 0 | |
| Other | 1 (0.3) | 6 (1.5) | 7 (0.9) | 0.1762 |
| Ethnicity, n (%) | | | | |
| n | 382 | 388 | 770 | |
| Hispanic or Latino | 8 (2.1) | 14 (3.6) | 22 (2.9) | |
| Not Hispanic or Latino | 370 (96.9) | 370 (95.4) | 740 (96.1) | |
| Not Reported/Unknown | 4 (1.0) | 4 (1.0) | 8 (1.0) | 0.4465 |
| Age (years) | | | | |
| n | 382 | 388 | 770 | |
| Mean (SD) | 60.9 (15.18) | 62.1 (15.21) | 61.5 (15.20) | |
| Median | 61.0 | 63.0 | 62.0 | |
| Min, Max | 19, 97 | 19, 94 | 19, 97 | 0.1394 |
| Categorical Age (years), n (%) | | | | |
| n | 382 | 388 | 770 | |
| 18-45 | 61 (16.0) | 61 (15.7) | 122 (15.8) | |
| >45-65 | 171 (44.8) | 155 (39.9) | 326 (42.3) | |
| >65 | 150 (39.3) | 172 (44.3) | 322 (41.8) | 0.3303 |
| >75 | 74 (19.4) | 83 (21.4) | 157 (20.4) | |
| Height (cm) | | | | |
| n | 382 | 388 | 770 | |
| Mean (SD) | 168.6 (9.90) | 168.5 (9.84) | 168.6 (9.87) | |
| Median | 169.0 | 168.0 | 169.0 | |
| Min, Max | 137, 196 | 135, 198 | 135, 198 | 0.8528 |
| Weight (kg) | | | | |
| n | 382 | 388 | 770 | |
| Mean (SD) | 77.67 (18.018) | 78.00 (17.861) | 77.83 (17.928) | |
| Median | 76.00 | 77.50 | 77.00 | |
| Min, Max | 36.0, 147.0 | 28.0, 145.2 | 28.0, 147.0 | 0.9687 |

-continued

| Characteristics | Compound 1 (N = 382) | Moxifloxacin (N = 388) | All Subjects (N = 770) | p-value |
|---|---|---|---|---|
| BMI (kg/m$^2$) | | | | |
| n | 382 | 388 | 770 | |
| Mean (SD) | 27.26 (5.763) | 27.42 (5.791) | 27.34 (5.774) | |
| Median | 26.28 | 26.50 | 26.36 | |
| Min, Max | 16.0, 50.6 | 12.6, 54.7 | 12.6, 54.7 | 0.6103 |
| Renal Function (Local Lab), n (%) | | | | |
| n | 382 | 388 | 770 | |
| Normal renal function [CrCl>80 mL/min] | 186 (48.7) | 207 (53.4) | 393 (51.0) | |
| Mild renal impairment [CrCl>50-80 mL/min] | 127 (33.2) | 119 (30.7) | 246 (31.9) | |
| Mod. renal impairment [CrCl 30-50 mL/min] | 69 (18.1) | 62 (16.0) | 131 (17.0) | |
| Severe renal impairment [CrCl <30 mL/min] | 0 | 0 | 0 | 0.4245 |
| PORT Score (actual) | | | | |
| n | 382 | 388 | 770 | |
| Mean (SD) | 83.1 (16.25) | 84.0 (15.99) | 83.5 (16.12) | |
| Median | 80.0 | 82.0 | 81.0 | |
| Min, Max | 48, 130 | 36, 136 | 36, 136 | 0.1571 |
| PORT Risk Class (actual) | | | | |
| n | 382 | 388 | 770 | |
| I (0 ≤ Port Score ≤ 50) | 2 (0.5) | 2 (0.5) | 4 (0.5) | |
| II (51 ≤ Port Score ≤ 70) | 54 (14.1) | 54 (13.9) | 108 (14.0) | |
| III (71 ≤ Port Score ≤ 90) | 226 (59.2) | 216 (55.7) | 442 (57.4) | |
| IV (91 ≤ Port Score ≤ 130) | 100 (26.2) | 115 (29.6) | 215 (27.9) | |
| V (Port Score≥131) | 0 | 1 (0.3) | 1 (0.1) | 0.7341 |

In the table above, Age is calculated from the date of birth to the informed consent date. p-values for differences between treatment groups are from Fisher's exact test (for categorical variables) or Wilcoxon Rank Sum test (for continuous variables). For each categorical parameter, the denominator for the percentage is the number of subjects who had that parameter assessed. PORT Score (actual) and PORT Risk Class (actual) are based on PORT score (derived/corrected) from CRF.

Demographic and Baseline
Characteristics—CE-PTE Population

| Characteristics | Omadacycline (N = 340) | Moxifloxacin (N = 345) | All Subjects (N = 685) | p-value |
|---|---|---|---|---|
| Gender, n (%) | | | | |
| n | 340 | 345 | 685 | |
| Female | 154 (45.3) | 152 (44.1) | 306 (44.7) | |
| Male | 186 (54.7) | 193 (55.9) | 379 (55.3) | 0.7590 |
| Race, n (%) | | | | |
| n | 340 | 345 | 685 | |
| White | 312 (91.8) | 316 (91.6) | 628 (91.7) | |
| Black or African American | 11 (3.2) | 6 (1.7) | 17 (2.5) | |
| Asian | 16 (4.7) | 17 (4.9) | 33 (4.8) | |
| American Indian or Alaska Native | 0 | 2 (0.6) | 2 (0.3) | |
| Native Hawaiian or Other Pacific Islander | 0 | 0 | 0 | |
| Other | 1 (0.3) | 4 (1.2) | 5 (0.7) | 0.3022 |
| Ethnicity, n (%) | | | | |
| n | 340 | 345 | 685 | |
| Hispanic or Latino | 8 (2.4) | 8 (2.3) | 16 (2.3) | |
| Not Hispanic or Latino | 328 (96.5) | 335 (97.1) | 663 (96.8) | |
| Not Reported/Unknown | 4 (1.2) | 2 (0.6) | 6 (0.9) | 0.9061 |

-continued

| Characteristics | Omadacycline (N = 340) | Moxifloxacin (N = 345) | All Subjects (N = 685) | p-value |
|---|---|---|---|---|
| Age (years) | | | | |
| n | 340 | 345 | 685 | |
| Mean (SD) | 61.3 (15.34) | 62.2 (15.12) | 61.8 (15.23) | |
| Median | 61.0 | 63.0 | 63.0 | |
| Min, Max | 19, 97 | 19, 94 | 19, 97 | 0.3188 |
| Categorical Age (years), n (%) | | | | |
| n | 340 | 345 | 685 | |
| 18-45 | 55 (16.2) | 52 (15.1) | 107 (15.6) | |
| >45-65 | 145 (42.6) | 141 (40.9) | 286 (41.8) | |
| >65 | 140 (41.2) | 152 (44.1) | 292 (42.6) | 0.7574 |
| >75 | 70 (20.6) | 75 (21.7) | 145 (21.2) | |
| Height (cm) | | | | |
| n | 340 | 345 | 685 | |
| Mean (SD) | 168.8 (9.84) | 168.5 (9.82) | 168.7 (9.82) | |
| Median | 169.0 | 168.0 | 169.0 | |
| Min, Max | 137, 196 | 135, 198 | 135, 198 | 0.7520 |
| Weight (kg) | | | | |
| n | 340 | 345 | 685 | |
| Mean (SD) | 77.70 (17.203) | 78.20 (18.029) | 77.95 (17.613) | |
| Median | 75.80 | 78.00 | 77.00 | |
| Min, Max | 38.7, 136.0 | 28.0, 145.2 | 28.0, 145.2 | 0.8760 |
| BMI (kg/m$^2$) | | | | |
| n | 340 | 345 | 685 | |
| Mean (SD) | 27.25 (5.623) | 27.48 (5.821) | 27.37 (5.721) | |
| Median | 26.23 | 26.57 | 26.37 | |
| Min, Max | 16.5, 50.6 | 12.6, 54.7 | 12.6, 54.7 | 0.5139 |
| Renal Function (Local Lab), n (%) | | | | |
| n | 340 | 345 | 685 | |
| Normal renal function [CrCl>80 mL/min] | 164 (48.2) | 180 (52.2) | 344 (50.2) | |
| Mild renal impairment [CrCl >50-80 mL/min] | 119 (35.0) | 112 (32.5) | 231 (33.7) | |
| Moderate renal impairment [CrCl 30-50 mL/min] | 57 (16.8) | 53 (15.4) | 110 (16.1) | |
| Severe renal impairment [CrCl <30 mL/min] | 0 | 0 | 0 | 0.5897 |
| PORT Score (actual) | | | | |
| n | 340 | 345 | 685 | |
| Mean (SD) | 83.5 (15.98) | 83.6 (15.19) | 83.6 (15.57) | |
| Median | 80.0 | 82.0 | 81.0 | |
| Min, Max | 51, 130 | 53, 123 | 51, 130 | 0.5004 |
| PORT Risk Class (actual) | | | | |
| n | 340 | 345 | 685 | |
| I (0 ≤ Port Score ≤ 50) | 0 | 0 | 0 | |
| II (51 ≤ Port Score ≤ 70) | 45 (13.2) | 49 (14.2) | 94 (13.7) | |
| III (71 ≤ Port Score ≤ 90) | 204 (60.0) | 202 (58.6) | 406 (59.3) | |
| IV (91 ≤ Port Score ≤ 130) | 91 (26.8) | 94 (27.2) | 185 (27.0) | |
| V (Port Score≥131) | 0 | 0 | 0 | 0.9048 |

In the table above, Age is calculated from the date of birth to the informed consent date. p-values for differences between treatment groups are from Fisher's exact test (for categorical variables) or Wilcoxon Rank Sum test (for continuous variables). For each categorical parameter, the denominator for the percentage is the number of subjects who had that parameter assessed. PORT Score (actual) and PORT Risk Class (actual) are based on PORT score (derived/corrected) from CRF.

c) Efficacy Analysis

For all efficacy analyses, subject data was analyzed in the group to which the subject was randomized.

The following table summarizes the primary analysis results for early clinical response determined 72-120 hours after the first infusion of test article in the ITT population.

| Efficacy Outcome | Compound 1 (N = 386) n (%) | Moxifloxacin (N = 388) n (%) | Difference (95% CI) |
|---|---|---|---|
| Clinical Success | 313 (81.1) | 321 (82.7) | −1.6 (−7.1, 3.8) |
| Clinical Failure or Indeterminate | 73 (18.9) | 67 (17.3) | |
| Clinical Failure | 49 (12.7) | 47 (12.1) | |
| Indeterminate | 24 (6.2) | 20 (5.2) | |

CI=Confidence Interval. Difference was observed difference in Early Clinical Success rate between the Compound 1 and moxifloxacin groups. 95% CI was constructed based on the Miettinen and Nurminen method without stratification. Percentages were based on the number of subjects in each treatment group.

Figure 2:
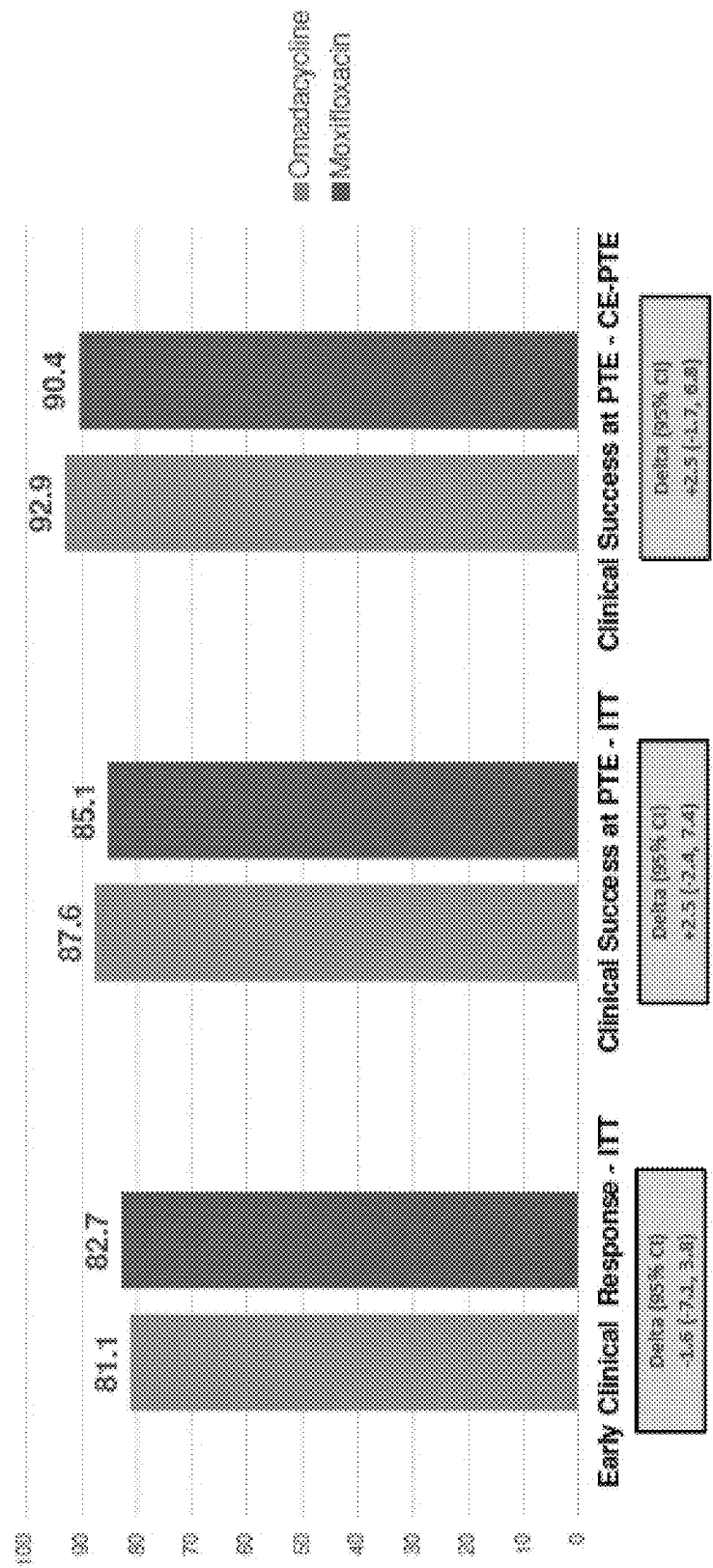
FIG. 2 shows that Compound 1 ("Omadacycline") demonstrated statistical non-inferiority (10% margin) relative to moxifloxacin, for early clinical response (ECR) in the ITT (Intent To Treat) population (see the pair of bars on the left) (FDA Primary Endpoint); and for clinical success at the PTE (Post Treatment/Therapy Evaluation), in both the ITT population (see the middle pair of bars) and the CE-PTE (Clinically Evaluable population at the PTE) population (see the right pair of bars) (FDA Secondary Endpoints).

The early clinical success rates (at 72-120 hr) in the ITT population, for both Compound 1 and Moxifloxacin, are depicted in FIG. 2. See the left most pair of bars. The data shows that the observed −1.6% difference in clinical success rate is well within the 10% margin of statistical non-inferiority between −7.1% and 3.8%, at 95% CI (Confidence Interval), and thus the primary efficacy point (for FDA approval) is met.

For Early Clinical Response Efficacy Variable (Clinical Success, Clinical Failure or Indeterminate), an Indeterminate Response was included in the denominator for the calculation of the percentage of subjects with a Clinical Success in the ITT population and thus, was essentially considered as a Clinical Failure for the purpose of the primary analysis.

The following table summarizes the overall clinical response at PTE visit based on investigator assessment of the ITT and CE-PTE populations.

| Population | Efficacy Outcome | Compound 1 n (%) | Moxi-floxacin n (%) | Difference (95% CI)[1] |
|---|---|---|---|---|
| ITT | | (N = 386) | (N = 388) | |
| | Clinical Success | 338 (87.6) | 330 (85.1) | 2.5 (−2.4, 7.4) |
| | Clinical Failure or Indeterminate | 48 (12.4) | 58 (14.9) | |
| | Clinical Failure | 32 (8.3) | 42 (10.8) | |
| | Indeterminate | 16 (4.1) | 16 (4.1) | |
| CE-PTE | | (N = 340) | (N = 345) | |
| | Clinical Success | 316 (92.9) | 312 (90.4) | 2.5 (−1.7, 6.8) |
| | Clinical Failure | 24 (7.1) | 33 (9.6) | |

[1]95% CI was constructed based on the Miettinen and Nurminen method without stratification.

CI=Confidence Interval; Difference was observed difference in Overall Clinical Success rate at PTE between the Compound 1 and Moxifloxacin groups. Overall Clinical Response at PTE was based on the Investigator Assessment at the EOT and PTE visits. Percentages were based on the number of subjects in each treatment group. EOT=End of Treatment; PTE=Post Treatment Evaluation.

The overall clinical response rates at PTE visit based on investigator assessment of the ITT population and the CE-PTE population, for both Compound 1 and Moxifloxacin, are also depicted in FIG. 2. See the middle (ITT) and the right most (CE-PTE) pairs of bars. The data shows that the observed 2.5% difference in overall clinical response rate in the ITT population is within the 10% margin of statistical non-inferiority between −2.4% and 7.4%, at 95% CI (Confidence Interval); and that the observed 2.5% difference in overall clinical response rate in the CE-PTE population is within the 10% margin of statistical non-inferiority between −1.7% and 6.8%, at 95% CI (Confidence Interval). Thus the secondary efficacy point (for FDA approval) is also met.

For Investigator's Assessment of Clinical Response at PTE Efficacy Variable (Clinical Success, Clinical Failure or Indeterminate in the ITT population and Clinical Success and Clinical Failure in the CE population), an Indeterminate Response was included in the denominator for the calculation of the percentage of subjects with a Clinical Success in the ITT population and thus, was essentially considered a Clinical Failure for the purpose of the primary analysis for the EMA.

To demonstrate the efficacy of Compound 1 was non-inferior to moxifloxacin in the treatment of adults with CABP, the following hypothesis were evaluated by analysis of the Clinical Success rates.

The null hypothesis and alternate hypothesis for the Early Clinical Response endpoint was assessed in the ITT population as follows:

$$H_o: \theta_T - \theta_C \leq -\Delta$$

$$H_{ai}: \theta_T - \theta_C > -\Delta$$

Where the clinical success rate for the Compound 1 regimen was $\theta_T$ and for moxifloxacin is $\theta_C$. Δ was the non-inferiority (NI) margin and was 0.10 (or 10%).

Similar null and alternative hypotheses can be set up with Δ of 0.10 for the PTE endpoint. For the Early Clinical Response (FDA) endpoint, a 2-sided 95% confidence interval (CI) approach for the difference of clinical success rates (using the point estimate of the difference: Compound 1 response proportion minus moxifloxacin response proportion) was used to test for the NI of the Compound 1 arm compared to the moxifloxacin arm in the ITT population. The 95% CI was calculated using the unstratified method proposed by Miettinen and Nurminen (*Statistics in Medicine* 4:213-226, 1985). Compound 1 is considered non-inferior to moxifloxacin if the lower bound of the CI is greater than −0.10 (or −10%). This concept is expressed herein as "within 10% margin of non-inferiority."

For Investigator's Assessment of Clinical Response at PTE (EMA) primary efficacy analyses in both the ITT and CE populations, a 2-sided 97.5% CI approach for the difference of clinical success rates (using the point estimate of the difference: Compound 1 response proportion minus moxifloxacin response proportion) was used to test for the NI of the Compound 1 arm compared to the moxifloxacin arm in those subjects with a PORT Risk Class of III or higher. The 97.5% CI was calculated using the stratified (for the randomization stratification factors) method proposed by Miettinen and Nurminen. Compound 1 is considered non-inferior to moxifloxacin if the lower bound of the CI is greater than −0.10 (or −10%).

Early Clinical Response and Investigator's Assessment of Clinical Response at PTE was tested separately and were not co-primary endpoints. The probability for approving an ineffective drug based on PTE efficacy was 1.25%, regardless of the result for the Early Clinical Response endpoint and vice versa. An adjustment would only be required if winning on at least 1 endpoint would result in global approval which was not the case here. In addition, no alpha adjustment was needed for the co-primary efficacy endpoints for the EMA (ITT and CE populations) since NI must be shown in both populations to conclude NI. Hence there was no adjustment for multiple endpoints.

Additional and sensitivity analyses of the primary efficacy outcomes (Early Clinical Response and Investigator's Assessment of Clinical Response at PTE) were performed. If the null hypothesis of inferiority is rejected for the Early Clinical Response in the ITT population and the observed success response proportion for Compound 1 is larger than the observed proportion for moxifloxacin, a formal statistical analysis of superiority would be conducted. If the lower limit of the 2-sided CI for the treatment difference is greater than 0%, Compound 1 will be considered superior to moxifloxacin.

The primary efficacy outcome was also assessed separately across the stratification factors of PORT Risk Class, receipt of allowed antibacterial therapy in the 72 hours prior to study treatment and geographic region stratum by treatment group. For each PORT Risk Class stratum, each prior antibacterial therapy stratum and each geographic region stratum, a 2-sided 95% CI for the observed difference in Early Clinical Response rates were calculated for the ITT population. Additional subgroup analyses of the primary efficacy outcome might have been conducted as descriptive analyses.

The following two tables summarize the overall clinical response at PTE visit based on investigator assessment by PORT Risk Class in the ITT population and the CE-PTE population, respectively.

Overall Clinical Response at PTE Visit Based on Investigator Assessment by PORT Risk Class in the ITT Population

| PORT Risk Class Efficacy Outcome | PORT Risk Class as Randomized | | | Actual PORT Risk Class[1] | | |
|---|---|---|---|---|---|---|
| | Compound 1 (N = 386) n (%) | Moxifloxacin (N = 388) n (%) | Difference (CI) | Compound 1 (N = 386) n (%) | Moxifloxacin (N = 388) n (%) | Difference (CI) |
| PORT Risk Class II[2] | 56 | 56 | | 57 | 56 | |
| Clinical Success | 45 (80.4) | 47 (83.9) | −3.6 (−18.2, 11.0)[4] | 47 (82.5) | 47 (83.9) | −1.5 (−15.7, 12.8)[4] |
| Clinical Failure or Indeterminate | 11 (19.6) | 9 (16.1) | | 10 (17.5) | 9 (16.1) | |
| Clinical Failure | 6 (10.7) | 7 (12.5) | | 5 (8.8) | 7 (12.5) | |
| Indeterminate | 5 (8.9) | 2 (3.6) | | 5 (8.8) | 2 (3.6) | |
| PORT Risk Class III\IV | 330 | 332 | | 329 | 331 | |
| Clinical Success | 293 (88.8) | 283 (85.2) | 3.5 (−1.6, 8.7)[4] | 291 (88.4) | 282 (85.2) | 3.3 (−1.9, 8.5)[4] (−2.7, 9.3)[5] |
| Clinical Failure or Indeterminate | 37 (11.2) | 49 (14.8) | | 38 (11.6) | 49 (14.8) | |
| Clinical Failure | 26 (7.9) | 35 (10.5) | | 27 (8.2) | 35 (10.6) | |
| Indeterminate | 11 (3.3) | 14 (4.2) | | 11 (3.3) | 14 (4.2) | |
| PORT Risk Class III | 241 | 232 | | 227 | 216 | |
| Clinical Success | 217 (90.0) | 201 (86.6) | 3.4 (−2.4, 9.4)[4] | 206 (90.7) | 190 (88.0) | 2.8 (−3.0, 8.7)[4] |
| Clinical Failure or Indeterminate | 24 (10.0) | 31 (13.4) | | 21 (9.3) | 26 (12.0) | |
| Clinical Failure | 17 (7.1) | 21 (9.1) | | 16 (7.0) | 18 (8.3) | |
| Indeterminate | 7 (2.9) | 10 (4.3) | | 5 (2.2) | 8 (3.7) | |
| PORT Risk ClassIV[3] | 89 | 100 | | 102 | 116 | |
| Clinical Success | 76 (85.4) | 82 (82.0) | 3.4 (−7.5, 14.0)[4] | 85 (83.3) | 93 (80.2) | 3.2 (−7.4, 13.4)[4] |
| Clinical Failure or Indeterminate | 13 (14.6) | 18 (18.0) | | 17 (16.7) | 23 (19.8) | |
| Clinical Failure | 9 (10.1) | 14 (14.0) | | 11 (10.8) | 17 (14.7) | |
| Indeterminate | 4 (4.5) | 4 (4.0) | | 6 (5.9) | 6 (5.2) | |

Figure 3:
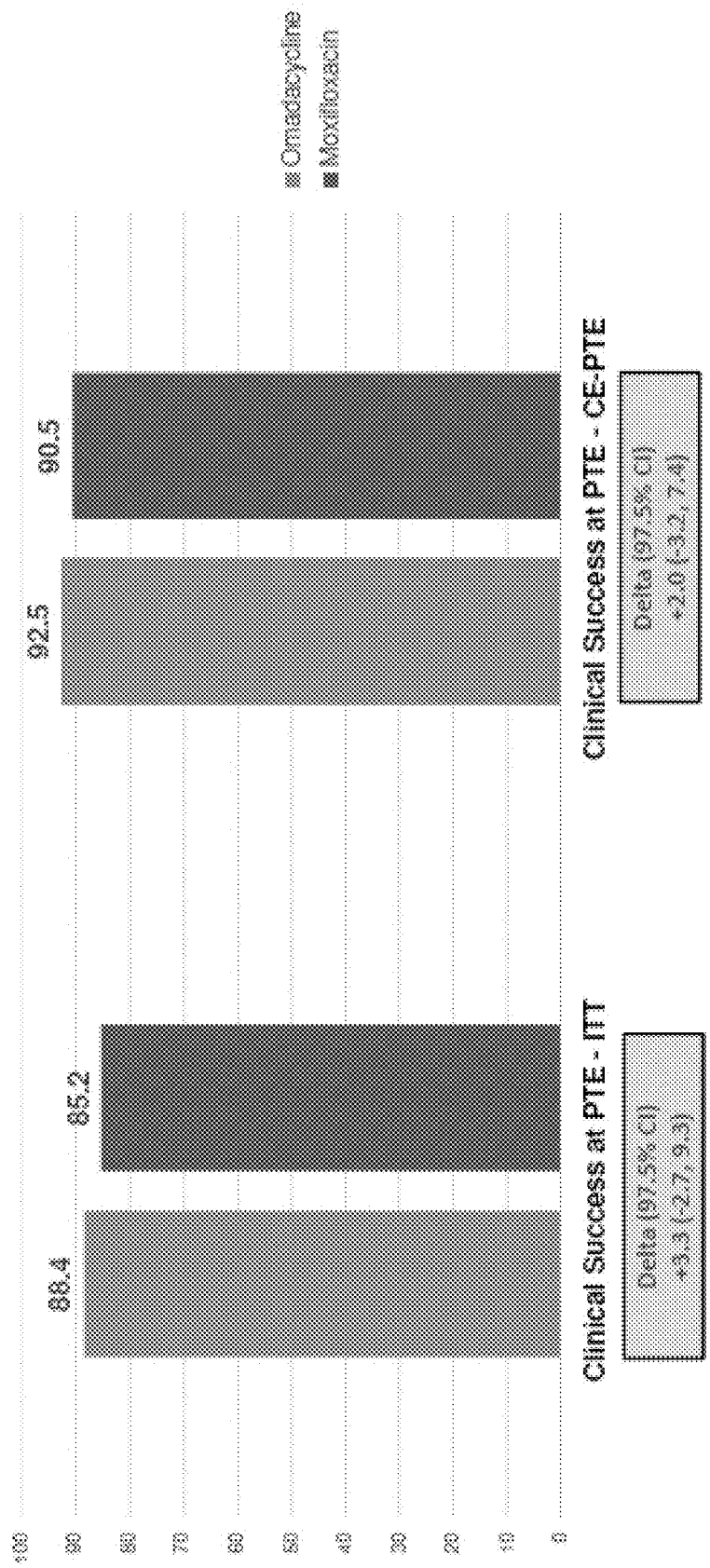
FIG. 3 shows that Compound 1 ("Omadacycline") demonstrated statistical non-inferiority (10% margin) relative to moxifloxacin, based on clinical success at the PTE in both the ITT population limited to patients with CABP categorized as PORT Risk Class III/IV (see the left pair of bars) and the CE-PTE population limited to patients with CABP categorized as PORT Risk Class III/IV (see the right pair of bars) (EMA co-Primary Endpoints).

The overall clinical response rates at PTE visit based on investigator assessment of the ITT population limited to actual PORT Risk Class III/IV subjects, for both Compound 1 and Moxifloxacin, are depicted in FIG. 3. See the left pairs of bars. The data shows that the observed 3.3% difference in overall clinical response rate is within the 10% margin of statistical non-inferiority between −2.7% and 9.3%, at 97.5% CI (Confidence Interval). Thus one of the co-primary efficacy point (for EMA approval) is met.

Overall Clinical Response at PTE Visit Based on Investigator Assessment by PORT Risk Class in the CE-PTE Population

| PORT Risk Class Efficacy Outcome | PORT Risk Class as Randomized | | | Actual PORT Risk Class[1] | | |
|---|---|---|---|---|---|---|
| | Compound 1 (N = 340) n (%) | Moxifloxacin (N = 345) n (%) | Difference (CI) | Compound 1 (N = 340) n (%) | Moxifloxacin (N = 345) n (%) | Difference (CI) |
| PORT Risk Class II | 44 | 48 | | 45 | 49 | |
| Clinical Success | 41 (93.2) | 44 (91.7) | 1.5 (−11.2, 13.9)[4] | 43 (95.6) | 44 (89.8) | 5.8 (−6.1, 18.1)[4] |
| Clinical Failure | 3 (6.8) | 4 (8.3) | | 2 (4.4) | 5 (10.2) | |
| PORT Risk Class III\IV | 296 | 297 | | 295 | 296 | |

-continued

| | PORT Risk Class as Randomized | | | Actual PORT Risk Class[1] | | |
|---|---|---|---|---|---|---|
| PORT Risk Class<br>Efficacy Outcome | Compound 1<br>(N = 340)<br>n (%) | Moxifloxacin<br>(N = 345)<br>n (%) | Difference<br>(CI) | Compound 1<br>(N = 340)<br>n (%) | Moxifloxacin<br>(N = 345)<br>n (%) | Difference<br>(CI) |
| Clinical Success | 275 (92.9) | 268 (90.2) | 2.7 (−1.9, 7.3)[4] | 273 (92.5) | 268 (90.5) | 2.0 (−2.6, 6.6)[4]<br>(−3.2, 7.4)[5] |
| Clinical Failure | 21 (7.1) | 29 (9.8) | | 22 (7.5) | 28 (9.5) | |
| PORT Risk Class III | 216 | 212 | | 204 | 202 | |
| Clinical Success | 202 (93.5) | 193 (91.0) | 2.5 (−2.7, 7.8)[4] | 191 (93.6) | 186 (92.1) | 1.5 (−3.6, 6.9)[4] |
| Clinical Failure | 14 (6.5) | 19 (9.0) | | 13 (6.4) | 16 (7.9) | |
| PORT Risk Class IV | 80 | 85 | | 91 | 94 | |
| Clinical Success | 73 (91.3) | 75 (88.2) | 3.0 (−6.8, 12.8)[4] | 82 (90.1) | 82 (87.2) | 2.9 (−6.7, 12.5)[4] |
| Clinical Failure | 7 (8.8) | 10 (11.8) | | 9 (9.9) | 12 (12.8) | |

[1]Actual PORT Risk Class was based on PORT score (derived/corrected) from CRF.
[2]Also includes 4 subjects with an actual PORT Risk Class of I.
[3]Also includes 1 subject with an actual PORT Risk Class of V.
[4]Unstratified 95% CI was constructed based on the Miettinen and Nurminen method without stratification.
[5]Stratified 97.5% CI was adjusted for prior antibiotics use (yes and no) constructed based on the Miettinen and Nurminen method with stratification, using Cochran-Mantel-Haenszel weights as stratum weights.
CI = Confidence Interval;
PTE = Post Treatment Evaluation.
Difference was observed difference in Overall Clinical Success rate at PTE between the Compound 1 and Moxifloxacin groups. Percentages were based on the number of subjects in each treatment group within each PORT Risk Class.

The overall clinical response rates at PTE visit based on investigator assessment of the CE-PTE population, limited to patients with PORT III/IV CABP, for both Compound 1 and Moxifloxacin, are also depicted in FIG. 3. See the right pairs of bars. The data shows that the observed 2.0% difference in overall clinical response rate is within the 10% margin of non-inferiority between −3.2% and 7.4%, at 97.5% CI (Confidence Interval). Thus another of the co-primary efficacy point (for EMA approval) is also met.

Sensitivity analyses include: conducting an adjusted analysis of the primary efficacy outcome based on the randomized stratum and separately, based on the stratum the subject actually belongs, and conducting an analysis where all subjects with an Indeterminate response are considered Clinical Successes.

d) Analysis of Secondary Variables

The number and percentage of subjects classified as a Clinical Success, Clinical Failure and Indeterminate by the Investigator's Assessment at PTE in the ITT and CE populations (by definition subjects with an Indeterminate response were excluded from the CE population) were calculated for each treatment group. A 2-sided unadjusted 95% CI was constructed for the observed difference in the clinical success rate using the method of Miettinen and Nurminen. For Investigator's Assessment of Clinical Response at PTE in the ITT and CE populations the 95% CI was for descriptive purposes only and no conclusion of NI was made. The number and percentage of subjects in each treatment group in each response category for Early Clinical Response was presented for the microITT population. The number and percentage of subjects who were classified as a Clinical Success and Clinical Failure by the investigator at the PTE visit in ME population were calculated. Two-sided unadjusted 95% CI was constructed for the observed difference in the clinical success rates using the method of Miettinen and Nurminen.

The number and percentage of subjects with an Early Clinical Response of success and an Investigator's Assessment of Clinical Response at PTE of Clinical Success by pathogen was provided in the microITT and ME populations. All-cause mortality (ACM) at 15 and 30 days after the first dose of test article was summarized in the ITT population. Subjects who were lost to follow-up were considered deceased for this analysis. A 2-sided unadjusted 95% CI for the observed difference in mortality rates was calculated for ACM.

e) Analysis of Additional Efficacy Variables

Additional efficacy analyses were conducted to support the efficacy findings of the primary and secondary outcomes. CIs were determined for descriptive purposes, but no conclusions of NI were made. The number and percentage of subjects classified as a Clinical Success, Clinical Failure and Indeterminate by the Investigator's Assessment at EOT in the ITT and CE populations (by definition subjects with an Indeterminate response were excluded from the CE population) were calculated. A 2-sided unadjusted 95% CI was constructed for the observed difference in the Clinical Success rate using the method of Miettinen and Nurminen. The number and percentage of subjects with stabilization of vital signs and clinical signs/laboratory findings associated with CABP at 72-120 hours post first dose of test article were presented by treatment group in the ITT population. These include body temperature (no fever or hypothermia), SBP (>90 mm Hg), heart rate (<90 bpm), RR (<20 breaths/minute), $PaO_2$ (≥60 mm Hg by ABG or oxygen saturation ≥90% by pulse oximetry), physical exam findings (no findings of pulmonary consolidation), WBC count (<12,000 cells/mm$^3$ or ≥4,000 cells/mm) or immature neutrophils (<15%). A summary (number and percentage of subjects) of the assessment of clinical signs and symptoms of CABP at each time point throughout the study were presented by treatment group in the ITT population. The number and percentage of subjects with resolution of signs and symptoms present at Screening (back to pre-CABP status) were also provided by study visit. The number and percentage of subjects with no worsening of clinical symptoms of CABP and with the absence of new symptoms of CABP were provided by treatment group in the ITT population.

The per-subject and per-pathogen microbiologic outcomes were provided for the microITT and ME populations at the EOT and PTE visits. For example, the table below summarizes the overall clinical success at PTE visit in the microITT population, based on investigator assessment by baseline pathogen from blood specimens, respiratory specimens, urinary antigen tests, and/or serology.

|  | Compound 1 (N = 204) | | Moxifloxacin (N = 182) | |
| --- | --- | --- | --- | --- |
| Baseline Pathogen | N1 | Clinical Success n (%) | N1 | Clinical Success n (%) |
| Gram-Positive Bacteria (aerobes) | 61 | 52 (85.2) | 56 | 49 (87.5) |
| *Streptococcus pneumoniae*[1] | 43 | 37 (86.0) | 34 | 31 (91.2) |
| MDRSP | 7 | 7 (100.0) | 6 | 6 (100.0) |
| PSSP | 26 | 23 (88.5) | 22 | 21 (95.5) |
| Macrolide Resistant | 10 | 10 (100.0) | 5 | 5 (100.0) |
| *Staphylococcus aureus* | 11 | 8 (72.7) | 11 | 9 (81.8) |
| MRSA | 0 | 0 | 1 | 1 (100.0) |
| MSSA | 11 | 8 (72.7) | 10 | 8 (80.0) |
| Beta Hemolytic *Streptococcus* | 2 | 2 (100.0) | 3 | 1 (33.3) |
| *Streptococcus agalactiae* | 2 | 2 (100.0) | 3 | 1 (33.3) |
| *Streptococcus anginosus* | 0 | 0 | 1 | 0 |
| *Streptococcus constellatus* | 1 | 1 (100.0) | 1 | 1 (100.0) |
| *Streptococcus gordonii* | 0 | 0 | 1 | 1 (100.0) |
| *Streptococcus mitis* | 3 | 3 (100.0) | 5 | 3 (60.0) |
| *Streptococcus mitis* group | 1 | 1 (100.0) | 2 | 2 (100.0) |
| *Streptococcus oralis* | 1 | 1 (100.0) | 0 | 0 |
| *Streptococcus parasanguinis* | 0 | 0 | 2 | 1 (50.0) |
| *Streptococcus salivarius* | 1 | 1 (100.0) | 3 | 3 (100.0) |
| *Streptococcus sanguinis* | 0 | 0 | 2 | 1 (50.0) |
| *Streptococcus sanguis* ii | 2 | 2 (100.0) | 0 | 0 |
| Gram-Negative Bacteria (aerobes) | 79 | 67 (84.8) | 68 | 55 (80.9) |
| *Acinetobacter baumanii* | 0 | 0 | 1 | 1 (100.0) |
| *Acinetobacter baumanii* complex | 0 | 0 | 1 | 0 |
| *Acinetobacter junii* | 1 | 1 (100.0) | 0 | 0 |
| *Acinetobacter lwoffii* | 1 | 1 (100.0) | 0 | 0 |
| *Citrobacter braakii* | 0 | 0 | 1 | 1 (100.0) |
| *Citrobacter freundii* | 0 | 0 | 1 | 1 (100.0) |
| *Enterobacter cloacae* | 2 | 2 (100.0) | 4 | 3 (75.0) |
| *Escherichia coli* | 6 | 4 (66.7) | 7 | 4 (57.1) |
| *Haemophilus haemolyticus* | 1 | 1 (100.0) | 0 | 0 |
| *Haemophilus influenzae* | 32 | 26 (81.3) | 16 | 16 (100.0) |
| *Haemophilus parahaemolyticus* | 2 | 2 (100.0) | 2 | 1 (50.0) |
| *Haemophilus parainfluenzae* | 18 | 15 (83.3) | 17 | 13 (76.5) |
| *Klebsiella oxytoca* | 1 | 0 | 4 | 4 (100.0) |
| *Klebsiella pneumoniae* | 13 | 10 (76.9) | 13 | 11 (84.6) |
| *Moraxella catarrhalis* | 4 | 4 (100.0) | 1 | 1 (100.0) |
| *Morganella morganii* | 1 | 1 (100.0) | 0 | 0 |
| *Neisseria meningitidis* | 1 | 1 (100.0) | 1 | 1 (100.0) |
| *Proteus mirabilis* | 2 | 1 (50.0) | 2 | 2 (100.0) |
| *Pseudomonas aeruginosa* | 3 | 2 (66.7) | 5 | 5 (100.0) |
| *Pseudomonas putida* | 0 | 0 | 1 | 1 (100.0) |
| *Serratia marcescens* | 1 | 1 (100.0) | 0 | 0 |
| *Stenotrophomonas maltophilia* | 0 | 0 | 2 | 1 (50.0) |
| Atypical Pathogens | 118 | 109 (92.4) | 106 | 97 (91.5) |
| *Mycoplasma pneumoniae* | 70 | 66 (94.3) | 57 | 50 (87.7) |
| *Chlamydophila pneumoniae* | 28 | 25 (89.3) | 28 | 25 (89.3) |
| *Legionella pneumophila*[2] | 37 | 35 (94.6) | 37 | 36 (97.3) |
| Gram-negative organisms (anaerobes) | 0 | 0 | 1 | 0 |
| *Prevotella oris* | 0 | 0 | 1 | 0 |

[1]Overall tabulation of *Streptococcus pneumoniae* includes identification from urinary antigen only which will not have susceptibility data.
[2]*Legionella pneumophila* may be detected from culture, serology and/or urinary antigen test. Subjects with the same pathogen isolated from multiple specimens are counted only once for that pathogen. Subjects with the same pathogen from a blood specimen, respiratory specimen, urinary antigen test, and/or serology are counted only once for that pathogen.
Subjects are counted only once in the overall tabulations if they have more than one respective pathogen at baseline.
PTE = Post Treatment Evaluation.
N = Number of subjects in the microITT population.
N1 = Number of subjects with the specific baseline pathogen.
n = Number of subjects in the specific category. Percentages are based on the number of subjects with the specific baseline pathogen.

For selected pathogens that have 10 or more isolates in the Compound 1 treatment arm, data was extracted and shown in FIG. 4.

Two-sided unadjusted 95% CIs were provided for the difference in per-subject microbiological favorable outcome rates. A concordance analysis of Early Clinical Response and Investigator's Assessment of Clinical Response at PTE in the ITT analysis set were also presented.

f) Safety Outcome Measures

Safety variables included the incidence rate of AEs, change in vital signs, ECG parameters and laboratory test results obtained during the course of the study.

Summary tables were provided for all treatment-emergent adverse events (TEAEs), defined as an AE with a start date and time on or after the first dose of test article. AEs were summarized by presenting the number and percentage of subjects having each TEAE for each treatment group by system organ class (SOC) and preferred term (PT). Additional tabulations provided summaries by SOC and PT of subjects experiencing SAEs, severe TEAEs, TEAEs judged to be related to test article, TEAEs leading to discontinuation of test article, TEAEs leading to dose interruption of test article, and TEAEs of special interest.

The following table provides an overview of Adverse Events (AEs) within the safety population.

codes to the same MedDRA category, the subject is counted only once. PTs are sorted by decreasing frequency within the Compound 1 column.

Thus, it is apparent that gastrointestinal (GI) adverse events (AEs, including vomiting, nausea, diarrhea, and dyspepsia) associated with treatment with Compound 1 are mild.

| Parameter | Compound 1 (N = 382) n (%) | Moxifloxacin (N = 388) n (%) | All Subjects (N = 770) n (%) |
|---|---|---|---|
| Total Number of AEs | 434 | 520 | 954 |
| Total Number of TEAEs | 376 | 461 | 837 |
| Subjects with at Least One, n (%) | | | |
| Adverse Events (AE) | 170 (44.5) | 200 (51.5) | 370 (48.1) |
| TEAE | 157 (41.1) | 188 (48.5) | 345 (44.8) |
| Drug-Related TEAE | 39 (10.2) | 69 (17.8) | 108 (14.0) |
| Severe TEAE | 25 (6.5) | 26 (6.7) | 51 (6.6) |
| Serious TEAE | 23 (6.0) | 26 (6.7) | 49 (6.4) |
| Drug-Related Serious TEAE | 2 (0.5) | 2 (0.5) | 4 (0.5) |
| Serious TEAE Leading to Death* | 8 (2.1) | 4 (1.0) | 12 (1.6) |
| TEAE Leading to Premature Discontinuation of Test Article | 21 (5.5) | 27 (7.0) | 48 (6.2) |
| TEAE Leading to Premature Discontinuation of Study | 7 (1.8) | 9 (2.3) | 16 (2.1) |
| TEAE Leading to Dose Interruption | 0 | 0 | 0 |
| Serious TEAEs Leading to Premature Discontinuation of Test Article | 10 (2.6) | 11 (2.8) | 21 (2.7) |
| Subjects who died, n (%) | 8 (2.1) | 4 (1.0) | 12 (1.6) |

*All deaths occurred in patients >65 years of age; frequency consistent with recently completed CABP studies.
Percentages are based on the Safety population.
A TEAE is defined as an AE occurring after first dose of active test article.
AE = Adverse Events;
TEAE = Treatment-Emergent Adverse Event.

The following table provides a summary of selected TEAEs by Preferred Term within the safety population. With few exceptions, the selected TEAEs have a rate of occurrence of at least about 2% in the Compound 1 treatment group.

| Preferred Term | Omadacycline (N = 382) n (%) | Moxifloxacin (N = 388) n (%) | All Subjects (N = 770) n (%) |
|---|---|---|---|
| Subjects with at Least One TEAE | 157 (41.1) | 188 (48.5) | 345 (44.8) |
| Alanine Aminotransferase Increased | 14 (3.7) | 18 (4.6) | 32 (4.2) |
| Hypertension | 13 (3.4) | 11 (2.8) | 24 (3.1) |
| Gamma-Glutamyltransferase Increased | 10 (2.6) | 8 (2.1) | 18 (2.3) |
| Insomnia | 10 (2.6) | 8 (2.1) | 18 (2.3) |
| Vomiting | 10 (2.6) | 6 (1.5) | 16 (2.1) |
| Constipation | 9 (2.4) | 6 (1.5) | 15 (1.9) |
| Nausea | 9 (2.4) | 21 (5.4) | 30 (3.9) |
| Aspartate Aminotransferase Increased | 8 (2.1) | 14 (3.6) | 22 (2.9) |
| Headache | 8 (2.1) | 5 (1.3) | 13 (1.7) |
| ... | | | |
| Diarrhoea | 4 (1.0) | 31 (8.0) | 35 (4.5) |
| Dyspepsia | 4 (1.0) | 2 (0.5) | 6 (0.8) |
| Clostridium Difficile Colitis | 0 | 1 (0.3) | 1 (0.1) |
| Clostridium Difficile Infection | 0 | 6 (1.5) | 6 (0.8) |
| Pseudomembranous Colitis | 0 | 1 (0.3) | 1 (0.1) |

Coding of Preferred Term is based on MedDRA Version 17.1. Percentages are based on the Safety population. A TEAE is defined as an AE occurring after the first dose of active test article. If a subject has more than one TEAE that The following table summarizes selected TEAEs that led to discontinuation of treatment.

| System Organ Class (SOC) Preferred Term (PT) | Compound 1 (N = 382) n (%) | Moxifloxacin (N = 388) n (%) | All Subjects (N = 770) n (%) |
|---|---|---|---|
| Subjects with at Least One TEAE Leading to Study Drug Discontinuation | 21 (5.5) | 27 (7.0) | 48 (6.2) |
| Gastrointestinal Disorders | 2 (0.5) | 2 (0.5) | 4 (0.5) |
| Vomiting | 2 (0.5) | 0 | 2 (0.3) |
| Nausea | 1 (0.3) | 0 | 1 (0.1) |
| Diarrhoea | 0 | 1 (0.3) | 1 (0.1) |
| Dyspepsia | 0 | 1 (0.3) | 1 (0.1) |

Coding of System Organ Class (SOC) and Preferred Term (PT) was based on MedDRA Version 17.1. Percentages were based on the Safety population. A TEAE was defined as an AE occurring after the first dose of active test article. If a subject had more than one TEAE that coded to the same MedDRA category, the subject was counted only once. SOC terms were sorted alphabetically, then PTs were sorted within each SOC term by decreasing frequency within the Compound 1 column.

The following variables were analyzed descriptively as vital signs:

Vital signs (systolic and diastolic BP, pulse rate, body temperature, RR) including change from Screening by visit Clinically notable vital signs (meeting predefined criteria as specified in the SAP) by visit Electrocardiogram data (RR interval, PR interval, QRS interval, Corrected QT interval [QTc], QTc Bazzett's Correction Formula [QTcB], and QTc Fridericia's Correction Formula [QTcF]) was summarized descriptively at each scheduled evaluation and for the overall worst post-Screening value. Changes from Screening at each visit were also provided. An outlier analysis was conducted based on the worst post-Screening value.

The following variables were analyzed descriptively for laboratory tests:
Laboratory variables by visit
Change from Screening of laboratory variable by visit
Clinically notable laboratory values (meeting predefined criteria specified in SAP) by visit g) PK Population PK analysis was conducted to characterize PK parameters. A population PK data set including subjects with 1 or more quantified Compound 1 concentration determinations was constructed from the dates and times of the doses and blood samples along with all the bioanalytical determinations and subject background information. If the actual date or time for a blood sample or dose was missing, the related bioanalytical determination of the PK concentration was excluded from all analyses. Compound 1 concentrations below the limit of quantification were treated as missing data in summary statistics and for the calculation of PK parameters.

Variables including age (years), body weight (kg), gender, and race/ethnicity along with other covariates previously determined to be important were incorporated into the population PK database. Based on the subjects in the population analysis data set, descriptive summaries at Screening for these variables were reported. Outliers may be excluded from the analysis. These were determined by a scatter plot of the observed concentration versus time post dose and reported. The distribution of the number of samples contributed per subject to the model-based analysis was tabulated. Also, simple summary descriptive statistics for the concentration of samples by study day or week was computed.

Regarding population PK modeling, results from Phase 1 studies indicated that Compound 1 PK was linear and that following iv infusion, plasma concentration-time profiles show a 3-compartmental disposition. Therefore, the probable structural PK model would be a 3-compartment model with zero order input for iv infusion and first order input for po administration. This PK model contained the parameters clearance, volume of distribution, bioavailability and absorption rate constant. The associated population models were nonlinear mixed-effects models. The population model added random effects and covariates for the PK parameters in order to recognize differences among individuals and similarities across observations corresponding to the same subject. At the time of the population modeling, previously reported structural PK models were considered first. A residual error model combining additive error and proportional error was also considered. Simplifications (e.g., fewer random effects, or an alternative residual error model) may be appropriate if the diagnostics for the model suggest false convergence. Additional covariates were investigated graphically (gender, race/ethnicity, age) as part of the model diagnostics and some may be retained in the final model and additional ones in a competing model to deliver estimates of arguably insignificant effects. Scatter plots of the observed concentrations versus population-estimated and individually estimated concentrations were used as part of the overall assessment of the quality of the fit. During modeling, the broad principles outlined by the FDA were followed. The individual model-based exposure measures at steady state (area under the Concentration/Time curve [$AUC_{0-24,ss}$], time to maximum plasma concentration [$T_{max,ss}$], maximum plasma concentration [$C_{max,ss}$]) were computed and summarized.

The relationship between Compound 1 exposure and response (efficacy and safety) was examined as appropriate for the data. A population PK model was used to calculate individual subject AUCs and, subsequently, possible AUC/MIC breakpoints.

Example 4 A Phase I, Randomized, Double-Blind, 3-Period, Crossover Study to Evaluate Safety, Tolerability, and Pharmacokinetics of Multiple Oral Doses of Omadacycline or Placebo in Healthy Adult Subjects The primary objective of this study was to assess and compare the pharmacokinetics (PK) of 300-, 450-, and 600-mg doses of oral omadacycline administered daily over 5 days. The secondary objective of the study was to evaluate the safety and tolerability of multiple doses of omadacycline in healthy adult subjects.

For the treatment of CABP, the then anticipated therapeutic daily oral dose (excluding any loading dose) was 300 mg. For potential future studies, or for administration of a loading dose using the oral formulation, it is possible that a daily dose higher than 300 mg could be used to achieve omadacycline concentrations sufficient to treat target bacteria in the organs/tissues of interest. One early clinical study evaluated single oral doses of omadacycline up to 600 mg, but no studies have evaluated multiple daily doses higher than 300 mg. This study was designed to obtain data on the safety, tolerability, and pharmacokinetics (dose linearity and proportionality) of multiple oral doses of omadacycline at daily doses higher than 300 mg. Placebo groups were included as a reference to minimize potential bias in assessing tolerability.

Multiple daily oral doses of 300, 450, and 600 mg omadacycline or placebo were chosen to be administered in this study. The lowest dose of 300 mg had been evaluated in multiple dose studies and had been well tolerated; this daily dose has also been studied in Phase 3 studies in ABSSSI. Single oral doses up to 600 mg were administered in capsules to healthy adult subjects in 1 early clinical study and were determined to have an acceptable safety profile. There was some increased incidence of GI AEs at oral doses of 400 mg or greater, though events were typically mild (none were severe), and it is possible that some of these events may have been related to the oral formulation. Multiple daily doses of up to 600 mg using the final optimized tablet formulation of omadacycline were expected to have acceptable safety profiles, but this was important to assess in a small carefully controlled Phase 1 study before evaluating these doses in larger clinical studies.

Thus the study was designed as a Phase 1, randomized, double-blind, 3-period, crossover study in healthy adult subjects. The study consisted of a screening period (Day −21 through Day −2), 3 baseline periods (Day −1 of each period), 3 treatment periods (Day 1 through Day 6 of each period), and a study completion visit (within 6 to 10 days after the last dose of study drug in Period 3). There was a washout of at least 5 days between the last dose in one period and the first dose in the next period. Subjects were confined to the study site from Day −1 of Period 1 until discharge on Day 6 of Period 3, after the 24-hour blood sampling, urine sampling, and safety assessments were completed. Subjects returned to the study center 6 to 10 days after the last dose of study drug in Period 3 for the study completion visit.

Subject Selection

Healthy, non-smoking, male and female subjects were eligible for participation in the study if they were between 18 and 55 years of age (inclusive), weighed ≥50 kg, had a body mass index between 18 and 30 kg/m2 (inclusive), met all eligibility criteria during screening (performed within 21 days before dosing in Period 1) and at baseline (Day −1) for Period 1, and provided written informed consent. Health status was determined by past medical history, clinical laboratory tests, vital signs (oral body temperature, systolic blood pressure, diastolic blood pressure, and heart rate), 12-lead electrocardiogram (ECG), and physical examination at screening. Eligibility criteria included ability to swallow up to 4 tablets in succession.

Subjects were excluded from participation in the study for prior treatment with omadacycline, recent use of other investigational drugs; ECG abnormalities; inability to tolerate oral medications; pregnancy or breastfeeding; use of tobacco products, prescription drugs, herbal supplements, or over-the-counter medications or intake of xanthine (e.g., caffeine)-containing food or beverages within a specified time frame before study initiation; blood loss/donation; low hemoglobin levels; high creatinine or blood urea nitrogen levels; urinary obstruction/difficulty voiding; positive alcohol or drug test; hypersensitivity or allergy to any tetracycline; signs of liver disease or liver injury; significant illness within 2 weeks of study initiation; any planned medical intervention that might interfere with the study; or a history of diseases or medical conditions as specified in the study protocol.

Study Design

On Day 1 through Day 5 of each period, subjects received once-daily, after a fast of 6 hours, one of the following treatments (omadacycline or placebo) according to the randomization schedule:

A. 300 mg omadacycline (2×150-mg tablets)

AP. Placebo for 300 mg omadacycline (2× placebo tablets)

B. 450 mg omadacycline (3×150-mg tablets)

BP. Placebo for 450 mg omadacycline (3× placebo tablets)

C. 600 mg omadacycline (4×150-mg tablets)

CP. Placebo for 600 mg omadacycline (4× placebo tablets)

All doses of study drug were administered in the morning with no food or drink except for water at least 6 hours prior to dosing. Subjects then had no food or drink except water for at least 2 hours after dosing and no dairy products, antacids, or multivitamins for 4 hours after dosing.

Before the dosing, subjects underwent screening evaluations to determine eligibility within 21 days before dosing in Period 1. Subjects were then admitted to the clinical site on the day before dosing (Day −1 of Period 1) for baseline evaluations. Before dosing on Day 1 of Period 1, up to 30 subjects (24 omadacycline, 6 placebo) were randomly assigned to 1 of 3 treatment sequences using a Latin Square design as presented in the following table:

| Sequence | Subsequence | Number of Subjects | Period 1 | Period 2 | Period 3 |
|---|---|---|---|---|---|
| 1 | 1A | 8 omadacycline | A | C | B |
|  | 1B | 2 placebo | AP | CP | BP |
| 2 | 2A | 8 omadacycline | B | A | C |
|  | 2B | 2 placebo | BP | AP | CP |
| 3 | 3A | 8 omadacycline | C | B | A |
|  | 3B | 2 placebo | CP | BP | AP |

About ten subjects were randomly assigned to each sequence. Placebo was administered to 2 subjects in each sequence as a reference to assess tolerability. Subjects assigned to omadacycline received omadacycline during all 3 periods and at all tested dose levels. Subjects assigned to placebo received placebo during all 3 periods. Investigators and subjects were blinded to whether the subject was receiving omadacycline or placebo.

Study Asessment

1. Plasma Pharmacokinetics

Serial blood samples for pharmacokinetic (PK) analysis of omadacycline were collected at specified time points through 24 hours after dosing on Day 1 and Day 5 of each period. Specifically, blood samples for PK assessments of omadacycline were collected from all subjects at the following time points: before dosing (predose) and at 0.5, 1, 1.5, 2, 2.5, 3, 4, 6, 8, 12, 16, and 24 hours after dosing on Day 1 and Day 5 in each period. The 24-hour blood sample for Day 1 was collected prior to dosing on Day 2 for each period.

Non-compartmental PK parameters were determined on Days 1 and 5 of each period from plasma omadacycline concentration and actual time data using Phoenix® WinNonlin® (Certara, Princeton, N.J.) Version 6.2.1., including area under the plasma concentration versus time curve (AUC) from time 0 to 24 hours after dosing ($AUC_{0-24}$), AUC from time 0 to the last quantifiable concentration ($AUC_{last}$), maximum observed plasma concentration ($C_{max}$), time to reach maximum observed plasma concentration ($T_{max}$), terminal elimination half-life ($T_{1/2}$), terminal phase rate constant ($\lambda_z$) and the accumulation factor (Rac) of $AUC_{0-24}$ and $C_{max}$.

Subjects that received omadacycline and had at least one evaluable PK parameter were included in the PK analysis population; however, subjects may have been excluded from the PK population if they missed doses, had diarrhea, or had vomiting at or before a time equal to twice the median $T_{max}$.

2. Urine Pharmacokinetics

Urine samples were collected from a subset of subjects at specified intervals on Day 5 of Period 2 and on Day 1 and Day 5 of Period: predose, 0 to 4, 4 to 8, 8 to 12, and 12 to 24 hours after dosing. The 12 to 24-hour interval urine sample for Day 1 was collected prior to dosing on Day 2. Urine samples were only collected from a subset of subjects because analysis of urine PK was added by an amendment to the study protocol after the study was already underway.

The following urine PK parameters were determined from urine omadacycline concentration and collection interval data using SAS Version 9.2: renal clearance (CLr), fraction of the dose excreted unchanged in urine from 0 to 24 hours after dosing ($Fe_{0-24}$), and amount of drug excreted unchanged in urine over 24 hours after dosing ($Ae_{t1-t2}$). Additional parameters $Ae_{0-4}$, $Ae_{4-8}$, $Ae_{8-12}$, $Ae_{12-24}$, and $Ae_{0-24}$ were also calculated.

3. Safety and Tolerability

Safety assessments include monitoring of adverse events (AEs), clinical laboratory test results, vital sign measurements, 12-lead electrocardiogram (ECG) results, and physical examination findings. All randomly assigned subjects who received at least one dose of any study drug (omadacycline or placebo) were included in the safety analysis population. Adverse events were coded by preferred term and system organ class using MedDRA Version 17.1.

Safety and tolerability were assessed by the monitoring and recording of AEs, clinical laboratory test results (hematology, serum chemistry, and urinalysis), vital sign measurements (oral body temperature, systolic blood pressure, diastolic blood pressure, and HR), 12-lead ECG results, and physical examination findings.

Statistical Analysis for Pharmacokinetic Study:

Individual plasma and urine concentration and time deviation data were presented in data listings. Plasma and urine concentration data were summarized by day and time point or interval for each treatment using descriptive statistics (number of subjects, mean, SD, coefficient of variation [CV], median, minimum, and maximum). Concentrations that were below the limit of quantification (BLQ) were treated as zero in the plasma and urine concentration descriptive statistics summaries. Mean and individual plasma concentration versus time profiles were presented in figures on both linear and semilogarithmic scales.

Noncompartmental PK parameters were determined from plasma concentration and actual time data using Phoenix® WinNonlin® (Certara, Princeton, N.J.) Version 6.2.1 or higher. Urine PK parameters were determined from urine concentration and collection interval data using SAS Version 9.2 or higher. All further statistical analyses were performed using SAS® software (SAS Institute, Cary, N.C.), Version 9.2.

For the PK analysis, BLQ values were treated as zero with the exception that a BLQ value between 2 quantifiable concentrations were set as missing. Missing concentrations were treated as missing from the PK parameter calculations. If consecutive BLQ concentrations were followed by quantifiable concentrations in the terminal phase, those concentrations after BLQ concentrations were treated as missing.

The individual PK parameters were presented in data listings. Descriptive statistics (number of subjects, mean, SD, CV, median, minimum, and maximum) were calculated for the PK parameter estimates after dosing on Day 1 and Day 5 of each period (e.g., $AUC_{0-24}$, $AUC_{last}$, $C_{max}$, $T_{max}$, $T_{1/2}$, and Rac [Day 5 only] from plasma concentrations; CLr, $Fe_{0-24}$, and $Ae_{0-24}$ from urine concentrations). Geometric means were included for $AUC_{0-24}$, $AUC_{last}$, and $C_{max}$.

A linear mixed-effect model (SAS PROC MIXED) with treatment (A, B, and C), sequence (1A, 2A, and 3A), and treatment period as fixed effects and subject nested within sequence as a random effect were fitted to the natural log-transformed dose normalized PK parameters $AUC_{0-24}$/Dose, $AUC_{last}$/Dose, and $C_{max}$/Dose after dosing on Day 1 and Day 5 of each period for use in estimation of effects and construction of confidence intervals (CIs). Point estimates and 90% CIs for differences on the log scale were exponentiated to obtain estimates for the ratios of geometric means and respective 90% CIs on the original scale. No adjustment was made for multiplicity.

Dose linearity across all 3 dose levels was assessed by fitting omadacycline $C_{max}$, $AUC_{last}$, and $AUC_{0-24}$ after both the Day 1 and Day 5 doses to a power model (10): $\ln(PK)=a+b\times\ln(Dose)+error$, where PK was the PK parameter, a was the intercept and b was the slope. The estimates of slope b were reported along with the corresponding 2-sided 90% CIs.

For statistical analysis of accumulation of omadacycline, a linear mixed-effect model with day as a fixed effect and subject as random effect was fitted to the natural log-transformed $C_{max}$ and $AUC_{0-24}$ to construct 90% CIs for Day 5 compared with Day 1 (at each dose level separately).

Results a. Demographics, Baseline Characteristics, and Disposition of Study Subjects Of the 33 subjects enrolled in the study, 26 were assigned to receive omadacycline and 7 were assigned to receive placebo. Demographic and baseline characteristics were generally similar between omadacycline and placebo treatment groups (Table 4-1) and across all omadacycline treatment sequences (data not shown). The majority of subjects in the study were white (57.6%) and male (81.8%). The overall mean age of subjects was 36.9 years, with a range of 21 to 55 years.

TABLE 4-1

Demographics and Baseline Characteristics of Subjects in the Study[a]

|  | Omadacycline (N = 26) | Placebo (N = 7) | Overall (N = 33) |
|---|---|---|---|
| Age, years |  |  |  |
| Mean (±SD) | 35.6 (±10.4) | 41.9 (±11.6) | 36.9 (±10.8) |
| Min, max | 21, 55 | 25, 53 | 21, 55 |
| Sex, n (%) |  |  |  |
| Male | 21 (80.8) | 6 (85.7) | 27 (81.8) |
| Female | 5 (19.2) | 1 (14.3) | 6 (18.2) |
| Race, n (%) |  |  |  |
| White | 15 (57.7) | 4 (57.1) | 19 (57.6) |
| Black or African American | 9 (34.6) | 3 (42.9) | 12 (36.4) |
| Asian | 2 (7.7) | 0 | 2 (6.1) |
| Ethnicity, n (%) |  |  |  |
| Hispanic or Latino | 10 (38.5) | 3 (42.9) | 13 (39.4) |
| Not Hispanic or Latino | 16 (61.5) | 4 (57.1) | 20 (60.6) |
| Height, cm |  |  |  |
| Mean (±SD) | 173.12 (±9.17) | 172.89 (±4.31) | 173.07 (±8.32) |
| Min, max | 155.2, 192.4 | 165.6, 177.4 | 155.2, 192.4 |

TABLE 4-1-continued

Demographics and Baseline Characteristics of Subjects in the Study[a]

|  | Omadacycline (N = 26) | Placebo (N = 7) | Overall (N = 33) |
|---|---|---|---|
| Weight, kg |  |  |  |
| Mean (±SD) | 78.67 (±10.33) | 83.77 (±4.80) | 79.75 (±9.60) |
| Min, max | 62.7, 101.4 | 76.7, 90.4 | 62.7, 101.4 |
| Body mass index, kg/m² |  |  |  |
| Mean (±SD) | 26.25 (±2.72) | 28.04 (±1.45) | 26.63 (±2.59) |
| Min, max | 19.4, 29.8 | 25.8, 29.9 | 19.4, 29.9 |

[a]Results for Safety Population

All 33 subjects received at least one dose of study drug (omadacycline or placebo) and were included in the safety analysis population. Twenty-five of the 26 omadacycline-treated subjects (96.2%) were included in the PK analysis population (one subject was excluded from this population due to vomiting after dosing). Four omadacycline-treated subjects (15.4%) and one placebo-treated subject (14.3%) discontinued the study; these early discontinuations were due to treatment-emergent adverse events (TEAEs) in 4 subjects (see below); in addition one omadacycline-treated subject was lost to follow-up. Thus, 22 subjects received all 5 doses of 300-, 450-, and 600-mg omadacycline and 6 subjects received all 5 doses of placebo in Periods 1, 2, and 3. These subjects were considered to have completed the study.

b. Plasma Pharmacokinetics

At all tested omadacycline dose levels on both Day 1 and Day 5 of each 5-day treatment period, mean plasma omadacycline concentrations peaked 2.5 hours after dosing ($T_{max}$) and omadacycline was measurable in plasma for up to 24 hours after dosing (the last sampling time) (FIG. 5 and Table 4-2).

TABLE 4-2

Plasma Pharmacokinetic Parameters of Omadacycline by Dose on Days 1 and 5 of Dosing[a]

| | Omadacycline Dose | | | | | |
|---|---|---|---|---|---|---|
| | Day 1 | | | Day 5 | | |
| Parameter | 300 mg (n = 25) | 450 mg (n = 24) | 600 mg (n = 24) | 300 mg (n = 23) | 450 mg (n = 24) | 600 mg (n = 23) |
| Mean $AUC_{0-24}$, ng · h/mL (CV) | 6644.8 (25.3) | 8976.5 (26.6) | 10020.5 (25.7) | 9267.2 (26.8) | 13366.7 (26.0) | 16420.3 (27.1) |
| Mean $C_{max}$, ng/mL (CV) | 648.8 (24.0) | 874.2 (26.6) | 954.5 (23.2) | 808.8 (25.9) | 1077.3 (25.0) | 1305.5 (26.6) |
| Mean $T_{max}$, h (Min, max) | 2.50 (1.50, 3.00) | 2.50 (1.50, 3.00) | 2.51 (1.00, 3.00) | 2.50 (1.00, 3.00) | 2.50 (1.50, 4.00) | 2.50 (2.00, 4.00) |
| Mean $T_{1/2}$, h (CV) | 13.66 (12.5)[b] | 13.45 (12.9)[c] | 13.03 (11.8)[c] | 15.49 (10.7)[d] | 16.83 (8.1)[c] | 16.75 (6.8)[d] |

[a]Results for Pharmacokinetic Population
[b]n = 24 ($T_{1/2}$ was not estimable for 1 subject)
[c]n = 23 ($T_{1/2}$ was not estimable for 1 subject)
[d]n = 21 ($T_{1/2}$ was not estimable for 2 subjects)
CV, coefficient of variation
Note:
One 300 mg omadacycline subject and one 600 mg omadacycline subject were excluded from the Day 5 summary due to vomiting before reaching the pharmacokinetic steady state on Day 5

Omadacycline total exposure ($AUC_{0-24}$ and $AUC_{last}$) and peak concentrations ($C_{max}$) increased with increasing omadacycline dose (300 vs 450 vs 600 mg) on both Day 1 and Day 5, and were higher on Day 5 than on Day 1 for corresponding doses (FIG. 5 and Table 4-2). The 5 mean half-life of omadacycline in plasma ($T_{1/2}$) was similar across the 3 tested dose levels, ranging from 13.03 to 13.66 hours on Day 1 and from 15.49 to 16.83 hours on Day 5 (Table 4-2). Between-subject variability in systemic omadacycline exposure was low and was similar at all three tested dose levels, with coefficients of variation (CVs) ranging from 23.2% to 26.6% for $C_{max}$, $AUC_{0-24}$, and $AUC_{last}$ on Day 1 and from 25.0% to 27.1% for $C_{max}$, $AUC_{0-24}$, and $AUC_{last}$ on Day 5 (Table 4-2).

Although omadacycline $AUC_{0-24}$, $AUC_{last}$ and $C_{max}$ increased with increasing omadacycline dose, the observed increases in exposure were less than dose proportional on both days of analysis (Tables 4-2 and 4-3).

300-mg omadacycline was 9267 ng·h/mL, which is consistent with results of previous studies with 300 mg oral dosing. Both $AUC_{0-24}$ and $C_{max}$ increased with increasing dose and were nearly, but somewhat less than, dose-proportional (74%-88% of expected). This was the case on both Day 1 and Day 5 of dosing. Due to its relatively long half-life (mean=~13 h on Day 1, ~16 h on Day 5), omadacycline accumulated in plasma over the course of 5 consecutive days of dosing. Thus, at all tested dose levels, systemic exposure on Day 5 was ~50% higher than on Day 1. This degree of accumulation is also consistent with that observed following multiple once-daily dosing of IV or oral formulations of omadacycline in early pharmacology studies.

In terms of systemic exposure, this study showed that omadacycline plasma concentrations on Day 1 of 450-mg dosing were similar to those on Day 5 of 300-mg dosing (mean $AUC_{0-24}$=8976.5 and 9267.2 ng·h/mL, respectively). For indications in which the therapeutic dosing regimen

TABLE 4-3

Statistical Analysis of Dose-Normalized Omadacycline Pharmacokinetic Parameters on Days 1 and 5 of Dosing[a]

| Parameter | Treatment | N | Geometric LS Means | Treatment Comparison | Ratio of Geometric LS Means (%) | 90% CI of Ratio (%) |
|---|---|---|---|---|---|---|
| Day 1 |  |  |  |  |  |  |
| $AUC_{0-24}$/Dose | 300 mg | 25 | 21.32 | 450/300 | 87.44 | (77.41, 98.77) |
| (ng · h/mL/mg) | 450 mg | 24 | 18.64 | 600/450 | 86.79 | (76.71, 98.20) |
|  | 600 mg | 24 | 16.18 | 600/300 | 75.89 | (67.20, 85.71) |
| $C_{max}$/Dose | 300 mg | 25 | 2.09 | 450/300 | 86.71 | (76.17, 98.71) |
| (ng/mL/mg) | 450 mg | 24 | 1.81 | 600/450 | 85.26 | (74.76, 97.23) |
|  | 600 mg | 24 | 1.54 | 600/300 | 73.92 | (64.95, 84.14) |
| Day 5 |  |  |  |  |  |  |
| $AUC_{0-24}$/Dose | 300 mg | 23 | 30.09 | 450/300 | 95.82 | (90.39, 101.59) |
| (ng · h/mL/mg) | 450 mg | 24 | 28.83 | 600/450 | 91.78 | (86.58, 97.30) |
|  | 600 mg | 23 | 26.46 | 600/300 | 87.95 | (82.96, 93.25) |
| $C_{max}$/Dose | 300 mg | 23 | 2.62 | 450/300 | 88.58 | (83.19, 94.32) |
| (ng/mL/mg) | 450 mg | 24 | 2.32 | 600/450 | 90.72 | (85.20, 96.60) |
|  | 600 mg | 23 | 2.11 | 600/300 | 80.36 | (75.47, 85.58) |

[a]Results for Pharmacokinetic Population
ANOVA analysis; see Materials and Methods for details
CI, confidence interval;
LS, least squares
Note:
One 300 mg omadacycline subject and one 600 mg omadacycline subject were excluded from the Day 5 statistical analysis due to vomiting before reaching the pharmacokinetic steady state on Day 5

Statistical analyses showed that with an increase in dose from 300 mg to 600 mg, omadacycline exposure (based on dose-normalized $AUC_{0-24}$) on Day 1 was 76% of that predicted if exposure were perfectly dose-proportional (Table 4-3); on Day 5, the observed increase in omadacycline exposure was 88% of predicted (Table 4-3). Analysis of $C_{max}$ values similarly demonstrated that omadacycline concentrations were dose-linear, but less than dose-proportional in this study (Tables 4-2 and 4-3).

Statistical analyses also revealed accumulation of omadacycline in plasma following once-daily dosing for 5 consecutive days. Depending on dose, accumulation ratios between Day 5 and Day 1 ranged from 1.40 to 1.62 for $AUC_{0-24}$ and from 1.24 to 1.35 for $C_{max}$ (data not shown). These findings are consistent with the long half-life of omadacycline in plasma.

The above data showed that mean concentrations of omadacycline peaked at 2.5 hours and remained measurable up to 24 hours (the last tested timepoint) at all omadacycline dosing levels (300, 450, and 600 mg). On Day 5, mean steady state exposure ($AUC_{0-24}$) in subjects dosed with incorporates 300 mg daily oral dosing, these data support a strategy of using an initial oral "loading dose" of 450 mg once-daily for 1-2 days, followed by 300-mg once-daily oral dosing. Such a strategy could potentially eliminate the need for an IV phase of treatment.

c. Urine Pharmacokinetics

Because urine sample collection and PK analysis were added to the study by protocol amendment after the study was underway, only a limited number of samples were evaluated (samples from 9 subjects on Day 5 of Period 2 and samples from 8 subjects on Day 1 and Day 5 of Period 3). While this sample size was too small to make meaningful comparisons between omadacycline dose groups, the results of the analysis did provide an overall indication of partial omadacycline renal clearance and urinary excretion.

For all omadacycline dose groups, the mean fraction of the dose excreted unchanged in urine from 0 to 24 hours after dosing ($Fe_{0-24}$) ranged from ~5% to ~7% on Day 1 and from ~7% to ~9% on Day 5. Renal clearance (CLr) ranged from 2.8 to 4.2 IJh on Day 1 and from 2.4 to 3.3 L/h on Day 5 (Table 4-4).

TABLE 4-4

Urine Pharmacokinetic Parameters of Omadacycline
by Dose on Days 1 and 5 of Dosing[a]

| | Omadacycline Dose | | | | | |
|---|---|---|---|---|---|---|
| | Day 1 | | | Day 5 | | |
| Parameter[b] | 300 mg (n = 2) | 450 mg (n = 3) | 600 mg (n = 1) | 300 mg (n = 3) | 450 mg (n = 5) | 600 mg (n = 4) |
| $Ae_{0-24}$ (mg) | 20.37 (8.3) | 25.06 (16.8) | 31.96 | 26.14 (14.6) | 30.81 (33.0) | 51.82 (14.8) |
| $Fe_{0-24}$ (%) | 6.79 (8.3) | 5.57 (16.8) | 5.33 | 8.71 (14.6) | 6.85 (33.0) | 8.64 (14.8) |
| CLr (L/h) | 3.01 (11.4) | 2.80 (9.6) | 4.17 | 3.28 (27.2) | 2.38 (34.9) | 3.05 (19.9) |

[a]Results for Pharmacokinetic Population
[b]Mean (CV)
CV, coefficient of variation
Note:
One 600 mg omadacycline subject was excluded from the summary due to vomiting before reaching the pharmacokinetic steady state on Day 5

Urine PK analyses in a subset of subjects provided preliminary indications of partial renal clearance and urinary excretion of omadacycline. On Day 5, depending on dose level, ~7% to ~9% of the administered oral dose was excreted unchanged in the urine over 24 hours. This represents approximately 20% to 25% of the absorbed dose since it is known that the absolute bioavailability of the tablet formulation used in this study is 35%. Presence of unchanged omadacycline in the urine suggests that it may be useful in urinary tract infections, an indication that is currently being explored.

d. Safety and Tolerability

Overall, 12 of the 33 subjects in the safety population reported a total of 36 TEAEs during the study (Table 4-5).

The highest percentage of TEAEs was classified as gastrointestinal (GI) disorders. The most frequently reported TEAE was nausea, which occurred in ≤7.7% of the omadacycline 300 and 450 mg dose groups and 16.7% of the 600 mg group. All of the TEAEs reported in this study were either mild or moderate in severity. There were no serious TEAEs (SAEs) reported during the study. Four subjects experienced TEAEs leading to study discontinuation, including one subject at each of the 3 omadacycline dose levels and 1 subject in the placebo group.

There were no clinically significant findings in analyses of vital sign measurements, physical examination, ECG results, hematology or urinalysis parameters. Serum chemistry analyses showed that between baseline and Day 5 of each

TABLE 4-5

Summary of Treatment-Emergent Adverse Events[a]

| | Omadacycline Dose | | | Omadacycline | Placebo |
|---|---|---|---|---|---|
| | 300 mg (n = 26) | 450 mg (n = 24) | 600 mg (n = 24) | Overall (n = 26) | Overall (n = 7) |
| n (%) of subjects with: | | | | | |
| Any TEAE | 5 (19.2) | 3 (12.5) | 6 (25.0) | 10 (38.5) | 2 (28.6) |
| Treatment-related TEAE | 4 (15.4) | 2 (8.3) | 6 (25.0) | 9 (34.6) | 1 (14.3) |
| Most frequent TEAEs (seen in >1 study subject), n (%) | | | | | |
| Nausea | 2 (7.7) | 1 (4.2) | 4 (16.7) | 6 (23.1) | 0 |
| Vomiting | 2 (7.7) | 0 | 1 (4.2) | 3 (11.5) | 0 |
| Diarrhea | 0 | 0 | 2 (8.3) | 2 (7.7) | 0 |
| Dizziness | 2 (7.7) | 0 | 1 (4.2) | 3 (11.5) | 0 |
| ALT increased | 0 | 1 (4.2) | 1 (4.2) | 2 (7.7) | 0 |
| TEAEs leading to early discontinuation of study drug, n (%) | | | | | |
| All | 1 (3.8) | 1 (4.2) | 1 (4.2) | 3 (11.5) | 1 (14.3) |
| Nausea | 1 (3.8) | 0 | 0 | 1 (3.8) | 0 |
| Vomiting | 1 (3.8) | 0 | 0 | 1 (3.8) | 0 |
| ALT increased | 0 | 1 (4.2) | 0 | 1 (3.8) | 0 |
| Lipase increased | 0 | 0 | 1 (4.2) | 1 (3.8) | 0 |
| Syncope | 0 | 0 | 0 | 0 | 1 (14.3)[b] |

[a]Results for Safety Population
[b]vasovagal syncope following a blood draw
ALT, alanine aminotransferase;
TEAE, treatment-emergent adverse event TEAEs were reported by 38.5% of subjects that received omadacycline and 28.6% of subjects that received placebo.

dosing period, the median change in alanine aminotransferase (ALT) concentration was −2.0, 5.0 and 19.5 IU/L in subjects dosed with 300, 450 and 600 mg omadacycline, respectively. The corresponding changes in placebo groups ranged from −5.0 to −1.0 IU/L. No substantial changes in median aspartate aminotransferase (AST), bilirubin or other serum chemistry parameters were noted. The highest individual ALT value was 150 IU/L (2.7-fold above the upper limit of normal [ULN]), which occurred in a subject who first received 450 mg omadacycline in Period 1 then 300 mg in Period 2 and then was discontinued due to the liver enzyme changes; this subject's bilirubin values remained within the normal range at all time points assessed.

The plasma PK findings indicate that higher systemic drug exposure can be achieved by increasing the amount of omadacycline administered per dose during once-daily oral dosing, but that the exposure benefit is not dose-proportional. Moreover, increasing omadacycline dosing beyond a certain point appears to have adverse effects in terms of safety and tolerability. While multiple doses of 300, 450, and 600 mg were all generally well-tolerated in this study (all TEAEs were either mild or moderate in severity), there were some differences between the doses. The frequency of treatment-related TEAEs did not increase with an increase in omadacycline dose from 300 to 450 mg (15.4% vs 8.3%), but such events were more frequent with 600 mg (25.0%). Within the most frequent class of TEAEs, GI disorders, nausea occurred with incidence at least 9% higher for the 600 mg dose level than for the lower doses, and the only 2 reports of diarrhea occurred with 600 mg. In addition, serum chemistry analyses showed a small but notable dose-dependent increase in median ALT concentrations. While no individual ALT values exceeded 3-fold above the ULN, the higher median ALT at 600 mg suggests an increased chance of more significantly elevated serum transaminase levels with this dose. Based on these findings, for situations in which an oral dose above 300 mg may be beneficial, 450 mg was identified as the oral dose most likely to provide higher omadacycline exposure with favorable safety and tolerability.

In summary, this phase 1 study investigated the pharmacokinetics (PK) and safety/tolerability of multiple oral omadacycline doses higher than 300 mg. Using a 3-period crossover design, healthy adults were randomized to receive omadacycline (300-, 450- and 600-mg in variable sequence; n=26) or placebo (n=7) once daily for 5 consecutive days per period. In plasma, omadacycline maximum concentration and total exposure increased with increasing dose, but were less than dose-proportional (74% to 88% of expected). The kinetics of omadacycline plasma accumulation were similar between dose levels; exposure on Day 5 was ~50% higher than on Day 1. Omadacycline plasma concentrations on Day 1 of 450 mg dosing were similar to those on Day 5 of 300 mg dosing. Urine PK analyses indicated partial renal clearance and urinary excretion of unchanged omadacycline. All doses were generally well-tolerated. These results support the use of once-daily 450-mg oral omadacycline as part of the oral only dosing regimen, such as using once-daily 450-mg oral omadacycline (either one or two doses) as loading dose before stepping down to once-daily 300-mg oral omadacycline, or in a dosing regimen using once-daily 450-mg oral omadacycline throughout the treatment.

What is claimed is:

1. A method of treating Community-Acquired Bacterial Pneumonia (CABP) in a subject in need of treatment thereof, comprising administering to said subject 9-[(2,2-dimethylpropyl amino)-methyl]-minocycline or a salt thereof according to the following dosing regimen:

(1) three intravenous doses of about 100 mg each, administered 12 hours apart, followed by, (2) optionally, one or more intravenous doses of about 100 mg each, each administered 24 hours following the immediate preceding intravenous dose, followed by, (3) optionally, one oral dose of about 300 mg, administered in the morning and 12-24 hrs after the immediate preceding intravenous dose, followed by, (4) optionally, one or more oral doses of about 300 mg each, each administered 24 hours following the immediate preceding oral dose, such that said subject is treated.

2. The method of claim 1, wherein the steps are completed within 7 days, 8 days, 9 days, 10 days, 11 days, 12 days, 13 days, 14 days, 15 days, 16 days, 17 days, 18 days, 19 days, or 20 days.

3. The method of claim 1, wherein the number of days of IV dosing is 3-6 days.

4. The method of claim 1, comprising one or more oral doses, and wherein the number of days of IV dosing is 4-7 days.

5. The method of claim 4, wherein the number of days of oral dosing is 5-7 days.

6. The method of claim 4, wherein the number of days of IV dosing is 5 days, and the number of days of oral dosing is 5 days.

7. The method of claim 1, wherein said CABP is caused by *Staphylococcus aureus* including methicillin-resistant *Staphylococcus aureus* (MRSA), *Streptococcus pneumoniae* including penicillin-resistant *Streptococcus pneumoniae* (PRSP), *Haemophilus influenzae, Moraxella catarrhalis, Klebsiella pneumoniae, Legionella pneumophila, Chlamydophila pneumoniae, Mycoplasma pneumoniae, Chlamydophila psittaci, Coxiella burnetii, Escherichia coli*, or a combination thereof.

8. The method of claim 1, wherein said subject is a human.

9. The method of claim 1, wherein each of said oral dose is administered independently as two 150-mg tablets.

10. The method of claim 1, wherein each of said intravenous dose is administered continuously over about 30 minutes.

11. The method of claim 1, wherein said dosing regimen has a clinical success rate that is within 10% (or 12.5%) margin of non-inferiority compared to moxifloxacin administered as 400 mg intravenous dose once every 24 hours for three or more days, followed by one or more doses of 400 mg oral doses of moxifloxacin once every 24 hours.

12. The method of claim 1, wherein said subject experience improvement, at day 3 to day 5 after step (1), in at least two symptoms selected from: chest pain, frequency or severity of cough, amount of productive sputum, and difficulty breathing, wherein said symptoms are evaluated on a four-point scale of absent, mild, moderate, and severe, and wherein improvement is at least a one-point improvement from baseline to the assessment at said day 3 to day 5.

13. The method of claim 1, wherein said subject, at day 3 to day 5 after step (1), experience improvement in at least two symptoms and no worsening in any of the symptoms selected from: chest pain, frequency or severity of cough, amount of productive sputum, and difficulty breathing, and improvement in at least one vital sign selected from: body temperature, blood pressure, heart rate, and respiratory rate.

14. The method of claim 1, wherein the subject undergoes fasting overnight, with no food or drink except water for at least 6 hours, just before step (3) dosing (if present), and wherein the subject continues fasting after step (3) dosing, with no food for 2 hours, and no dairy products for 4 hours.

15. The method of claim 1, wherein said salt is a tosylate salt.

16. The method of claim 1, which method has a clinical success rate of about 70%-100%; about 75-95%, about 80-95%, about 75-90%, about 80-90%, about 75-85%, about 80-85%, about 85-90%, about 90-95%, about 80-82%, or about 81%; or about 75-85%, observed at about 72-120 hours after the administration of the first intravenous dose.

17. The method of claim 1, wherein said subject has CABP categorized as PORT Risk Class III or IV.

18. The method of claim 1, wherein gastrointestinal (GI) adverse events (AEs) associated with treatment of said subject are mild, or do not result in discontinuation of therapy with said method.

19. The method of claim 1, wherein treatment of said subject (1) does not result in increased risk of *C. difficile* (e.g., *C. difficile* colitis and Pseudomembranous colitis) infection in said subject, or (2) does not substantially disrupting gut microbiome in said subject.

20. The method of claim 1, wherein the steps are completed within 7-14 days.

21. A method of treating Community-Acquired Bacterial Pneumonia (CABP) in a subject in need of treatment thereof, comprising administering to said subject 9-[(2,2-dimethyl-propyl amino)-methyl]-minocycline or a salt thereof according to the following dosing regimen:
(1) three intravenous doses of about 100 mg each, administered 12 hours apart, followed by,
(2) optionally, one or more intravenous doses of about 100 mg each, each administered 24 hours following the immediate preceding intravenous dose, followed by,
(3) one or more oral doses of about 300 mg each, each administered 24 hours following the immediate preceding dose,
such that said subject is treated.

22. The method of claim 21, wherein step (2) consists of one intravenous dose of about 100 mg of said subject 9-[(2,2-dimethyl-propyl amino)-methyl]-minocycline or salt thereof.

23. The method of claim 21, wherein the steps are completed within 7-14 days.

24. A method of treating Community-Acquired Bacterial Pneumonia (CABP) in a subject in need of treatment thereof, comprising administering to said subject 9-[(2,2-dimethyl-propyl amino)-methyl]-minocycline or a salt thereof according to the following dosing regimen:
(1) three oral doses of about 300-450 mg each, administered 12 hours apart, followed by,
(2) optionally, one or more oral doses of about 300-600 mg each, each administered 24 hours following the immediate preceding oral dose,
such that said subject is treated.

25. The method of claim 24, wherein each oral dose is about 300 mg.

26. The method of claim 24, wherein each oral dose in step (1) is about 300 mg.

27. The method of claim 24, wherein each oral dose in step (1) is about 450 mg.

28. The method of claim 24, wherein the first two oral doses of step (1) are each 450 mg, and the last oral dose of step (1) is about 300, or 450 mg.

29. The method of claim 24, wherein the steps are completed within 7 days, 8 days, 9 days, 10 days, 11 days, 12 days, 13 days, 14 days, 15 days, 16 days, 17 days, 18 days, 19 days, 20 days, or 21 days.

30. The method of claim 24, wherein the steps are completed within 7-14 days.

31. The method of claim 24, wherein the subject undergoes fasting overnight, with no food or drink except water for at least 6 hours, just before each oral dosing, and wherein the subject continues fasting after each oral dosing, with no food for 2 hours, and no dairy products for 4 hours.

32. The method of claim 24, wherein said salt is a tosylate salt.

33. The method of claim 24, wherein said subject has CABP categorized as PORT Risk Class III or IV.

34. The method of claim 24, wherein gastrointestinal (GI) adverse events (AEs) associated with treatment of said subject are mild.

35. The method of claim 24, wherein GI adverse events (AEs) associated with treatment of said subject do not result in discontinuation of therapy with said method.

36. The method of claim 24, wherein treatment of said subject (1) does not result in increased risk of *C. difficile* infection in said subject, or (2) does not substantially disrupting gut microbiome in said subject.

37. The method of claim 36, wherein said subject is at risk of, or is predisposed to, developing a *C. difficile* infection.

38. The method of claim 37, wherein said subject has recently been treated with one or more antibiotics, has had surgery of the gastrointestinal tract, has a disease of the colon, has a kidney disease, has a weakened immune system; is on chemotherapy, has previously had *C. difficile* infection, is 65 years or older, takes proton-pump inhibitors, or is living in an environment that predisposes said subject to developing *C. difficile* infection.

39. A method of treating Community-Acquired Bacterial Pneumonia (CABP) in a subject in need of treatment thereof, comprising administering to said subject 9-[(2,2-dimethyl-propyl amino)-methyl]-minocycline or a salt thereof according to the following dosing regimen:
(1) one or two once-daily oral dose(s) of about 450-600 mg (administered 24 hrs apart for two once-daily oral doses), followed by,
(2) one or more oral doses of about 300-600 mg each, each administered 24 hours following the immediate preceding oral dose,
such that said subject is treated.

40. The method of claim 27, wherein each oral dose in step (2) is about 300 mg.

41. The method of claim 39, wherein said dosing regimen is:
(1) one or two once-daily oral dose(s) of about 450 or 600 mg, administered 24 hrs apart for two once-daily oral doses, followed by,
(2) one or more oral doses of about 300 mg each, each administered 24 hours following the immediate preceding oral dose.

42. The method of claim 39, wherein said dosing regimen is:
(1) two once-daily oral doses of about 450 mg, administered 24 hrs apart, followed by,
(2) one or more oral doses of about 300 mg each, each administered 24 hours following the immediate preceding oral dose.

43. The method of claim 39, wherein the steps are completed within 7-14 days.

* * * * *